United States Patent
Yamagata

(10) Patent No.: US 10,206,643 B2
(45) Date of Patent: Feb. 19, 2019

(54) MEDICAL IMAGE DIAGNOSTIC APPARATUS AND ULTRASONIC DIAGNOSTIC APPARATUS

(71) Applicant: Toshiba Medical Systems Corporation, Otawara-shi (JP)

(72) Inventor: Hitoshi Yamagata, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1173 days.

(21) Appl. No.: 14/447,863

(22) Filed: Jul. 31, 2014

(65) Prior Publication Data

US 2015/0038827 A1    Feb. 5, 2015

(30) Foreign Application Priority Data

Jul. 31, 2013   (JP) .................................. 2013-159856
Jul. 31, 2013   (JP) .................................. 2013-159857

(51) Int. Cl.
*A61B 5/00* (2006.01)
*A61B 6/00* (2006.01)
(Continued)

(52) U.S. Cl.
CPC .............. *A61B 6/481* (2013.01); *A61B 5/055* (2013.01); *A61B 6/504* (2013.01); *A61B 8/481* (2013.01);
(Continued)

(58) Field of Classification Search
CPC ......... A61B 6/481; A61B 6/504; A61B 5/055; A61B 8/481; A61B 6/037; A61B 6/5235; A61B 6/4241; A61B 8/4416; A61B 6/4417; A61B 6/032; A61K 49/0002; G01R 33/5605; G01R 33/5601
See application file for complete search history.

(56) References Cited

U.S. PATENT DOCUMENTS

2006/0058622 A1*   3/2006   Tearney ............... A61B 5/0062
                                                  600/407
2007/0104317 A1*   5/2007   Ohishi .................. A61B 6/481
                                                  378/98.12
(Continued)

FOREIGN PATENT DOCUMENTS

JP    2009-23929        2/2009
JP    2015-524329 A     8/2015
(Continued)

OTHER PUBLICATIONS

Moritz F. Kircher et al. "Molecular Body Imaging: MR Imaging, CT, and US. Part I. Principles", Radiology: vol. 263, No. 3, 2012, 11 pages.

(Continued)

*Primary Examiner* — Joel Lamprecht
(74) *Attorney, Agent, or Firm* — Oblon, McClelland, Maier & Neustadt, L.L.P.

(57) ABSTRACT

According to one embodiment, a medical image diagnostic apparatus includes an imaging unit, an image generation unit, and a display unit. The imaging unit images a subject injected with blood vessel contrast enhancement particles and diseased tissue contrast enhancement particles. The blood vessel contrast enhancement particles have the first particle size larger than the gap of vascular endothelial cells under the EPR effect. The diseased tissue contrast enhancement particles have the second particle size smaller than the gap. The image generation unit generates a medical image associated with an imaging region of the subject based on output data from the imaging unit. The display unit displays the medical image.

28 Claims, 33 Drawing Sheets

(51) Int. Cl.
*A61B 8/08* (2006.01)
*A61B 5/055* (2006.01)
*A61K 49/00* (2006.01)
*A61B 6/03* (2006.01)
*G01R 33/56* (2006.01)
*A61B 8/00* (2006.01)

(52) U.S. Cl.
CPC .......... *A61K 49/0002* (2013.01); *A61B 6/032* (2013.01); *A61B 6/037* (2013.01); *A61B 6/4241* (2013.01); *A61B 6/4417* (2013.01); *A61B 6/5235* (2013.01); *A61B 8/4416* (2013.01); *G01R 33/5601* (2013.01); *G01R 33/5605* (2013.01)

(56) References Cited

U.S. PATENT DOCUMENTS

| | | | | |
|---|---|---|---|---|
| 2008/0033291 | A1* | 2/2008 | Rousso | A61B 5/02755 600/436 |
| 2011/0054236 | A1* | 3/2011 | Yang | A61K 9/0009 600/9 |
| 2013/0261444 | A1* | 10/2013 | Green | A61N 5/062 600/431 |
| 2015/0133768 | A1* | 5/2015 | McMahon | A61K 49/1812 600/420 |

FOREIGN PATENT DOCUMENTS

| WO | WO 2006/114738 A3 | 11/2006 |
|---|---|---|
| WO | WO 2014/024061 A1 | 2/2014 |

OTHER PUBLICATIONS

Malka Shilo et al. "Nanoparticles as computed tomography contrast agents: current status and future perspectives", Nanomedicine (2012), 7(2), 13 pages.

Office Action dated Mar. 27, 2018 in Japanese Patent Application No. 2014-155351.

* cited by examiner

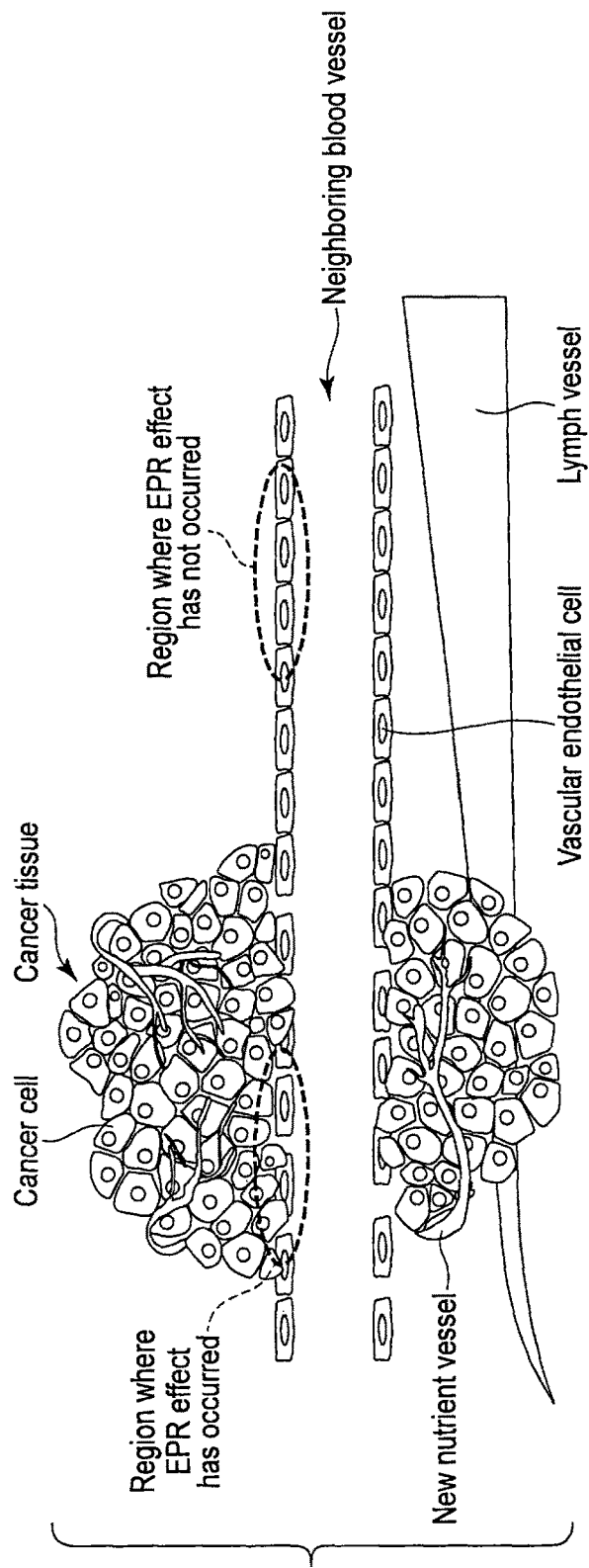
F I G. 1

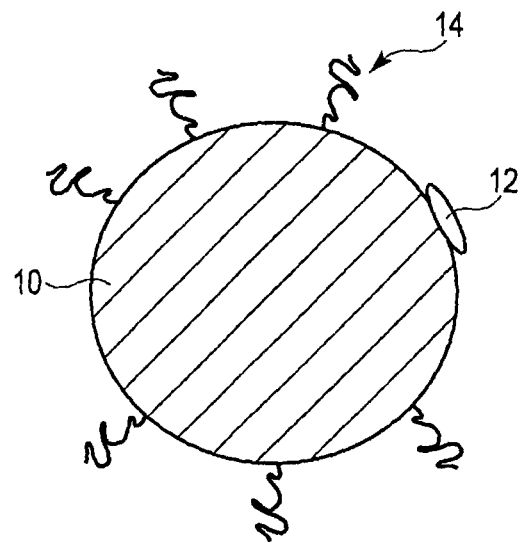
F I G. 6
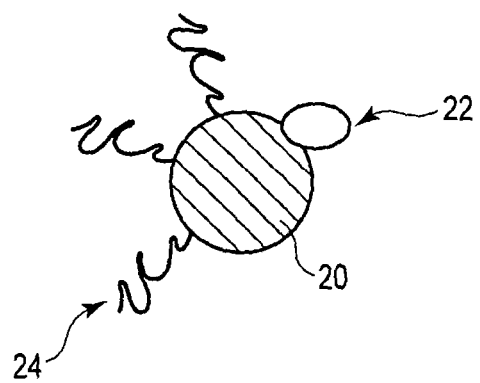
F I G. 7

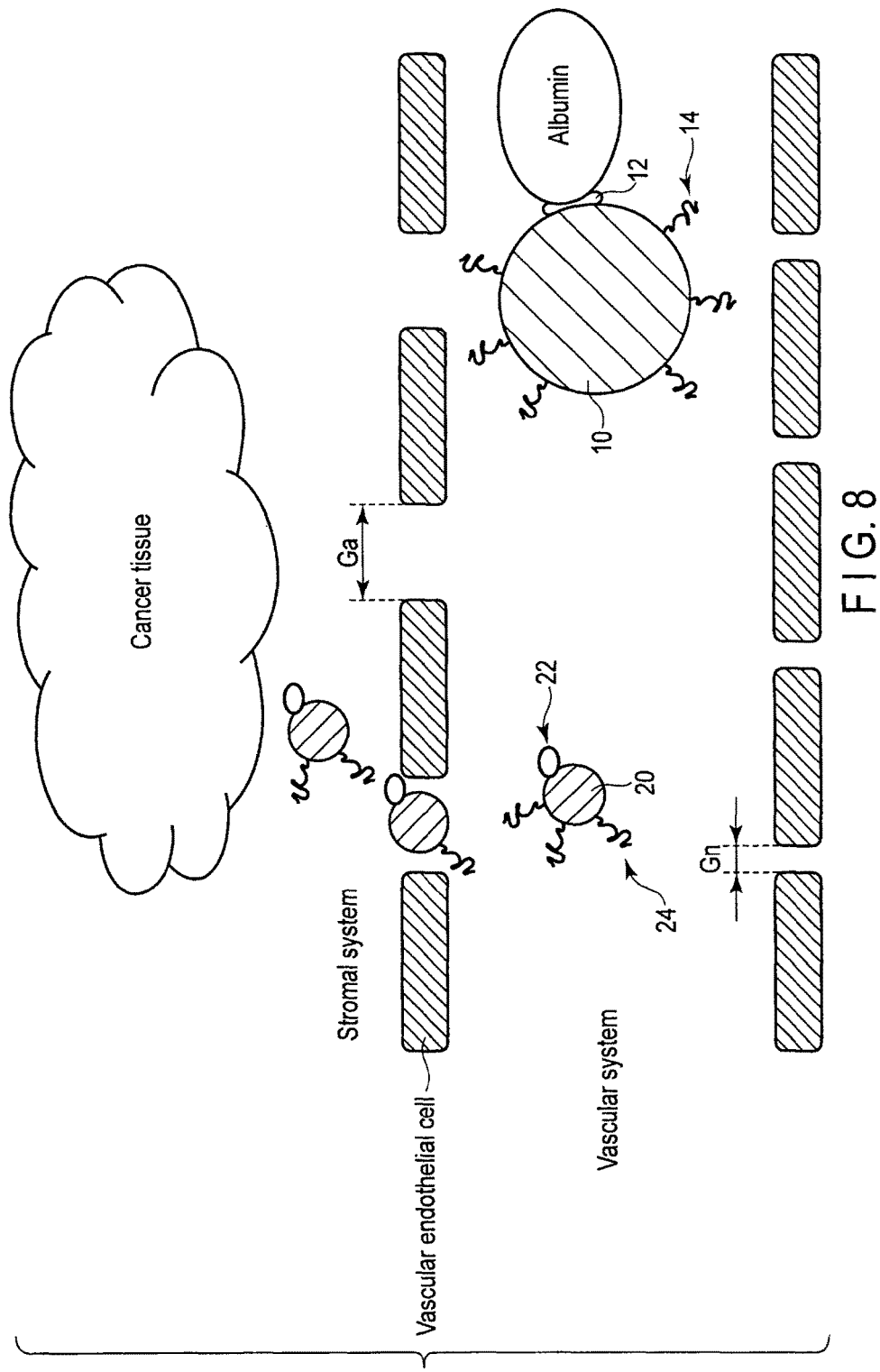
F I G. 8

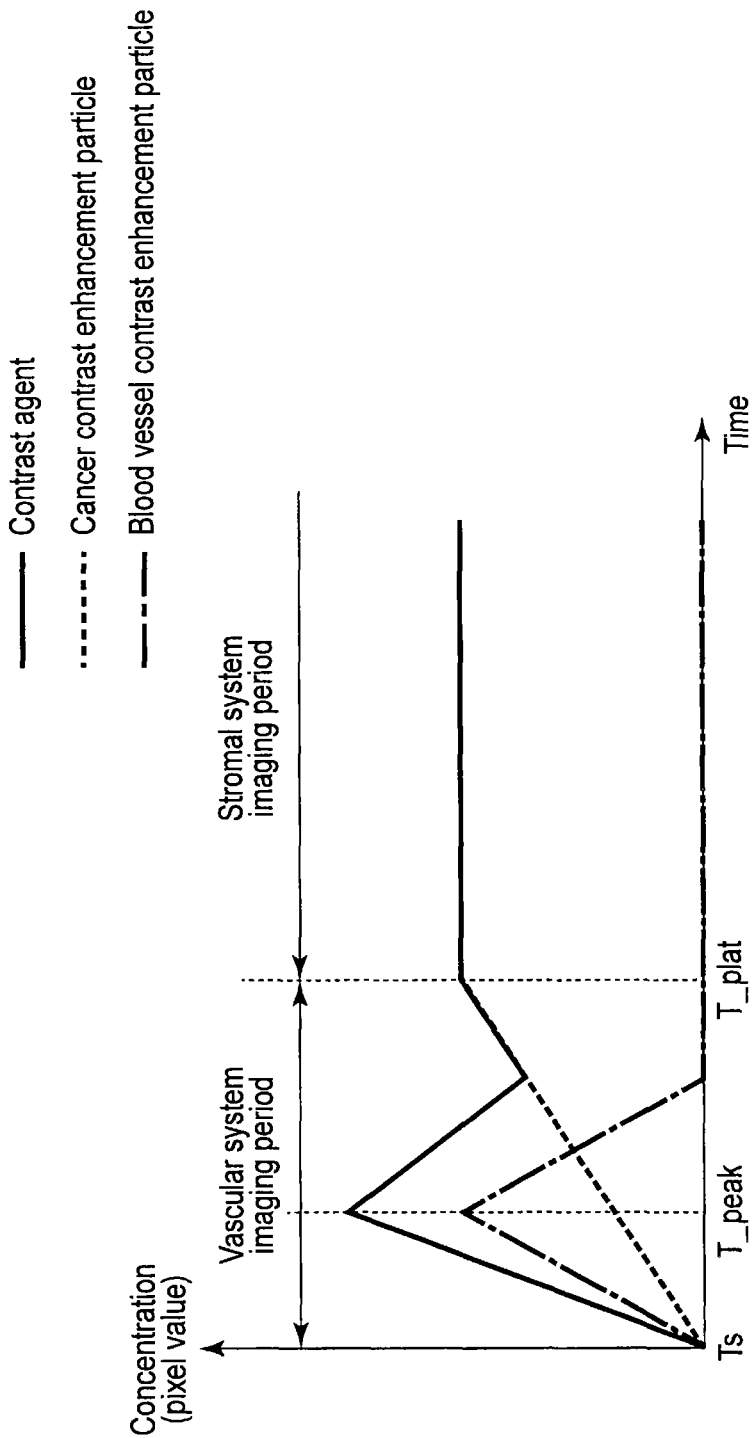
F I G. 14

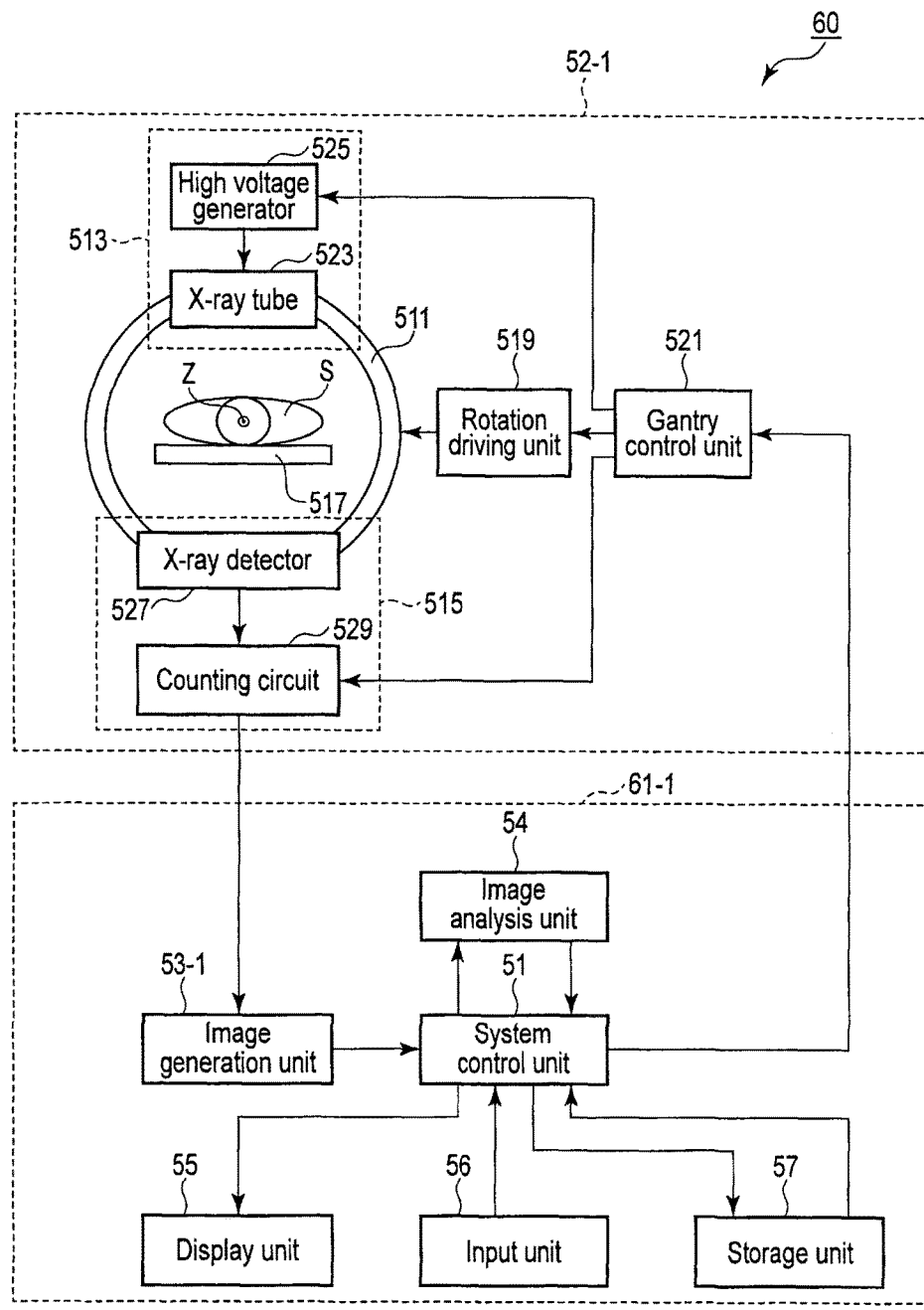
F I G. 17

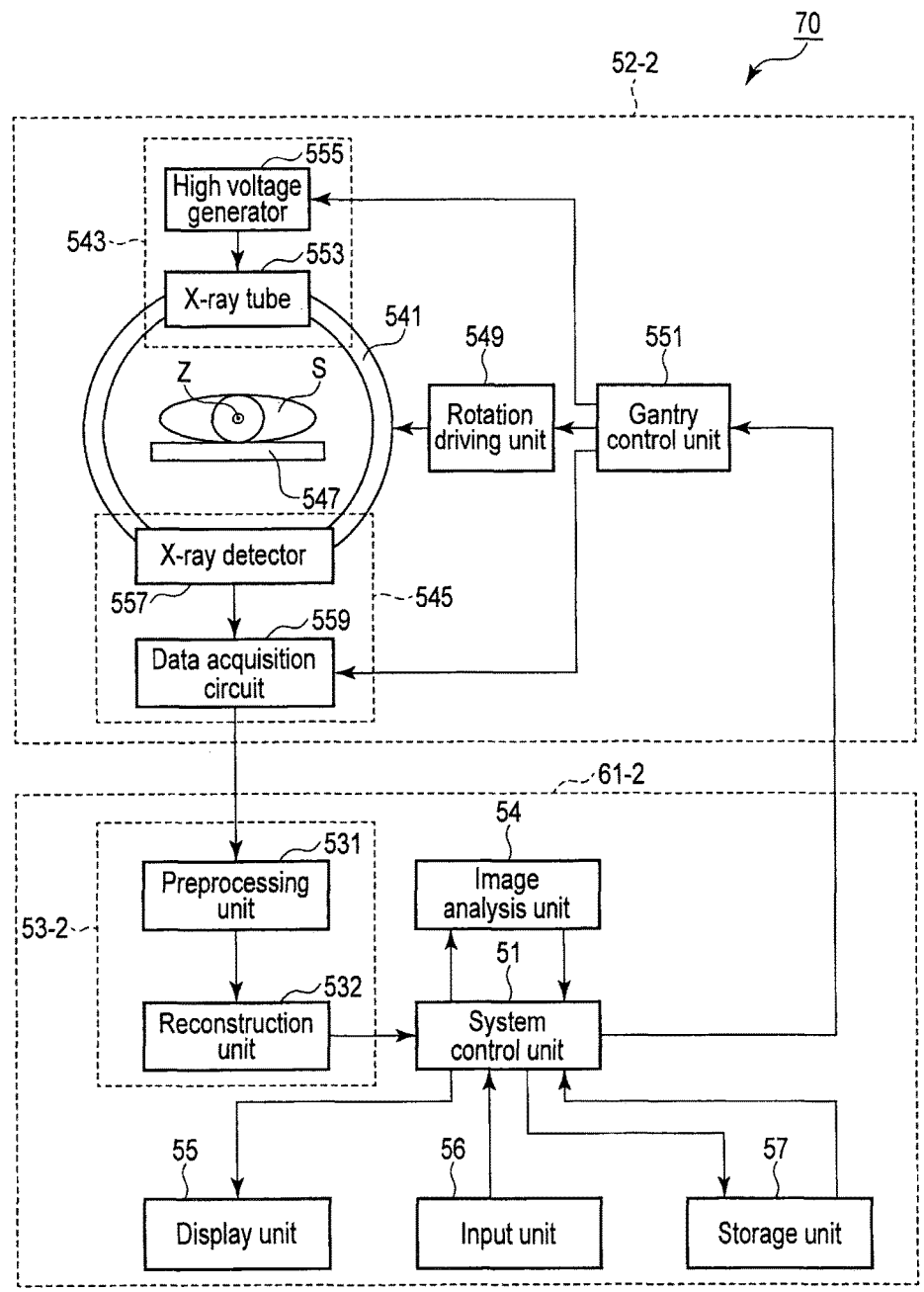
F I G. 20

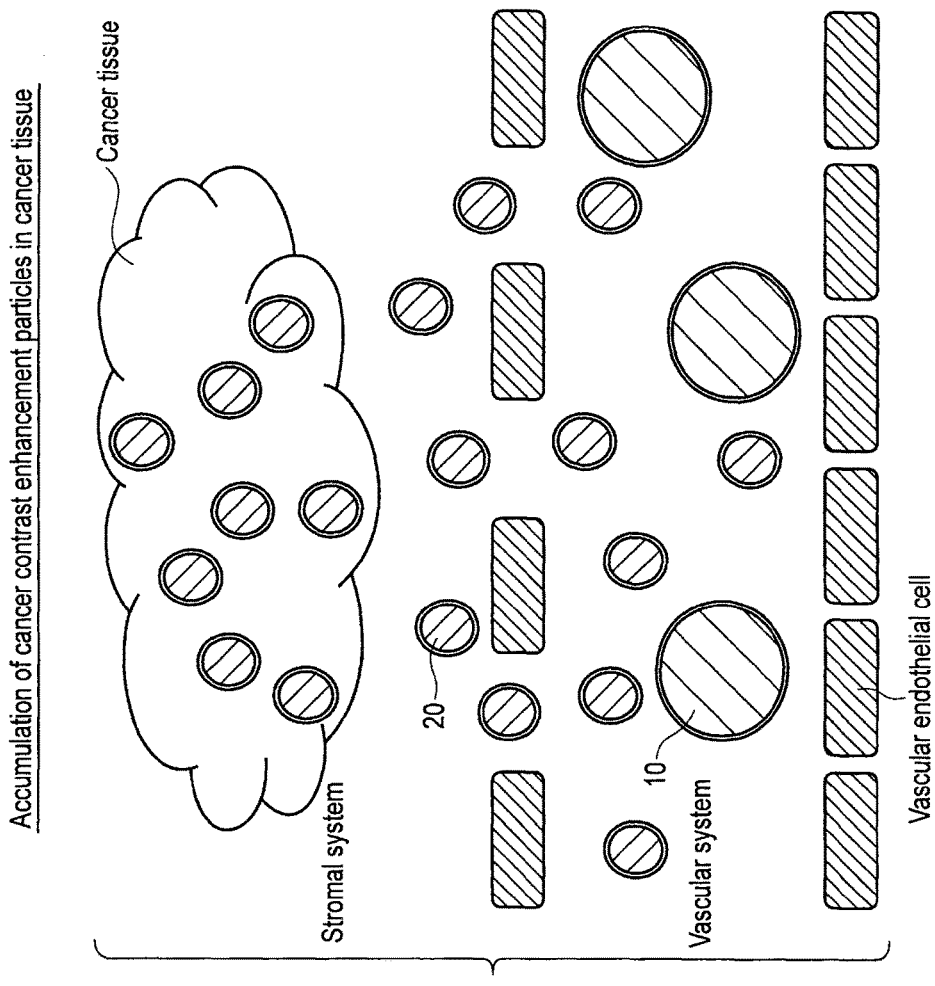
F I G. 24

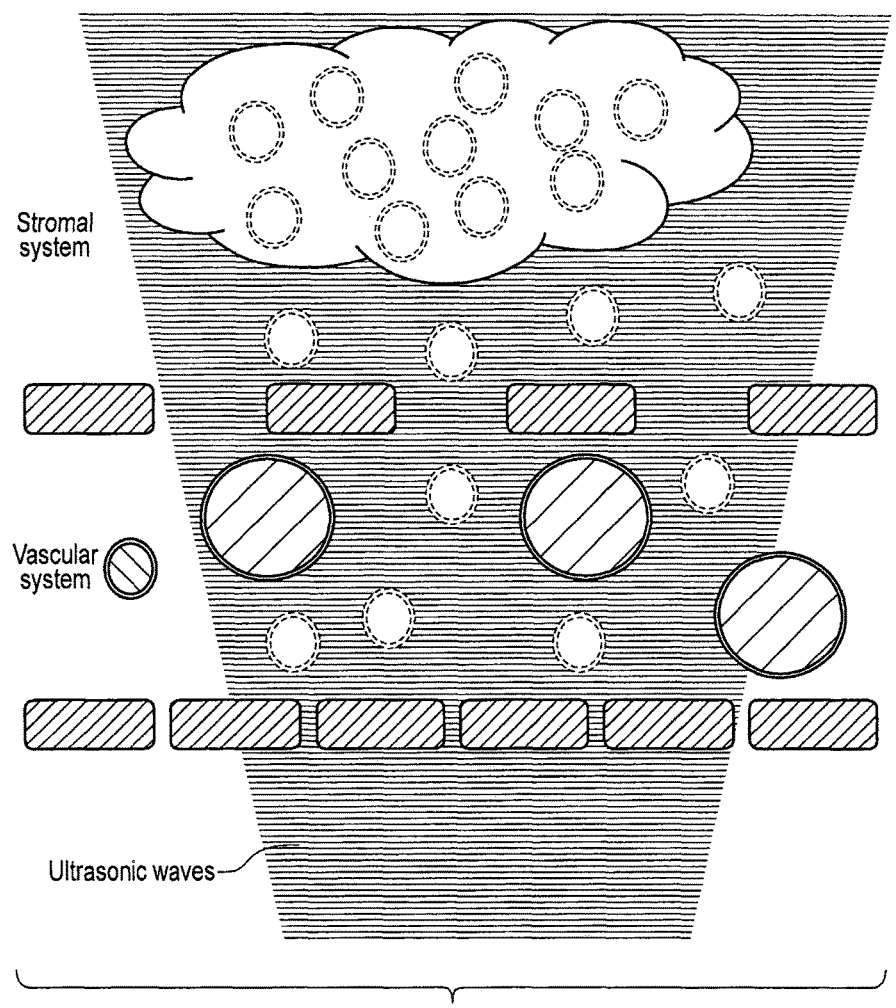
F I G. 25

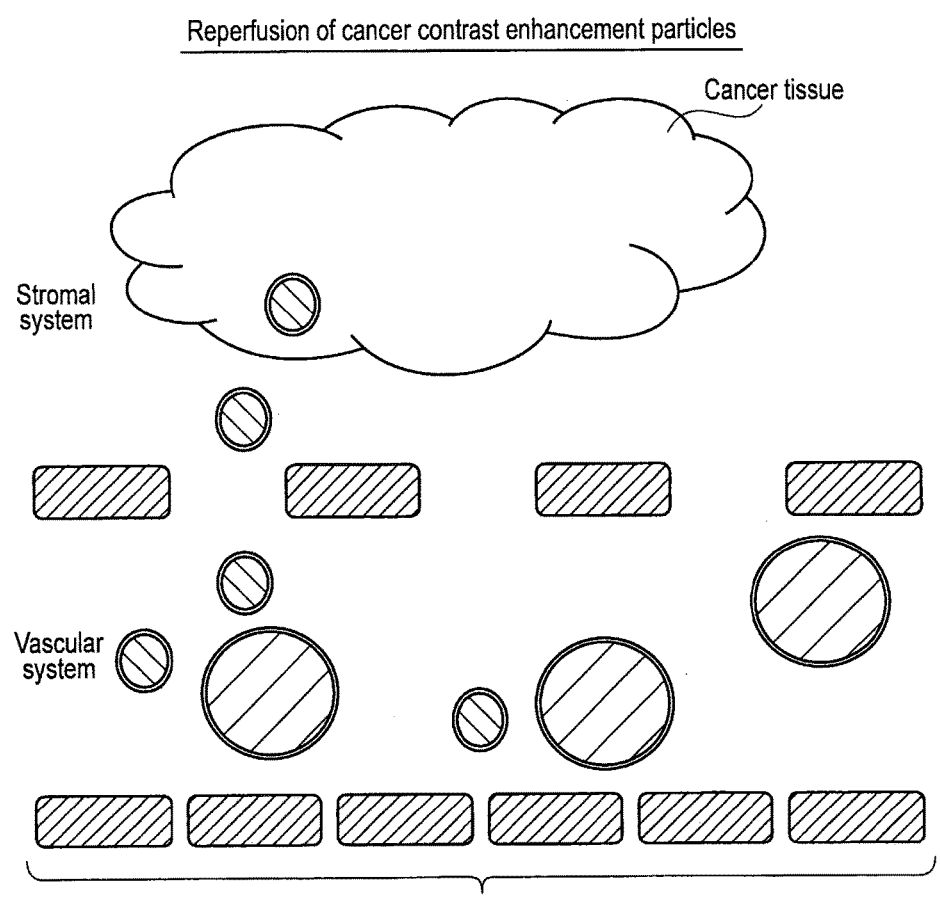
F I G. 26

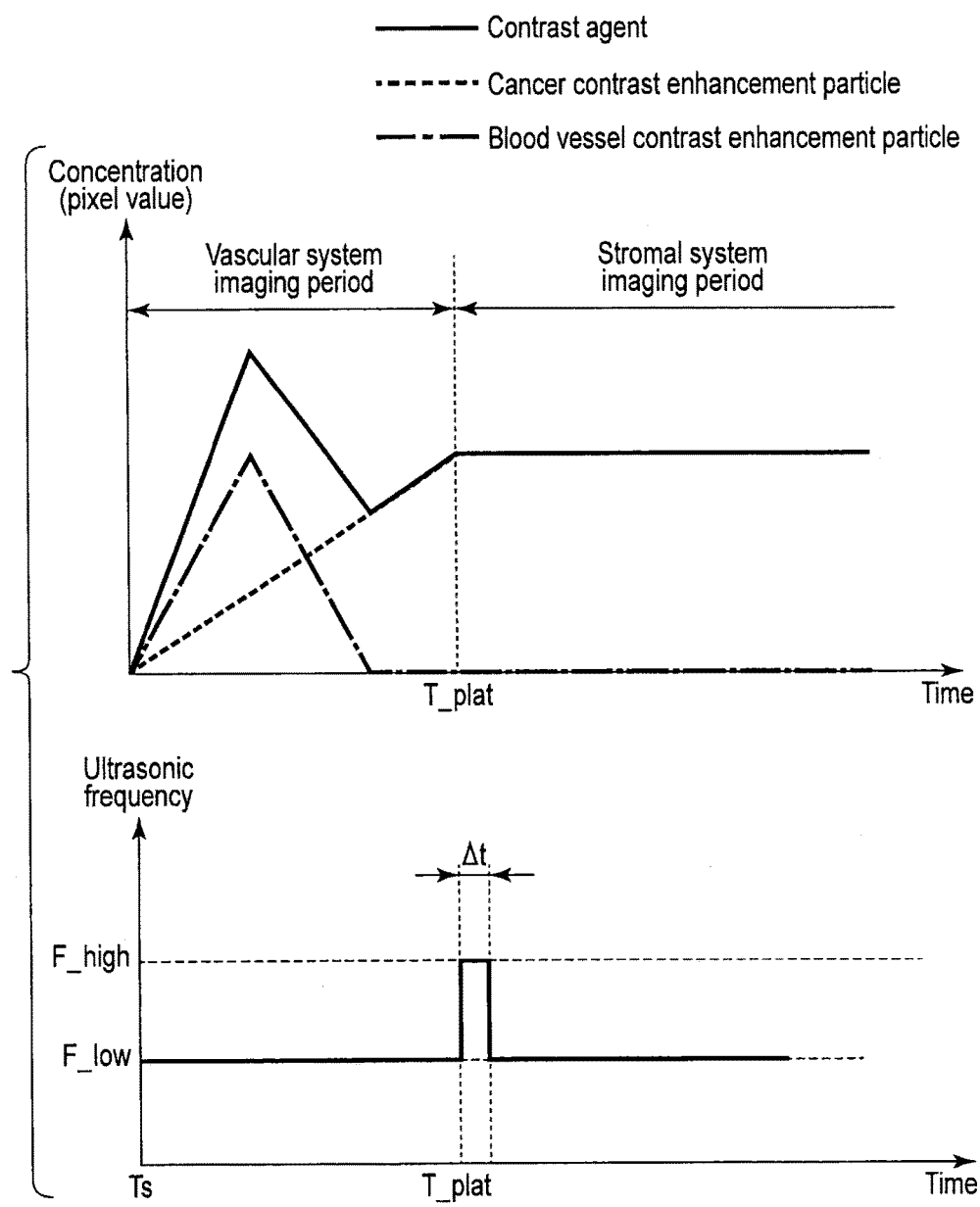
F I G. 28

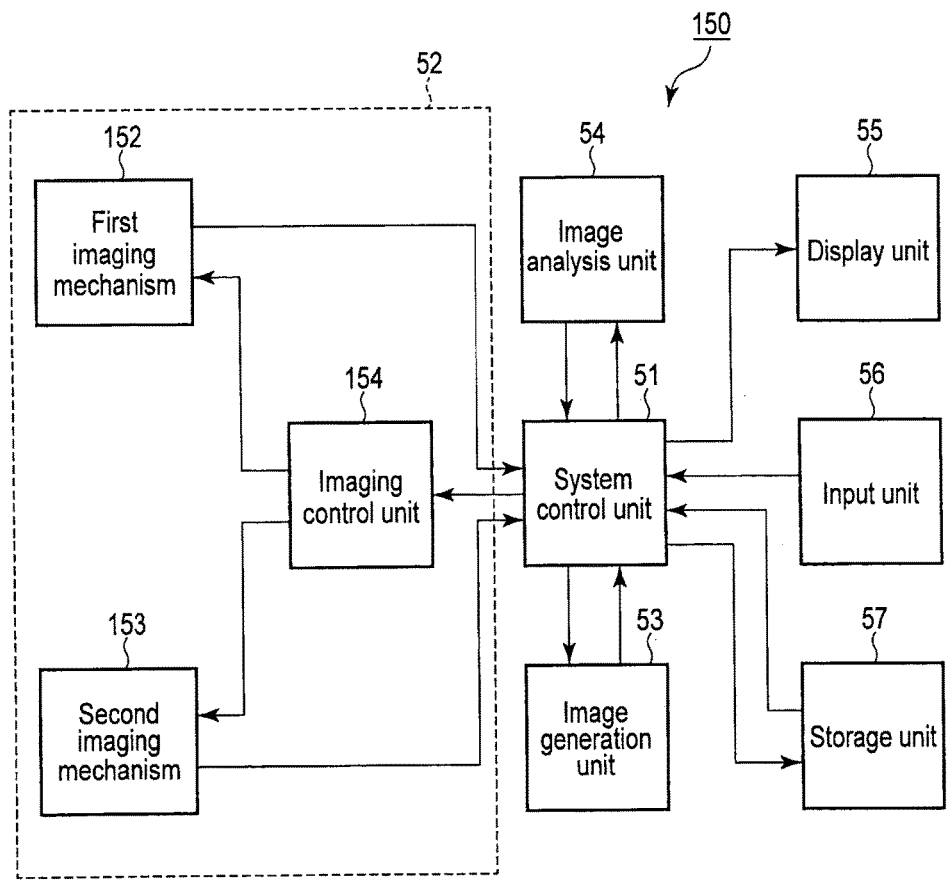
F I G. 30

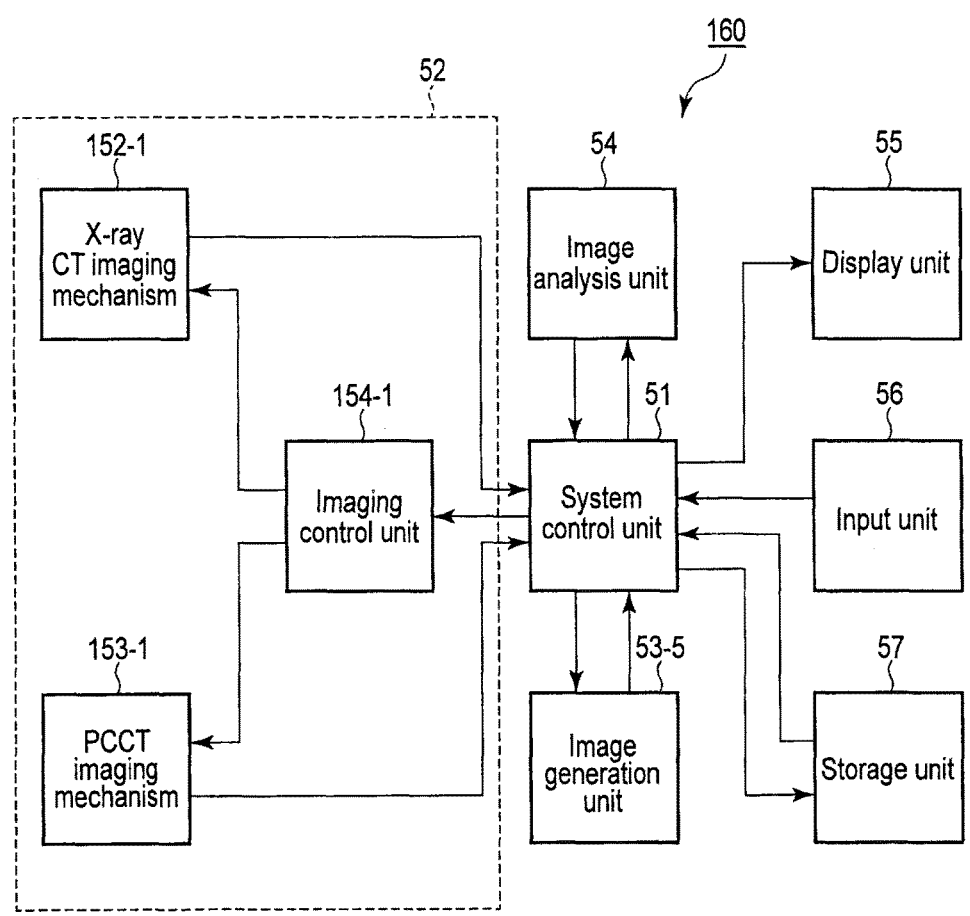
F I G. 31

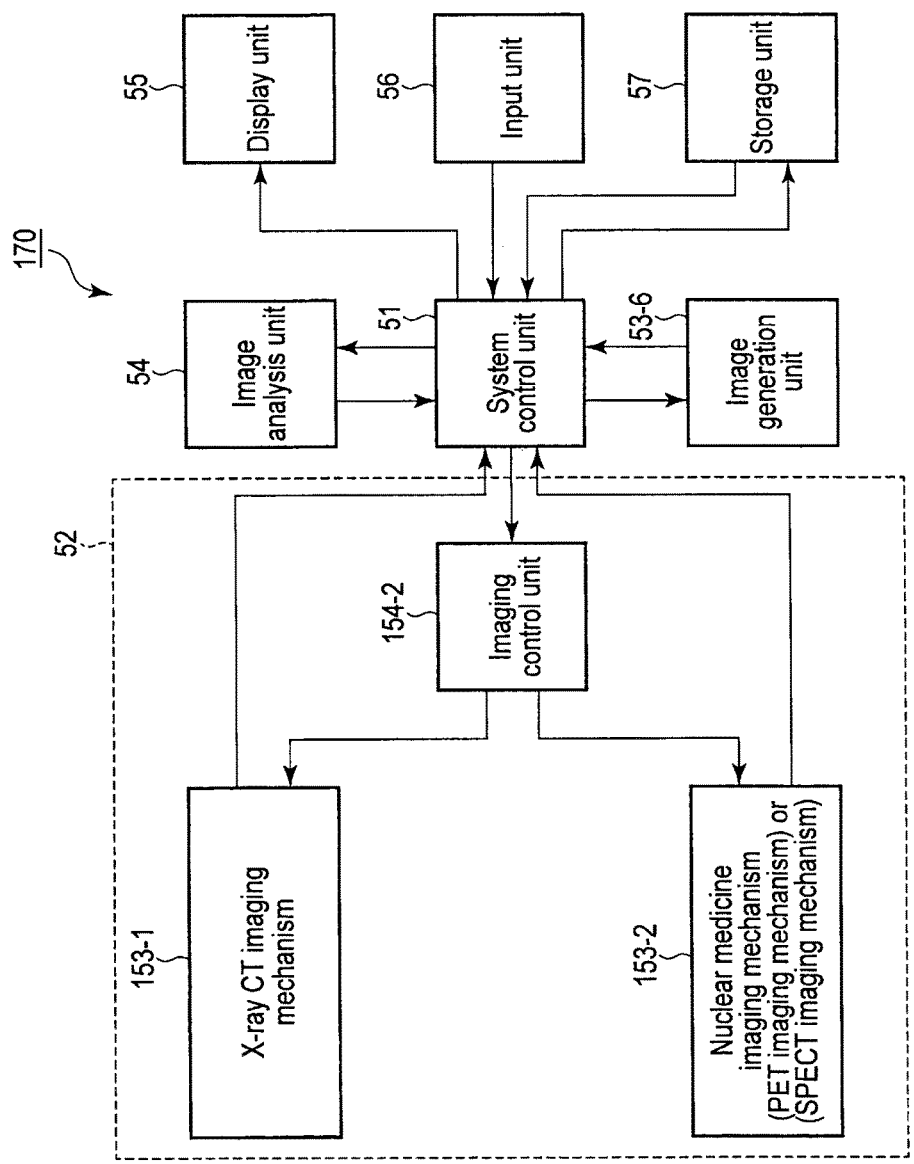
F I G. 34

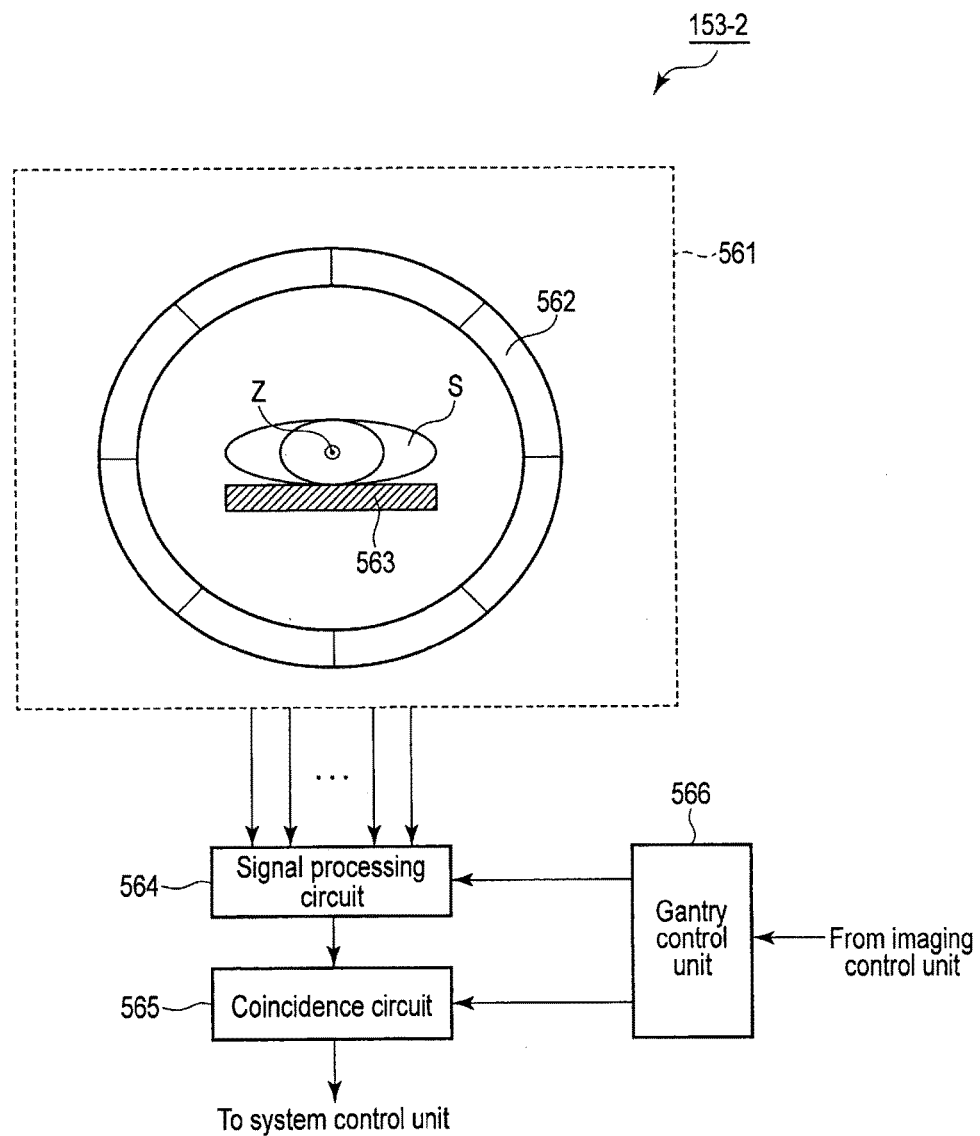
F I G. 35

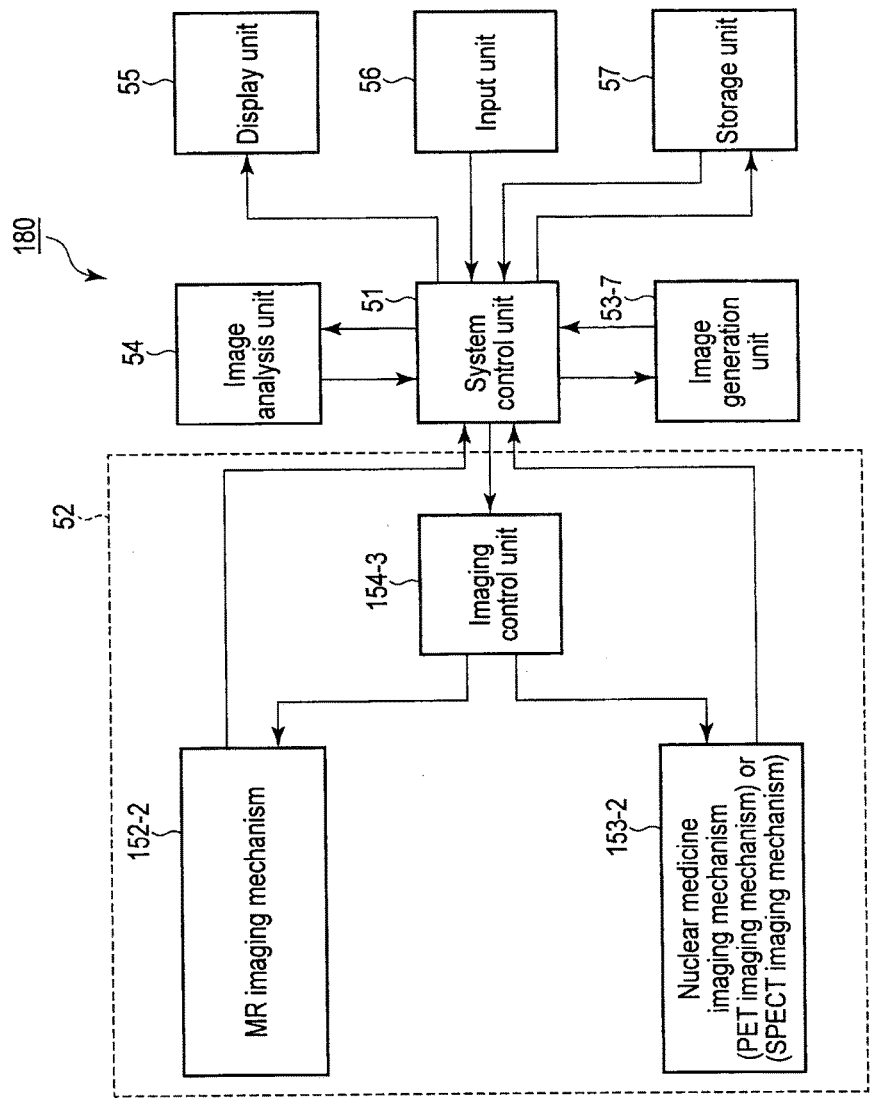
F I G. 36

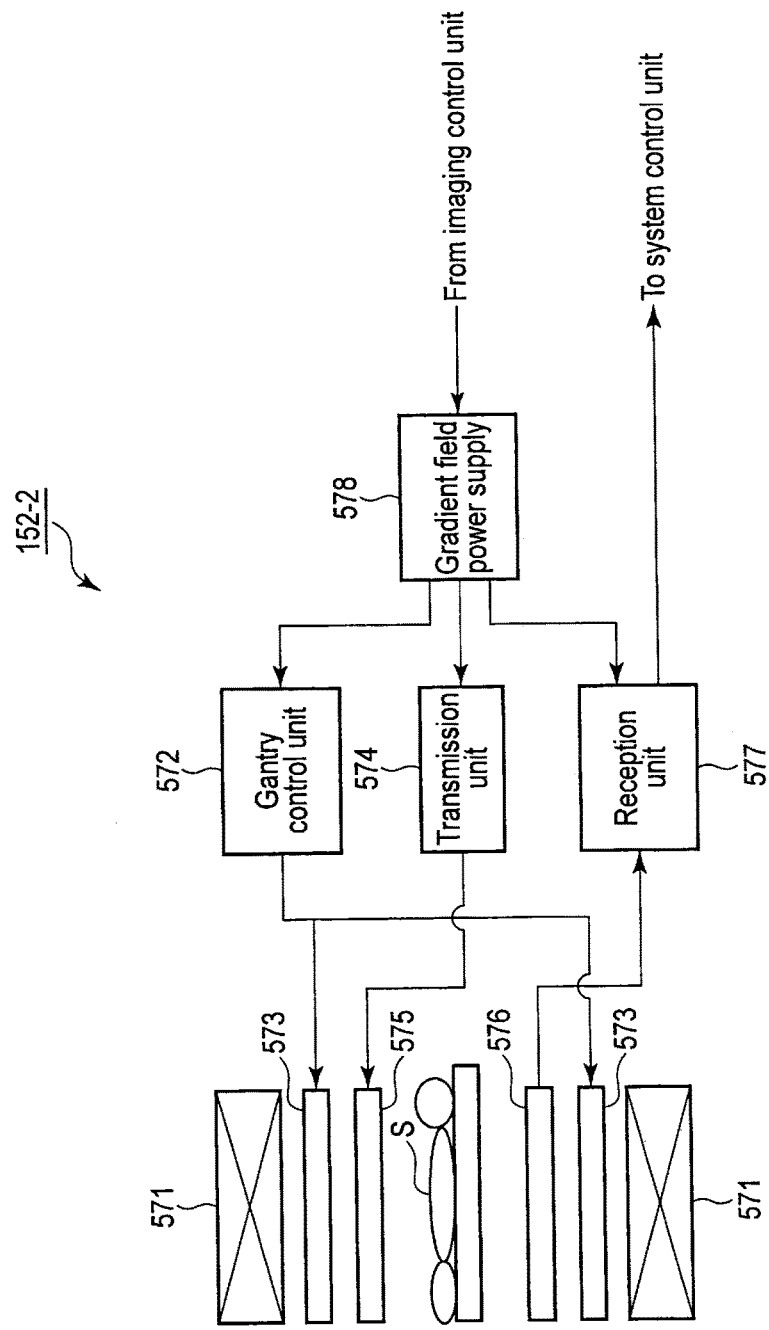
F I G. 37

MEDICAL IMAGE DIAGNOSTIC APPARATUS AND ULTRASONIC DIAGNOSTIC APPARATUS

CROSS-REFERENCE TO RELATED APPLICATIONS

This application is based upon and claims the benefit of priority from the prior Japanese Patent Application No. 2013-159856, filed Jul. 31, 2013 and No. 2013-159857, filed Jul. 31, 2013 the entire contents of all of which are incorporated herein by reference.

FIELD

Embodiments described herein relate generally to a medical image diagnostic apparatus and an ultrasonic diagnostic apparatus.

BACKGROUND

In the field of medical imaging such as PET (positron emission tomography), MRI (magnetic resonance imaging), and ultrasonic imaging, many clinical researches have been made on molecular imaging using nanoparticle contrast agents (see, for example, M. F. Kircher and J. K. Willmann, "Molecular Body Imaging: MR Imaging, CT, and US. Part I. Principles", Radiology, Vol. 263, pp. 633-643, 2012). In addition, clinical researches have been made on molecular imaging using nanoparticles and the like including gold as a heavy metal in PCCT (photon counting CT) called next-generation CT (computed tomography) (see, for example, M. Shilo, et al., "Nanoparticles as computed tomography contrast agents: current status and future perspectives", Nanomedicine, Vol. 7, pp. 257-269, 2012).

The EPR (enhanced permeability and retention) effect occurs in neighboring blood vessels and new nutrient vessels for cancer cells which have progressed to a certain degree. The EPR effect is a phenomenon in which the enhancement of vascular permeability due to the expansion of the gaps between vascular endothelial cells occurs together with the enhancement of the retention of vascular permeability substances due to the undevelopment of a lymphoid system. It is known that vascular endothelial cell gaps are about 5 nm to 50 nm in a normal state, whereas vascular endothelial cell gaps are about 150 nm or more under the EPR effect. In molecular imaging using nanoparticles, imaging is basically performed by using nanoparticles having a single particle size even with slight variations. For this reason, if the particle size is smaller than a vascular endothelial cell gap, it is difficult to image the blood vessel itself, even though it is possible to image the stromal system of a cancer tissue. In contrast to this, if the particle size is larger than a vascular endothelial cell gap, it is difficult to image the stromal system of a cancer tissue, even though it is possible to image the blood vessel itself.

BRIEF DESCRIPTION OF THE DRAWING

FIG. 1 is a view for explaining the EPR effect in a cancer tissue, schematically showing an anatomical structure around the cancer tissue;

FIG. 6 is a view schematically showing an example of a blood vessel contrast enhancement particle according to this embodiment;

FIG. 7 is a view schematically showing an example of a cancer contrast enhancement particle according to this embodiment;

FIG. 8 is a view schematically showing the behaviors of a blood vessel contrast enhancement particle and a cancer contrast enhancement particle which are variously modified at the time of the occurrence of the EPR effect according to this embodiment;

FIG. 14 is a graph showing the time concentration curve of a contrast agent according to this embodiment;

FIG. 17 is a block diagram showing the arrangement of a photon counting CT apparatus according to this embodiment;

FIG. 20 is a block diagram showing the arrangement of an X-ray computed tomography imaging apparatus according to this embodiment;

FIG. 24 is a view schematically showing the behaviors of blood vessel contrast enhancement particles and cancer contrast enhancement particles in the stage of accumulation of cancer contrast enhancement particles in a cancer tissue according to the ultrasonic contrast agent of this embodiment;

FIG. 25 is a view schematically showing the behaviors of blood vessel contrast enhancement particles and cancer contrast enhancement particles in the stage of transmission of a crushing ultrasonic wave according to the ultrasonic contrast agent of this embodiment;

FIG. 26 is a view schematically showing the behaviors of blood vessel contrast enhancement particles and cancer contrast enhancement particles in the stage of accumulation of cancer contrast enhancement particles in a cancer tissue according to the ultrasonic contrast agent of this embodiment;

FIG. 28 is a view showing, side by side, the time concentration curve of a contrast agent according to this embodiment and a temporal change in ultrasonic frequency;

FIG. 30 is a block diagram showing the arrangement of a composite type medical image diagnostic apparatus according to this embodiment;

FIG. 31 is a block diagram showing the arrangement of a PCCT/CT apparatus according to this embodiment;

FIG. 34 is a block diagram showing the arrangement of a nuclear medicine imaging/CT apparatus according to this embodiment;

FIG. 35 is a block diagram showing the arrangement of a nuclear medicine imaging mechanism (PET imaging mechanism) in FIG. 34;

FIG. 36 is a block diagram showing the arrangement of a nuclear medicine imaging/MRI apparatus according to this embodiment; and FIG. 37 is a block diagram showing the arrangement of a magnetic resonance diagnostic apparatus (MRI apparatus) in FIG. 36.

DETAILED DESCRIPTION

A medical image diagnostic apparatus according to an embodiment includes an imaging unit, an image generation unit, and a display unit. The imaging unit images a subject injected with blood vessel contrast enhancement particles for enhancing the contrast of a blood vessel and diseased tissue contrast enhancement particles for enhancing the contrast of a diseased tissue. The blood vessel contrast enhancement particles have the first particle size larger than the gap of vascular endothelial cells under the EPR effect. The diseased tissue contrast enhancement particles have the second particle size smaller than the gap. The image generation unit generates a medical image associated with an imaging region of the subject based on output data from the imaging unit. The display unit displays the medical image.

The medical image diagnostic apparatus according to this embodiment will be described below with reference to the accompanying drawing.

The medical image diagnostic apparatus according to this embodiment executes medical imaging using a contrast agent according to the embodiment.

The contrast agent according to this embodiment will be described first. The contrast agent according to the embodiment has the property capable of individually targeting the vascular system and stromal system of a diseased tissue. A diseased tissue whose contrast is to be enhanced by the contrast agent according to the embodiment may be any type of diseased tissue in which the EPR effect occurs in a neighboring blood vessel and a new nutrient vessel with the progress of the lesion. In addition, a diseased tissue may be an inflammatory reaction tissue like a tissue exhibiting the EPR effect, in which immune cells like granulocytes discharge cytokines to neighboring vascular endothelial cells to reduce their volumes in the early development of inflammation, and as a result, the gaps between vascular endothelial cells increase, leading to the accentuation of vascular permeability. For the sake of a concrete description to be made below, assume that a diseased tissue is a cancer tissue.

The EPR effect in a cancer tissue will be described below with reference to FIG. 1. FIG. 1 is a view schematically showing an anatomical structure around a cancer tissue. As shown in FIG. 1, the cancer tissue includes a plurality of cancer cells and receives nutrients from a neighboring blood vessel and a new nutrient vessel. The gaps between a plurality of cancer cells are filled with an interstitial fluid (not shown). A blood vessel wall includes a plurality of vascular endothelial cells. Gaps are provided between vascular endothelial cells, and nutrient components and the like flowing in the blood vessel pass through the gaps and are supplied to cancer cells and the like through interstitial fluid. The gaps between vascular endothelial cells will be referred to as vascular endothelial cell gaps hereinafter.

Figure 2:
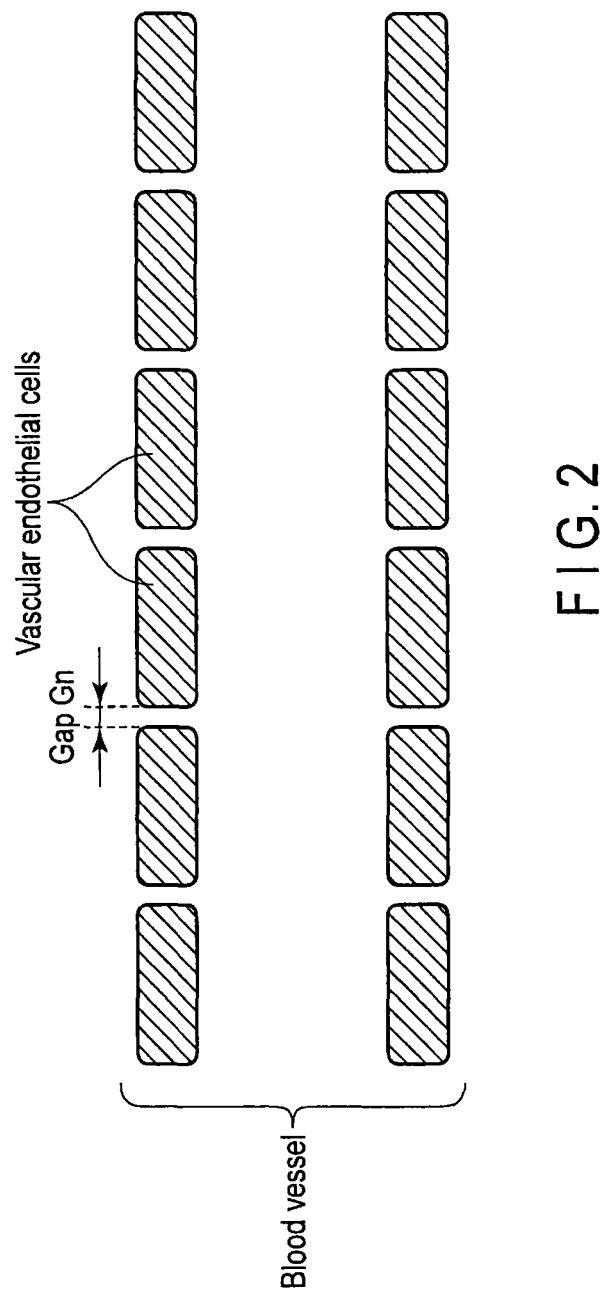
FIG. 2 is a view schematically showing the anatomical structure of a vascular system including a region where no EPR effect has occurred in FIG. 1.
Figure 3:
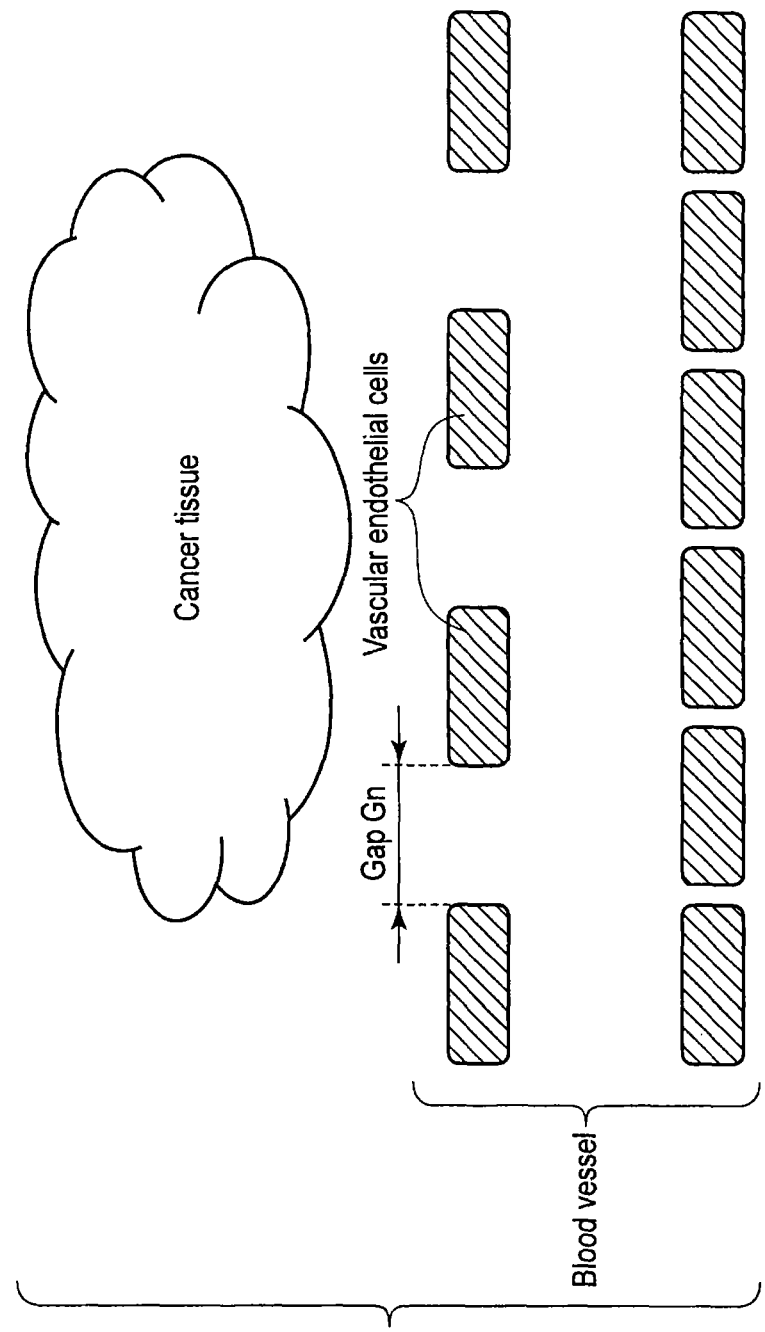
FIG. 3 is a view schematically showing the anatomical structure of a vascular system including a region where the EPR effect has occurred in FIG. 1.

With the progress of cancer, the EPR effect occurs in a neighboring blood vessel or new nutrient vessel for cancer cells. FIG. 2 is a view schematically showing the anatomical structure of a vascular system of a region where no EPR effect has occurred. FIG. 3 is a view schematically showing the anatomical structure of a vascular system of a region where the EPR effect has occurred. As shown in FIGS. 2 and 3, with the progress of cancer, the vascular endothelial cells contract, and the vascular endothelial cell gaps expand. As shown in FIG. 2, a vascular endothelial cell gap Gn in a normal state is typically about 5 nm to 50 nm. As shown in FIG. 3, however, a vascular endothelial cell gap Ga of a blood vessel in which the EPR effect has occurred is larger than the vascular endothelial cell gap Gn in a normal state and expands to about 150 nm or more.

As a conventional contrast agent, contrast enhancement particles having a single particle size are basically used. If contrast enhancement particles having a particle size smaller than a vascular endothelial cell gap are used to image the stromal system of a cancer tissue, since the contrast enhancement particles pass through the vascular endothelial cell gaps and reach the cancer tissue through the interstitial fluid, it is possible to clearly enhance the contrast of the stromal system of the cancer tissue. However, the contrast enhancement effect provided for the blood vessel by the contrast enhancement particles is weakened. In contrast to this, if contrast enhancement particles having a particle size larger than a vascular endothelial cell gap are used to image the vascular system, it is difficult for the contrast enhancement particles to pass through the vascular endothelial cell gaps. This weakens the contrast enhancement effect for the stromal system of the cancer tissue, although it is possible to clearly enhance the contrast of the blood vessel. Note that contrast enhancement particles are nanoparticles having a contrast enhancement effect in the imaging principle of a medical image diagnostic apparatus used for imaging with the contrast agent. The contrast enhancement effect indicates the property capable of producing a clear contrast between the contrast agent portion and the non-contrast-agent portion on the medical image acquired by a medical image diagnostic apparatus when the contrast agent is imaged by the medical image diagnostic apparatus according to a given imaging principle.

The contrast agent according this embodiment has the property capable of individually targeting the vascular system and stromal system of a cancer tissue. That is, the contrast agent according to the embodiment contains a plurality of contrast enhancement particles for enhancing the contrast of a blood vessel and a plurality of contrast enhancement particles for enhancing the contrast of a cancer tissue. In the following description, contrast enhancement particles for enhancing the contrast of a blood vessel will be referred to as blood vessel contrast enhancement particles, and contrast enhancement particles for enhancing the contrast of a cancer tissue will be referred to as cancer contrast enhancement particles.

Figure 4:
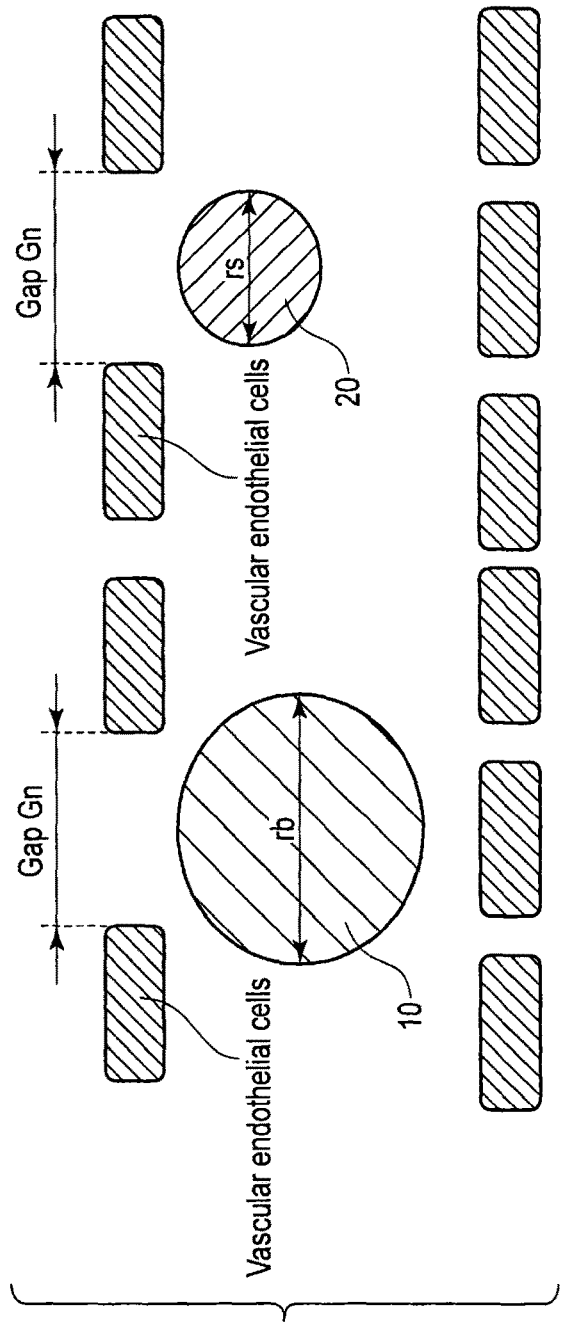
FIG. 4 is a view schematically showing an example of a blood vessel contrast enhancement particle and a cancer contrast enhancement particle according to an embodiment.

FIG. 4 is a view schematically showing an example of a blood vessel contrast enhancement particle 10 and a cancer contrast enhancement particle 20. As shown in FIG. 4, the blood vessel contrast enhancement particle 10 is formed to have a particle size larger than the vascular endothelial cell gap Ga of an imaging target blood vessel in which the EPR effect has occurred. The cancer contrast enhancement particle 20 is formed to have a particle size smaller than the gap Ga of the imaging target blood vessel in which the EPR effect has occurred.

The particle sizes of the blood vessel contrast enhancement particle 10 and cancer contrast enhancement particle 20 will be described in more detail. The blood vessel contrast enhancement particle 10 and the cancer contrast enhancement particle 20 are simultaneously injected into a vein of a subject. The vascular endothelial cell gaps of a blood vessel in which the EPR effect has occurred are typically 150 nm or more. Therefore, the particle size of the blood vessel contrast enhancement particle 10 needs to be at least 150 nm or more to prevent the particle from passing through the vascular endothelial cell gap of the blood vessel at the time of the occurrence of the EPR effect. The particle size of the blood vessel contrast enhancement particle 10 is preferably 200 nm or more, more preferably, 300 nm or more to reliably prevent the particle from passing through the vascular endothelial cell gap at the time of the occurrence of the EPR effect. Setting the particle size of the blood vessel contrast enhancement particle 10 in this manner can make the blood vessel contrast enhancement particle 10 retain in the blood vessel without passing through the vascular endothelial cell gap even at the time of the occurrence of the EPR effect.

On the other hand, the cancer contrast enhancement particle 20 is formed to have a particle size equal to or less than 150 nm at most so as to allow the particle to pass through the vascular endothelial cell gap at the time of the occurrence of the EPR effect. Macrophages as phagocytes exist in an RES (Reticulo-Endothelial System) of the liver, spleen, or the like. Macrophages are cells which phagocyte foreign substances. In general, contrast enhancement particles circulate in the body. In order to prevent the cancer contrast enhancement particle 20 passing through the vascular endothelial cell gap from being phagocyted by the above macrophages, the cancer contrast enhancement particle 20 is preferably formed to have a particle size equal to or less than 100 nm. Setting the particle size of the cancer contrast enhancement particle 20 in this manner can more reliably accumulate the cancer contrast enhancement particle 20 in the cancer tissue. Note that when making the cancer contrast enhancement particle 20 pass through the vascular endothelial cell gap only at the time of the occurrence of the EPR effect, the cancer contrast enhancement particle 20 is preferably formed to have a particle size equal to or more than 50 nm.

Figure 5:
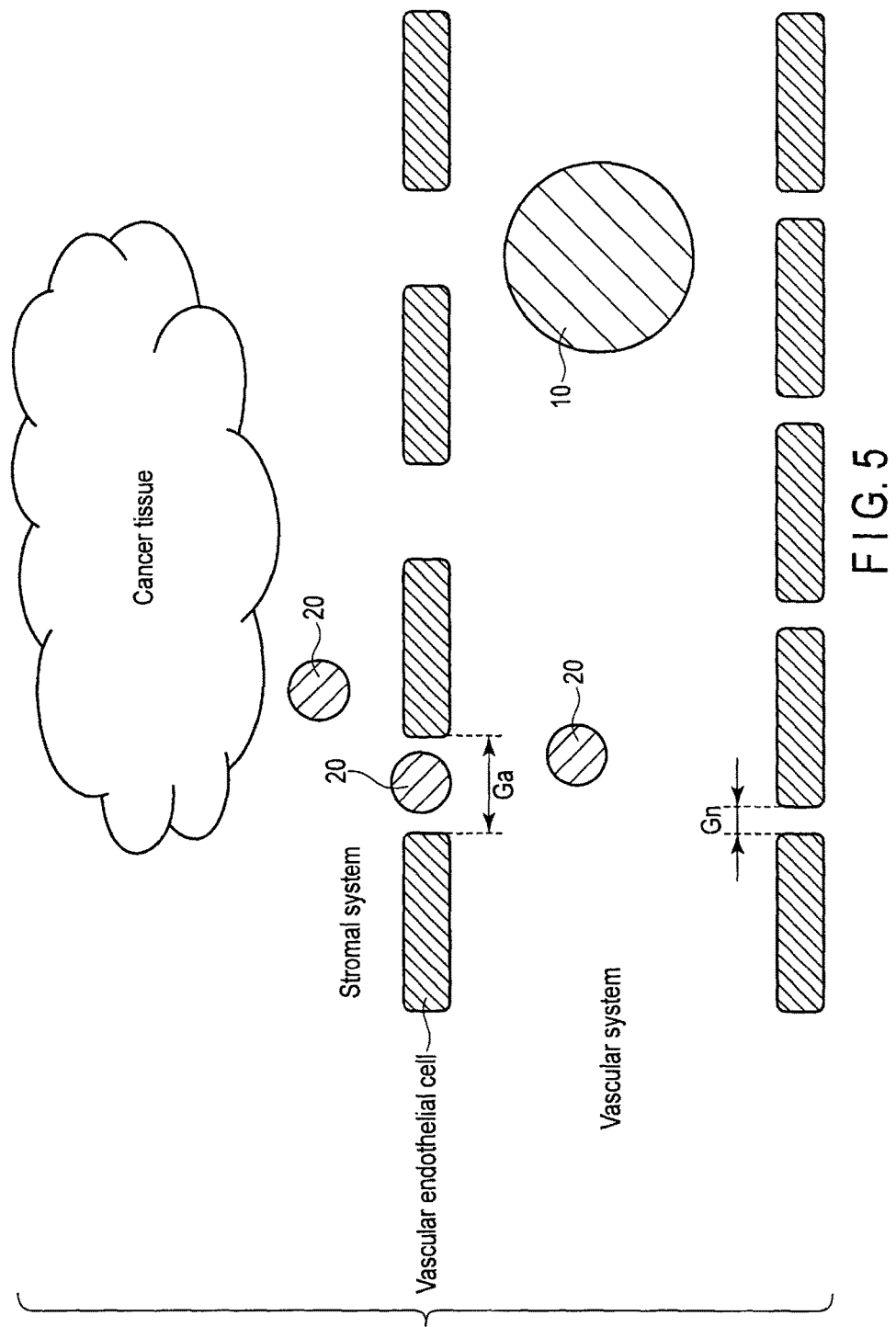
FIG. 5 is a view schematically showing the behaviors of a blood vessel contrast enhancement particle and a cancer contrast enhancement particle at the time of the occurrence of the EPR effect according to this embodiment.

FIG. 5 is a view schematically showing the behaviors of the blood vessel contrast enhancement particle 10 and cancer contrast enhancement particle 20 at the time of the occurrence of the EPR effect. As shown in FIG. 5, the blood vessel contrast enhancement particle 10 and the cancer contrast enhancement particle 20 are individually set in accordance with the standard value of the vascular endothelial cell gap Ga at the time of the occurrence of the EPR effect such that the blood vessel contrast enhancement particle 10 is retained in the blood vessel at the time of the occurrence of the EPR effect, and the cancer contrast enhancement particle 20 is accumulated in the cancer tissue at the time of the occurrence of the EPR effect. Vascular endothelial cell gaps vary depending on the anatomical region in which a blood vessel exists as well as the presence/absence of the EPR effect and the degree of progress of a lesion. Therefore, the particle sizes of the blood vessel contrast enhancement particle 10 and cancer contrast enhancement particle 20 may be decided in accordance with the standard value of the gap Ga for each anatomical region. This makes it possible to individually target the vascular system and stromal system of a cancer tissue independently of an imaging target region. Note that the standard value of the gap Ga for each anatomical region may be determined experimentally and empirically.

Various modifications are preferably provided for the blood vessel contrast enhancement particle 10 and the cancer contrast enhancement particle 20. The modifications provided for the blood vessel contrast enhancement particle 10 and the cancer contrast enhancement particle 20 will be described below.

FIG. 6 is a view schematically showing an example of the blood vessel contrast enhancement particle 10. As shown in FIG. 6, the surface of the blood vessel contrast enhancement particle 10 is chemically modified with a functional group 12 which can be bonded to albumin existing in blood. The functional group 12 which can be bonded to albumin existing in blood includes, for example, carbonyl, ether, amide, and amine. If the blood vessel contrast enhancement particle 10 is not bonded to albumin existing in blood of the subject, the blood vessel contrast enhancement particle 10 is discharged from the blood vessel by the kidney. For this reason, the blood vessel contrast enhancement particle 10 cannot be retained in the blood vessel for a long period of time. If the blood vessel contrast enhancement particle 10 is bonded to albumin through the functional group 12, the blood vessel contrast enhancement particle 10 is suppressed from being discharged from the blood vessel by the kidney. This allows the blood vessel contrast enhancement particle 10 to be retained in the blood vessel for a long period of time. That is, it is possible to use the blood vessel contrast enhancement particle 10 as a blood pool agent.

FIG. 7 is a view schematically showing an example of the cancer contrast enhancement particle 20. As shown in FIG. 7, a specific ligand 22 is bonded to the surface of the cancer contrast enhancement particle 20. The ligand 22 has the property of specifically adsorbing a specific protein (receptor) existing on the surface of a cancer cell or in the cancer cell. The type of ligand 22 is changed in accordance with the characteristics of a cancer cell of an organ as a contrast enhancement target. As the ligand 22, for example, an EGF (epidermal growth factor) or a VEGF (vascular endothelial growth factor) is used. Providing the ligand 22 in accordance with the characteristics of a cancer cell of an organ as a contrast enhancement target in this manner can specifically accumulate the cancer contrast enhancement particle 20 in the cancer tissue.

In addition, as shown in FIGS. 6 and 7, PEGs (polyethylene glycols) 14 and 24 are preferably formed on the surfaces of the blood vessel contrast enhancement particle 10 and cancer contrast enhancement particle 20 by chemical modification. The PEGs 14 and 24 prevent the blood vessel contrast enhancement particle 10 and the cancer contrast enhancement particle 20 from being bonded to the surface proteins of vascular endothelial cells. The PEGs 14 and 24 need not always be chemically modified on both the blood vessel contrast enhancement particle 10 and the cancer contrast enhancement particle 20 and may be chemically modified on only one of them.

FIG. 8 is a view schematically showing the behaviors of the blood vessel contrast enhancement particle 10 and cancer contrast enhancement particle 20 provided with various modifications described above at the time of the occurrence of the EPR effect. As shown in FIG. 8, the blood vessel contrast enhancement particle 10 chemically modified with the PEG 14 and the cancer contrast enhancement particle 20 chemically modified with the PEG 24 can flow in the blood vessel for a long period of time without being bonded to surface proteins of vascular endothelial cells. Albumin existing in the blood vessel is bonded to the functional group 12 of the blood vessel contrast enhancement particle 10. The blood vessel contrast enhancement particle 10 to which the albumin is bonded is suppressed from being discharged from the blood vessel by the kidney, and can be retained in the blood vessel for a long period of time. In addition, chemically modifying the blood vessel contrast enhancement particle 10 with the PEG 14 can improve the fluidity of the blood vessel contrast enhancement particle 10 in the blood vessel. Furthermore, the ligand 22 of the cancer contrast enhancement particle 20 passing through the vascular endothelial cell gap Ga is specifically bonded to the receptor of a cancer cell. This makes it possible to specifically accumulate the cancer contrast enhancement particle 20 in the cancer cell. In addition, chemically modifying the cancer contrast enhancement particle 20 with the PEG 24 can synergistically increase the amount of cancer contrast enhancement particles 20 accumulated in the cancer tissue.

Human blood includes blood cells and blood plasma. Blood cells include erythrocytes, leukocytes, and platelets. Erythrocytes occupy most of the volume of blood cells. In general, a erythrocyte has a diameter of several µm, and a leukocyte has a diameter of ten several µm. As described above, the diameter of the cancer contrast enhancement particle 20 is much smaller than those of a erythrocyte and leukocyte, and the diameter of the blood vessel contrast enhancement particle 10 is between that of the cancer contrast enhancement particle 20 and those of a erythrocyte and a leukocyte. If only the cancer contrast enhancement particles 20 are injected into the subject, the cancer contrast enhancement particles 20 are pushed back by blood cells such as erythrocytes and hence are difficult to pass through the vascular endothelial cell gaps. In contrast, when both the blood vessel contrast enhancement particles 10 and the cancer contrast enhancement particles 20 are injected into the subject, the cancer contrast enhancement particles 20 can pass through the vascular endothelial cell gaps more efficiently, owing to a hydrodynamic effect, than when the blood vessel contrast enhancement particles 10 are not injected. Therefore, making the contrast agent according to this embodiment contain both the blood vessel contrast enhancement particles 10 and the cancer contrast enhancement particles 20 will improve the linearity between the amount of cancer contrast enhancement particles 20 injected into the blood vessel and the amount of cancer contrast enhancement particles 20 passing through the vascular endothelial cell gaps as compared with a case in which the contrast agent contains only the cancer contrast enhancement particles 20. In other words, the quantitativeness of the contrast enhancement effect of the stromal system by the cancer contrast enhancement particle 20 improves.

In addition, the blood vessel contrast enhancement particle 10 and the cancer contrast enhancement particle 20 may respectively contain materials having different contrast enhancement effects in the imaging principle of a medical image diagnostic apparatus to be used for imaging of the contrast agent according to this embodiment. Materials exhibiting dominant contrast enhancement effects in the respective contrast enhancement particles 10 and 20 will be referred to as contrast enhancement materials hereinafter. Since the blood vessel contrast enhancement particle 10 and the cancer contrast enhancement particle 20 respectively contain different contrast enhancement materials, the blood vessel contrast enhancement particle 10 and the cancer contrast enhancement particle 20 are depicted with different contrasts on the medical image generated by the medical image diagnostic apparatus. This allows the user to visually discriminate the blood vessel contrast enhancement particle 10 from the cancer contrast enhancement particle 20 on the medical image. That is, the contrast agent according to the embodiment can individually target the vascular system and stromal system of a cancer tissue and image the vascular system and the stromal system so as to make them visually discriminable for a long period of time.

The blood vessel contrast enhancement particle 10 and the cancer contrast enhancement particle 20 will be described in detail next. The blood vessel contrast enhancement particle 10 and the cancer contrast enhancement particle 20 will be referred to as contrast enhancement particles hereinafter unless they are discriminated from each other. A contrast enhancement particle includes a contrast enhancement material and a carrier whose particle size is set in the above manner. The contrast enhancement material is contained in the carrier or bonded to its surface and is carried to a target by the carrier. Typically, a carrier is formed from a material lower in contrast enhancement effect than a contrast enhancement material. As the carrier according to this embodiment, it is suitable to use a nanoparticle such as a liposome, polymer micelle, or dendrimer.

Figure 9:
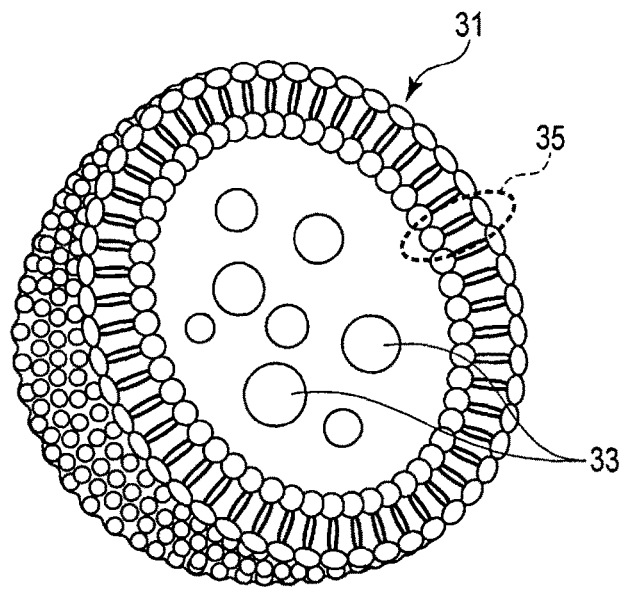
FIG. 9 is a view for exemplarily showing a contrast enhancement particle according to this embodiment, schematically showing a contrast enhancement particle when a carrier is a liposome.

FIG. 9 is a view schematically showing a contrast enhancement particle when a carrier is a liposome 31. As shown in FIG. 9, the liposome 31 is a hollow vesicle composed of a spherically formed lipid bilayer membrane. Contrast enhancement materials 33 having a contrast enhancement effect implemented by a medical image diagnostic apparatus are contained in the liposome 31. The particle size of the liposome 31 can be adjusted by increasing/decreasing the number of phospholipids 35 constituting the lipid bilayer membrane. Although the liposome 31 is composed of the single lipid bilayer membrane in FIG. 9, the liposome may be composed of a plurality of lipid bilayer membranes. When the liposome 31 is the blood vessel contrast enhancement particle 10, the functional group 12 and the PEG 14 are formed on the surface of the liposome 31. When the liposome 31 is the cancer contrast enhancement particle 20, the ligand 22 and the PEG 24 are formed on the surface of the liposome 31. Note that the contrast enhancement materials 33 may be bonded to the surface of the liposome 31.

Figure 10:
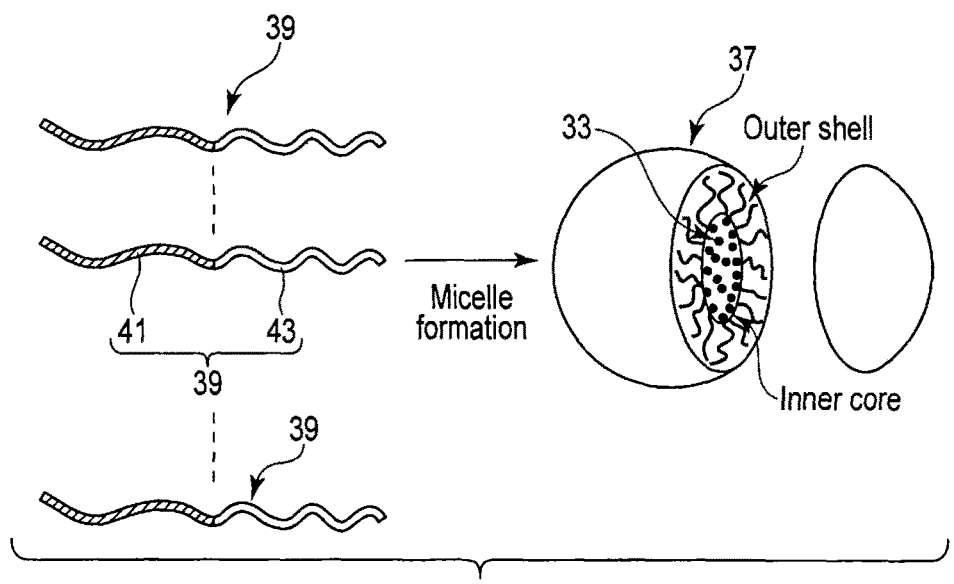
FIG. 10 is a view for exemplarily showing a contrast enhancement particle according to this embodiment, schematically showing a contrast enhancement particle when a carrier is a polymer micelle.

FIG. 10 is a view schematically showing a contrast enhancement particle when a carrier is a polymer micelle 37. As shown in FIG. 10, the polymer micelle 37 is a colloidal particle composed of a plurality of amphipathic block copolymers 39. Each block copolymer 39 contains a hydrophobic segment 41 and a hydrophilic segment 43. The polymer micelle 37 is formed from the plurality of block copolymers 39 such that the hydrophobic segments 41 of the plurality of block copolymers 39 form an inner core, and the hydrophilic segments 43 form an outer shell. The contrast enhancement material 33 may be chemically bonded to the hydrophobic segment 41 or physically adsorbed by the hydrophilic segment 43. As shown in FIG. 10, when chemically bonded to the hydrophobic segment 41, the contrast enhancement material 33 is contained in the polymer micelle 37 so as to be located in the inner core. Although not shown in FIG. 10, when physically adsorbed by the hydrophilic segment 43, the contrast enhancement material 33 is bonded to the polymer micelle 37 so as to be located on its surface. When the polymer micelle 37 is the blood vessel contrast enhancement particle 10, the functional group 12 and the PEG 14 are formed on the surface of the polymer micelle 37. When the polymer micelle 37 is the cancer contrast enhancement particle 20, the ligand 22 and the PEG 24 are formed on the surface of the polymer micelle 37. The particle size of the polymer micelle 37 can be adjusted by, for example, increasing/decreasing the length or number of block copolymers 39. For the sake of easy understanding, FIG. 10 shows the spherical outer shell. In practice, however, no spherical outer shell exists.

Figure 11:
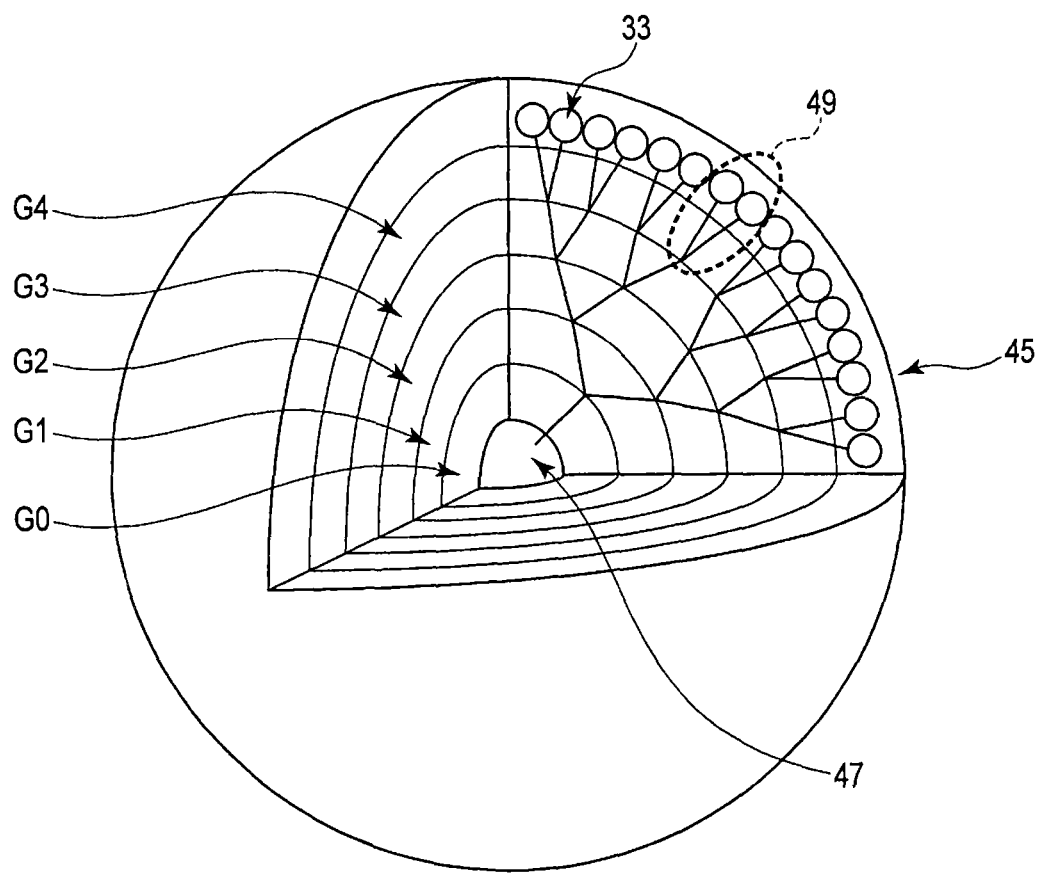
FIG. 11 is a view for exemplarily showing a contrast enhancement particle according to this embodiment, schematically showing a contrast enhancement particle when a carrier is a dendrimer.

FIG. 11 is a view schematically showing a contrast enhancement particle when a carrier is a dendrimer 45. As shown in FIG. 11, the dendrimer 45 is composed of a plurality of unit molecular structures (side chains or dendrons) 49 extending from a central nucleus 47 and bonded to each other in a tree form. As the central nucleus 47, an atom having no contrast enhancement effect is preferably used. The number of times of branching from the central nucleus 47 to the dendrons 49 at the terminals are called generations. FIG. 11 exemplarily shows the dendrimer 45 composed of five generations from a 0th generation G0 to a fourth generation G4. However, the number of generations of the dendrimer 45 according to this embodiment is not limited to 5, and may be any number equal to or more than 1. The contrast enhancement materials 33 are bonded to the functional groups at the terminals of the dendrons 49, of the plurality of the dendrons 49, which are located on the surface side. When the dendrimer 45 is the blood vessel contrast enhancement particle 10, the functional group 12 and the PEG 14 are formed on the surface of the dendrimer 45. When the dendrimer 45 is the cancer contrast enhancement particle 20, the ligand 22 and the PEG 24 are formed on the surface of the dendrimer 45. The particle size of the dendrimer 45 can be adjusted by increasing/decreasing the number of generations, i.e., the number of times of branching of the dendrons 49. Note that FIG. 11 shows the spherical outer shell for the sake of easy understanding, no spherical outer shell practically exists.

According to the above description, the carrier according to this embodiment is a liposome, polymer micelle, or dendrimer. However, the carrier according to the embodiment is not limited to this. The carrier according to the embodiment may be any type of nanoparticle other than a liposome, polymer micelle, and dendrimer as long as a contrast enhancement material can be carried.

In addition, the blood vessel contrast enhancement particle 10 and the cancer contrast enhancement particle 20 may contain the same or different types of carriers. It is possible to individually select optimal types of carriers from the viewpoint of the reliability, easiness, and the like of transfer, accumulation, and retention of the contrast enhancement particles 10 and 20 with respect to a contrast enhancement target (target).

(Medical Image Diagnostic Apparatus)

The medical image diagnostic apparatus according to this embodiment which performs imaging using the contrast agent according to the embodiment will be described next. The medical image diagnostic apparatus according to the embodiment can be applied to both a single type medical image diagnostic apparatus equipped with a single imaging mechanism and a composite type medical image diagnostic apparatus equipped with a plurality of imaging mechanisms. The medical image diagnostic apparatus according to this embodiment will be described separately below as a single type and a composite type. Assume that in the following description, the blood vessel contrast enhancement particles 10 and the cancer contrast enhancement particles 20 have been injected into a subject by a medical professional or a contrast agent injector. The blood vessel contrast enhancement particles 10 and the cancer contrast enhancement particles 20 may be injected at the same timing or different timings as long as the blood vessel contrast enhancement particles 10 and the cancer contrast enhancement particles 20 are mixed with each other in an imaging region.

Figure 12:
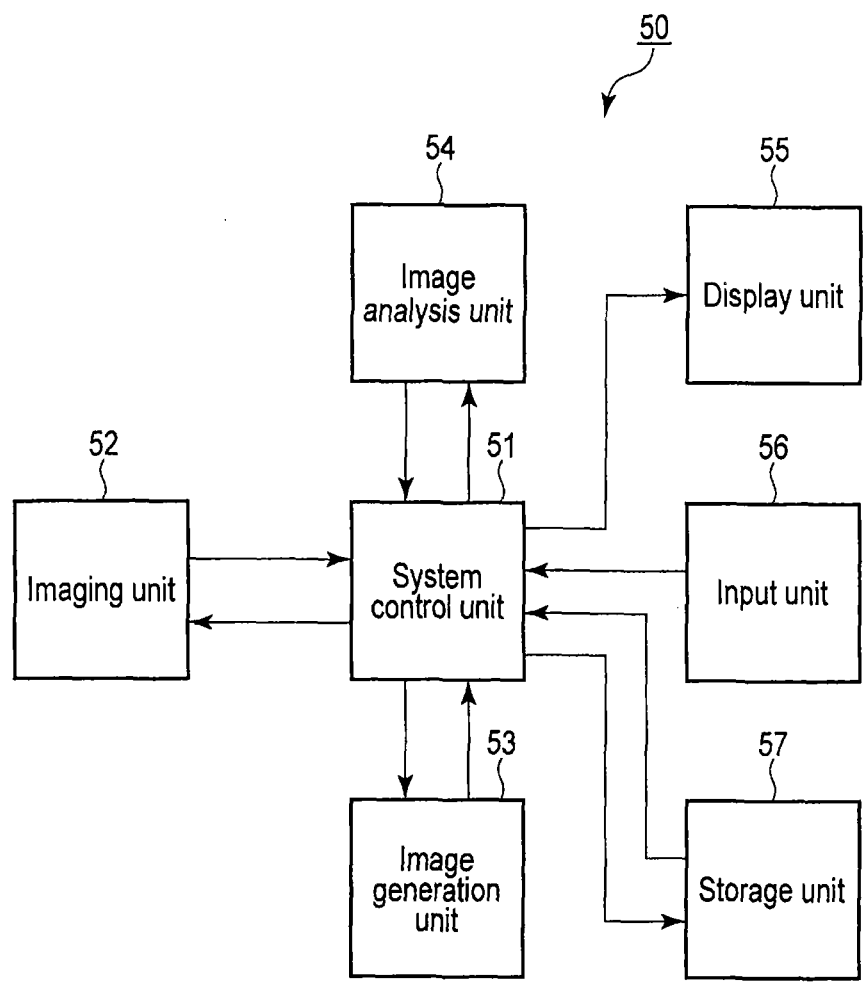
FIG. 12 is a block diagram showing the arrangement of a medical image diagnostic apparatus according to this embodiment.

FIG. 12 is a block diagram showing the arrangement of a medical image diagnostic apparatus 50 according to this embodiment. As shown in FIG. 12, the medical image diagnostic apparatus 50 according to the embodiment includes a system control unit 51 as a central unit, an imaging unit 52, an image generation unit 53, an image analysis unit 54, a display unit 55, an input unit 56, and a storage unit 57.

The imaging unit 52 images an imaging region of a subject injected with the contrast agent according to this embodiment, and generates an output data set associated with the imaging region. An imaging region includes a blood vessel as a contrast enhancement target for the blood vessel contrast enhancement particles 10 and a cancer tissue as a contrast enhancement target for the cancer contrast enhancement particles 20. The imaging unit 52 can perform simultaneous imaging and individual imaging for vascular system imaging and stromal system imaging of a cancer tissue.

Simultaneous imaging is an imaging method of executing both vascular system imaging and stromal system imaging. Individual imaging is an imaging method of individually executing vascular system imaging and stromal system imaging. Vascular system imaging is imaging for acquiring an image (to be referred to as a blood vessel emphasized image hereinafter) on which an image region (to be referred to as a contrast-enhanced blood vessel region hereinafter) associated with a blood vessel whose contrast is enhanced by the blood vessel contrast enhancement particles 10 is more emphasized than an image region (to be referred to as a contrast-enhanced cancer tissue region hereinafter) associated with a cancer tissue whose contrast is enhanced by the cancer contrast enhancement particles 20. Stromal system imaging is imaging for acquiring an image (to be referred to as a cancer tissue emphasized image hereinafter) on which a contrast-enhanced cancer tissue region is more emphasized than a contrast-enhanced blood vessel region. Performing simultaneous imaging including vascular system imaging and stromal system imaging will acquire an image (to be referred to as a blood vessel/cancer tissue emphasized image hereinafter) on which both a contrast-enhanced blood vessel region and a contrast-enhanced cancer tissue region are emphasized. Note that if it is possible to discriminate the contrast enhancement material for the blood vessel contrast enhancement particles 10 from that for the cancer contrast enhancement particles 20, a blood vessel emphasized image and a cancer tissue emphasized image can be generated even by simultaneous imaging including vascular system imaging and stromal system imaging. It is preferable to perform simultaneous imaging or individual imaging at the timing when a targeted blood vessel or diseased tissue is properly contrast-enhanced by the contrast agent. Simultaneous imaging or individual imaging may be performed at an imaging timing when an imaging start instruction is input via the input unit 56 or may be automatically performed at a predetermined timing.

The imaging unit 52 according to this embodiment can be applied to either of a type equipped with a single imaging mechanism and a type equipped with a plurality of imaging mechanisms.

The image generation unit 53 generates a medical image associated with an imaging region based on an output data set from the imaging unit 52. More specifically, when the imaging unit 52 has performed simultaneous imaging, the image generation unit 53 generates a blood vessel/cancer tissue emphasized image based on an output data set from the imaging unit 52. When the imaging unit 52 has performed individual imaging, the image generation unit 53 generates a blood vessel emphasized image based on an output data set associated with vascular system imaging from the imaging unit 52, and generates a cancer tissue emphasized image based on an output data set associated with stromal system imaging from the imaging unit 52.

The image analysis unit 54 performs perfusion analysis on medical images such as a blood vessel/cancer tissue emphasized image, a blood vessel emphasized image, and a cancer tissue emphasized image. For example, the image analysis unit 54 calculates various types of indices indicating blood vessel dynamic states (to be referred to as perfusion indices hereinafter) by perfusion analysis.

The display unit 55 displays medical images such as a blood vessel/cancer tissue emphasized image, a blood vessel emphasized image, and a cancer tissue emphasized image on a display device. The display unit 55 also displays perfusion indices on the display device. As the display device, it is possible to use, for example, a CRT display, liquid crystal display, organic EL display, or plasma display, as needed.

The input unit 56 receives various instructions and information inputs from the user via an input device. For example, the input unit 56 receives an imaging start instruction from the user via an input device. As input devices, it is possible to use a keyboard, mouse, switches, and the like.

The storage unit 57 stores various types of data such as medical images such as a blood vessel/cancer tissue emphasized image, a blood vessel emphasized image, and a cancer tissue emphasized image. The storage unit 57 also stores control programs for the medical image diagnostic apparatus.

The system control unit 51 functions as the central unit of the medical image diagnostic apparatus 50. More specifically, the system control unit 51 reads out a control program stored in the storage unit 57, loads the program in the memory, and controls each unit of the medical image diagnostic apparatus 50 in accordance with the loaded control program.

An operation example of the medical image diagnostic apparatus 50 using the contrast agent according to this embodiment will be described next. For example, the medical image diagnostic apparatus 50 differentiates a diseased tissue region by using the difference in time concentration curve between the blood vessel contrast enhancement particles 10 and the cancer contrast enhancement particles 20. An operation example concerning the differentiation of a diseased tissue region which is performed under the control of the system control unit 51 will be described below.

Figure 13:
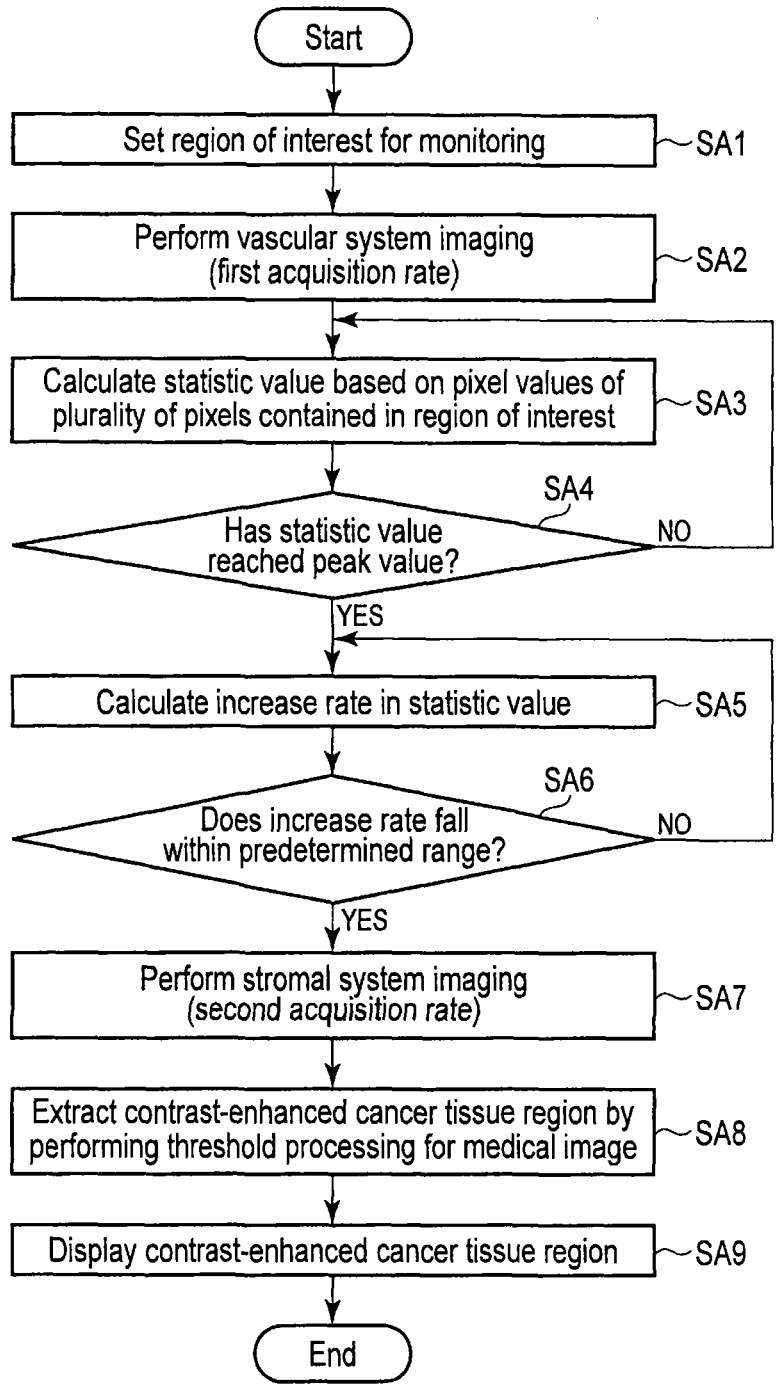
FIG. 13 is a flowchart showing a typical procedure for an operation associated with the differentiation of a diseased tissue region under the control of a system control unit in FIG. 12.

FIG. 13 is a flowchart showing a typical procedure for an operation concerning the differentiation of a diseased tissue region which is performed under the control of the system control unit 51. As shown in FIG. 13, at a stage prior to imaging, the system control unit 51 causes the image analysis unit 54 to perform setting processing of a region of interest (step SA1). In step SA1, the image analysis unit 54 sets a region of interest for monitoring on a predetermined medical image in accordance with an instruction from the user via the input unit 56. A region of interest is set in a local region including a treatment region such as a cancer tissue. A predetermined medical image is a medical image acquired in advance concerning the subject. The coordinates of the region of interest are stored in the storage unit 57. After the region of interest is set, the contrast agent according to this embodiment is injected into a subject S. When preparations for imaging are made, the user inputs an imaging start instruction via the input unit 56.

Upon receiving the imaging start instruction, the system control unit 51 causes the imaging unit 52 to perform vascular system imaging (step SA2). In step SA2, the imaging unit 52 images the subject S at the first acquisition rate to repeatedly acquire output data concerning the subject S. The first acquisition rate will be referred to as a vascular system acquisition rate hereinafter. The user or the like can arbitrarily set a vascular system acquisition rate via the input unit 56. The acquired output data is supplied to the image generation unit 53. The image generation unit 53 repeatedly generates a medical image concerning the subject S based on repeatedly acquired output data. The generated medical image is displayed on the display unit 55.

Upon performing step SA2, the system control unit 51 causes the image analysis unit 54 to perform statistical value calculation processing (step SA3). In step SA3, the image analysis unit 54 reads out the region-of-interest coordinates stored in the storage unit 57, and sets a region of interest at the region-of-interest coordinates on the medical image generated in step SA2. The image analysis unit 54 then calculates a statistical value based on the pixel values of a plurality of pixels contained in the region of interest. Statistical values include, for example, an average value, a maximum value, a minimum value, a total value, and a mode value. For the sake of a concrete description to be made below, assume that a statistical value is an average value.

FIG. 14 is a graph showing the time concentration curve of the contrast agent according to this embodiment. Referring to FIG. 14, the solid line represents the time concentration curve of the contrast agent according to the embodiment, i.e., the time concentration curve concerning the mixture of the blood vessel contrast enhancement particles 10 and the cancer contrast enhancement particles 20, the broken line represents the time concentration curve associated with the blood vessel contrast enhancement particles 10, and the one-dot dashed line represents the time concentration curve of associated with the cancer contrast enhancement particles 20. Assume that an imaging start time point Ts in FIG. 14 coincides with the time point of the inflow of the contrast agent into a region of interest for the sake of convenience. However, in the embodiment, the imaging start time point Ts need not coincide with the contrast agent inflow start time point.

A temporal change in the concentration of the contrast agent according to this embodiment will be described below with reference to FIG. 14. As shown in FIG. 14, the blood vessel contrast enhancement particles 10 reaches a peak value in a region of interest earlier than the cancer contrast enhancement particles 20. The time when the concentration (average value) of the blood vessel contrast enhancement particles 10 reaches the peak value is represented by T_peak. After the concentration (average value) of the blood vessel contrast enhancement particles 10 reaches the peak value, the concentration quickly attenuates. On the other hand, since the ligand 22 is bonded to the cancer contrast enhancement particle 20, the cancer contrast enhancement particle 20 is retained in the cancer tissue for a long period of time. Therefore, the concentration (average value) of the cancer contrast enhancement particle 20 forms a plateau along which the peak value is maintained for a relatively long period of time. The time when the concentration (average value) of the cancer contrast enhancement particles 20 reaches the peak value is represented by T_plat. The time concentration curve of the contrast agent corresponds to the addition of the time concentration curve of the blood vessel contrast enhancement particles 10 and the time concentration curve of the cancer contrast enhancement particles 20. The time concentration curve of the average value based on the pixel values of a plurality of pixels contained in a region of interest corresponds to the time concentration curve associated with the contrast agent in FIG. 14.

As shown in FIG. 14, after time T_plat, the blood vessel contrast enhancement particles 10 are not retained in the blood vessel in the region of interest, but many cancer contrast enhancement particles 20 are retained in the cancer tissue. Therefore, the main imaging target is a stromal system after time T_plat, and this imaging operation will be referred to as stromal system imaging. In contrast, before time T_plat, many blood vessel contrast enhancement particles 10 are retained in the blood vessel in the region of interest, but not many of the cancer contrast enhancement particles 20 are retained in the cancer tissue. Therefore, the main imaging target from time Ts and time T_plat is a vascular system, and this imaging operation will be referred to as vascular system imaging.

Upon performing step SA3, the system control unit 51 causes the image analysis unit 54 to perform determination processing (step SA4). In step SA4, the image analysis unit 54 determines whether the average value calculated in step SA3 has reached the peak value (step SA5). If it is determined that the average value has not reached the peak value (step SA4: NO), the system control unit 51 advances to step SA3 to repeat steps SA3 and SA4 for the latest medical image until it is determined that the average value has reached the peak value. For example, the image analysis unit 54 records the average value calculated in step SA3 in chronological order. If the average value has changed to a smaller value, the image analysis unit 54 determines that the average value has reached the peak.

If it is determined that the average value has reached the peak value (step SA4: YES), the system control unit 51 causes the image analysis unit 54 to perform calculation processing for an increase rate (step SA5). In step SA5, the image analysis unit 54 calculates the increase rate in average value to detect a plateau. An increase rate is defined by the amount of change in average value per unit time. For example, the image analysis unit 54 calculates the increase rate concerning the latest medical image by dividing the difference between the statistical value based on the latest medical image and the statistical value based on the immediately preceding medical image by the time difference between the acquisition time of the latest medical image and the acquisition time of the immediately preceding medical image.

Upon performing step SA5, the system control unit 51 causes the image analysis unit 54 to perform determination processing (step SA6). In step SA6, the image analysis unit 54 determines whether the increase rate calculated in step SA5 falls within a predetermined range. It is preferable to set a predetermined range between the lower limit value and upper limit value which the increase rates can take when the average value has reached a plateau. The user can arbitrarily set this predetermined range via the input unit 56. If it is determined that the increase rate does not fall within the predetermined range (step SA6: NO), the system control unit 51 advances to step SA5 to repeat steps SA5 and SA6 concerning the latest medical image until it is determined that the increase rate has fallen within the predetermined range.

If it is determined that the increase rate has fallen within the predetermined range (step SA6: YES), the system control unit 51 causes the imaging unit 52 to perform stromal system imaging (step SA7). In step SA7, the imaging unit 52 repeatedly acquires output data concerning the subject S by imaging the subject S at the second acquisition rate. The second acquisition rate will be referred to as a stromal system acquisition rate hereinafter. The user or the like can arbitrarily set a stromal system acquisition rate via the input unit 56. The acquired output data is supplied to the image generation unit 53. The image generation unit 53 repeatedly generates a medical image concerning the subject S based on repeatedly acquired output data. The generated medical image is displayed on the display unit 55.

Upon performing step SA7, the system control unit 51 causes the image analysis unit 54 to perform extraction processing (step SA8). In step SA8, the image analysis unit 54 performs threshold processing for the generated medical image to extract pixels having pixel values equal to or more than the threshold. As described above, after time T_plat, the cancer contrast enhancement particles 20 dominantly contribute to contrast enhancement, but the blood vessel contrast enhancement particles 10 hardly contribute to contrast enhancement. For this reason, pixels having pixel values equal to or more than the threshold can be regarded as pixels associated with the tissue contrast-enhanced by the cancer contrast enhancement particles 20, i.e., pixels associated with the contrast-enhanced cancer tissue region. That is, in step SA8, the image analysis unit 54 can extract a contrast-enhanced cancer tissue region from the medical image. The threshold for the extraction of a contrast-enhanced cancer tissue region may be set to the value which is set empirically or experimentally. The user can arbitrarily set this threshold via the input unit 56.

Upon performing step SA8, the system control unit 51 causes the display unit 55 to perform display processing (step SA9). In step SA9, the display unit 55 displays the contrast-enhanced cancer tissue region extracted in step SA8. The user differentiates a cancer tissue by observing the displayed contrast-enhanced cancer tissue region.

The description of the operation associated with the differentiation of a diseased tissue region is complete.

Note that a vascular system acquisition rate and a stromal system acquisition rate can be set to arbitrary values in the above operation example. However, the imaging unit 52 may change the acquisition rate associated with vascular system imaging and the acquisition rate associated with stromal system imaging in accordance with the mixing ratio between the blood vessel contrast enhancement particles 10 and the cancer contrast enhancement particles 20. The mixing ratio will be described below.

The blood vessel contrast enhancement particles 10 and the cancer contrast enhancement particles 20 according to this embodiment may be mixed at an arbitrary ratio. However, it is preferable to mix the blood vessel contrast enhancement particles 10 with the cancer contrast enhancement particles 20 at a ratio corresponding to the purpose of use of the contrast agent. In this case, the ratio at which the blood vessel contrast enhancement particles 10 are mixed with the cancer contrast enhancement particles 20 will be referred to as a mixing ratio. A mixing ratio is defined by the abundance of the cancer contrast enhancement particles 20 in the entire contrast agent relative to the abundance of the blood vessel contrast enhancement particles 10 in the entire contrast agent. An abundance may be any amount including the weight, volume, or molar concentration of the blood vessel contrast enhancement particles 10 or cancer contrast enhancement particles 20.

For example, the contrast agent according to this embodiment is sometimes used to detect a treatment target. In this case, it is important to specify the presence or the like of a tumor nutrient blood vessel by vascular system imaging. For this reason, it is preferable to mix the blood vessel contrast enhancement particles 10 with the cancer contrast enhancement particles 20 such that the abundance of the blood vessel contrast enhancement particles 10 in the entire contrast agent is larger than that of the cancer contrast enhancement particles 20 in the entire contrast agent. For example, it is preferable to mix the blood vessel contrast enhancement particles 10 with the cancer contrast enhancement particles 20 at a mixing ratio of 2:1. A vascular system is emphasized compared with a stromal system on a medical image by imaging a subject injected with the contrast agent containing the blood vessel contrast enhancement particles 10 and the cancer contrast enhancement particles 20 mixed at such a ratio. This allows the user to efficiently specify the presence or the like of a tumor nutrient blood vessel.

Figure 15:
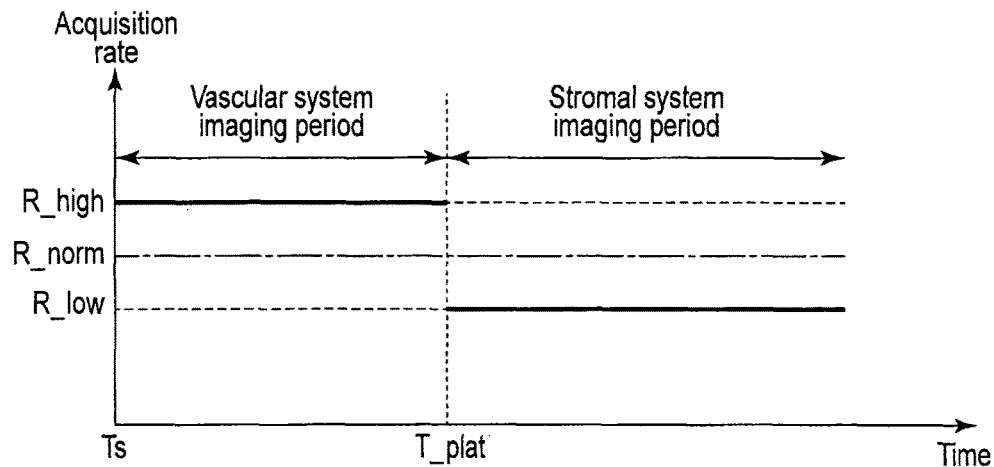
FIG. 15 is a graph showing acquisition rates in vascular system imaging and stromal system imaging when the abundance of blood vessel contrast enhancement particles is larger than that of cancer contrast enhancement particles according to this embodiment.

FIG. 15 is a view showing the acquisition rates in vascular system imaging and stromal system imaging when the abundance of the blood vessel contrast enhancement particles 10 is larger than that of the cancer contrast enhancement particles 20. When the abundance of the blood vessel contrast enhancement particles 10 is larger than that of the cancer contrast enhancement particles 20, the imaging unit 52 sets the vascular system acquisition rate to an acquisition rate R_high higher than a normal acquisition rate R_norm, and sets the stromal system acquisition rate to an acquisition rate R_low lower than R_norm. The imaging unit 52 executes vascular system imaging at the acquisition rate R_high in the period from time Ts and time T_plat, and executes stromal system imaging at the acquisition rate R_low in the period from time T_plat to the end time. With this operation, the display unit 55 can display a medical image associated with vascular system imaging with a higher time resolution than a medical image associated with stromal system imaging.

In addition, the contrast agent according to this embodiment is sometimes used to determine a treatment effect. In this case, since the main purpose is to observe a treatment process, stromal system imaging is more important than vascular system imaging. For this reason, it is preferable to mix the blood vessel contrast enhancement particles 10 with the cancer contrast enhancement particles 20 such that the abundance of the blood vessel contrast enhancement particles 10 in the entire contrast agent is smaller than that of the cancer contrast enhancement particles 20 in the entire contrast agent. For example, the blood vessel contrast enhancement particles 10 are preferably mixed with the cancer contrast enhancement particles 20 at a mixing ratio of 1:2. A stromal system is emphasized compared with a vascular system on a medical image by imaging a subject injected with the contrast agent containing the blood vessel contrast enhancement particles 10 and the cancer contrast enhancement particles 20 mixed at such a ratio. This allows the user to efficiently specify a treatment effect on the stromal system.

Figure 16:
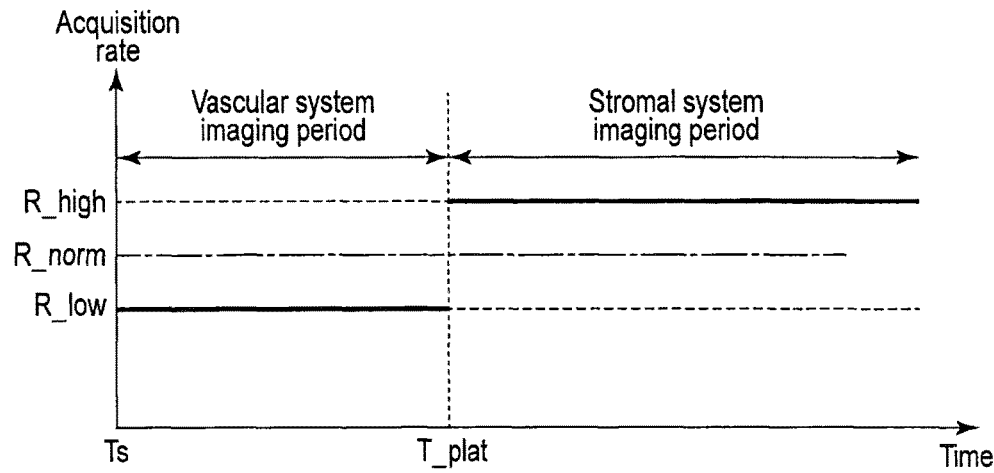
FIG. 16 is a graph showing acquisition rates in vascular system imaging and stromal system imaging when the abundance of blood vessel contrast enhancement particles is smaller than that of cancer contrast enhancement particles according to this embodiment.

FIG. 16 is a graph showing acquisition rates in vascular system imaging and stromal system imaging when the abundance of the blood vessel contrast enhancement particles 10 is smaller than that of the cancer contrast enhancement particles 20. When the abundance of the blood vessel contrast enhancement particles 10 is smaller than that of the cancer contrast enhancement particles 20, the imaging unit 52 sets the vascular system acquisition rate to the acquisition rate R_low lower than the normal acquisition rate R_norm, and sets the stromal system acquisition rate to the acquisition rate R_high higher than R_norm. The imaging unit 52 executes vascular system imaging at the acquisition rate R_low in the period from time Ts and time T_plat, and executes stromal system imaging at the acquisition rate R_high in the period from time T_plat to the end time. With this operation, the display unit 55 can display a medical image associated with stromal system imaging with a higher time resolution than a medical image associated with vascular system imaging.

With the above arrangement, the medical image diagnostic apparatus 50 can clearly image the vascular system and stromal system of the cancer tissue by executing imaging using the contrast agent according to this embodiment.

[Single Type]

The medical image diagnostic apparatus 50 will be described separately as single type medical image processing apparatuses and composite type medical image processing apparatuses. Described first is each of the cases in which the single type medical image diagnostic apparatus 50 is a photon counting CT apparatus, X-ray computed tomography imaging apparatus, ultrasonic diagnostic apparatus, magnetic resonance diagnostic apparatus, PET apparatus, SPECT apparatus, or X-ray diagnostic apparatus. Note that in the following description, the same reference numerals denote constituent elements having almost the same functions as those included in the medical image diagnostic apparatus 50, and a repetitive description will be made only when required.

(Photon Counting CT Apparatus)

FIG. 17 is a block diagram showing the arrangement of a photon counting CT apparatus 60 according to this embodiment. As shown in FIG. 17, the photon counting CT apparatus 60 includes a gantry (imaging unit) 52-1 and a console 61-1. The gantry 52-1 supports a rotating frame 511 having a cylindrical shape so as to allow it to rotate about the rotation axis Z. An X-ray generation unit 513 and an X-ray detection unit 515 are mounted on the rotating frame 511 so as to face each other through the rotation axis Z. The opening portion of the rotating frame 511 is set to an imaging area. A top 517 is positioned in the opening portion of the rotating frame 511. The subject S is placed on the top 517. The top 517 is moved such that an imaging region of the subject S placed on the top 517 is included in the imaging area. The rotating frame 511 rotates about the rotation axis Z at a constant angular velocity upon receiving power from a rotation driving unit 519. The rotation driving unit 519 generates power for rotating the rotating frame 511 in accordance with a drive signal from a gantry control unit 521.

The X-ray generation unit 513 generates X-rays. More specifically, the X-ray generation unit 513 includes an X-ray tube 523 and a high voltage generator 525. The X-ray tube 523 generates X-rays upon receiving a high voltage and a filament current from the high voltage generator 525. The high voltage generator 525 applies a high voltage to the X-ray tube 523 in accordance with a control signal from the gantry control unit 521, and supplies a filament current to the X-ray tube 523 in accordance with a control signal from the gantry control unit 521.

The X-ray detection unit 515 detects X-rays generated from the X-ray generation unit 513 and transmitted through the subject S and counts the number of X-ray photons detected. More specifically, the X-ray detection unit 515 includes an X-ray detector 527 and a counting circuit 529.

The X-ray detector 527 detects X-ray photons generated from the X-ray tube 523. The X-ray detector 527 is equipped with a plurality of X-ray detection elements arranged two-dimensionally. Each X-ray detection element detects an X-ray photon from the X-ray tube 523, and generates an electrical pulse (electrical signal) corresponding to the energy of the detected X-ray photon.

The counting circuit 529 counts the number of X-ray photons detected by the X-ray detector 527 in accordance with a control signal from the gantry control unit 521. As counting schemes used by the counting circuit 529, the sinogram mode scheme and the list mode scheme are known. In the sinogram mode scheme, the counting circuit 529 performs pulse height discrimination of electrical pulses from the X-ray detector 527, and counts the number of electrical pulses in each of predetermined energy bands as the number of X-ray photons for each view. In the list mode scheme, the counting circuit 529 performs pulse height discrimination of electrical pulses from the X-ray detector 527, and records the energy value of each electrical pulse as the energy value of each X-ray photon in association with a detection time. The counting circuit 529 refers to the record to classify X-ray photons according to a plurality of predetermined energy bands and count the number of X-ray photons in each of the plurality of energy bands for each view. The number of X-ray photons counted by the counting circuit 529 will be referred to as a count hereinafter. Although the counting circuit 529 is provided on the gantry 52-1, the gantry 52-1 may be provided in the console 61-1.

The gantry control unit 521 comprehensively controls the respective types of devices mounted on the gantry 52-1 in accordance with instructions from the system control unit 51 in the console 61-1. For example, the gantry control unit 521 controls the X-ray generation unit 513, the X-ray detection unit 515, and the rotation driving unit 519 to perform PCCT imaging of the subject S injected with the contrast agent according to this embodiment.

The console 61-1 includes an image generation unit 53-1, the image analysis unit 54, the display unit 55, the input unit 56, the storage unit 57, and the system control unit 51.

The image generation unit 53-1 generates a PCCT image expressing the spatial distribution of counts based on count data from the counting circuit 529. For example, the image generation unit 53-1 generates a blood vessel emphasized image based on the count of X-ray photons belonging to an energy band corresponding to the contrast enhancement material contained in the blood vessel contrast enhancement particles 10. In addition, the image generation unit 53-1 generates a cancer tissue emphasized image based on the count of X-ray photons belonging to an energy band corresponding to the contrast enhancement material contained in the cancer contrast enhancement particles 20. The display unit 55 displays PCCT images such as a blood vessel emphasized image and a cancer tissue emphasized image.

A specific example of a contrast agent (to be referred to as a PCCT contrast agent hereinafter) according to this embodiment which is used for the photon counting CT apparatus will be described below. The contrast enhancement mechanism of the PCCT contrast agent can change the intensity of X-ray photons transmitted through the contrast agent by increasing the X-ray attenuation coefficient difference between the contrast agent and a surrounding tissue. As a contrast enhancement material for a PCCT contrast agent, it is preferable to use a heavy metal or the like higher in X-ray attenuation coefficient than a surrounding tissue of a contrast enhancement target. Such heavy metals include, for example, iodine I, gadolinium Gd, gold Au, and bismuth Bi. Heavy metals having different contrast enhancement effects are preferably selected, as needed, from heavy metals such as iodine I, gadolinium Gd, gold Au, and bismuth Bi as the contrast enhancement materials for the blood vessel contrast enhancement particle 10 and the cancer contrast enhancement particle 20. As a carrier, it is possible to use any of a liposome, polymer micelle, and dendrimer which can contain a heavy metal having a high X-ray attenuation coefficient or to which it can be bonded. Note that gadolinium Gd, gold Au, and bismuth Bi have slight toxicity to the human body, whereas a liposome has the property capable of reducing toxicity. For this reason, when gadolinium Gd, gold Au, or bismuth Bi is to be used as a contrast enhancement material, the contrast enhancement material is preferably contained in a liposome. Note that if it is possible to reduce toxicity by a technique other than being contained in a liposome, gadolinium Gd, gold Au, or bismuth Bi may be contained in or bonded to any carrier.

The photon counting CT apparatus 60 may generate a blood vessel emphasized image with an emphasized contrast-enhanced blood vessel region and a cancer tissue emphasized image with an emphasized contrast-enhanced cancer tissue region by using the difference in characteristic X-ray (K-absorption edge) between the contrast enhancement material contained in the blood vessel contrast enhancement particles 10 and the contrast enhancement material contained in the cancer contrast enhancement particles 20.

Figure 18:
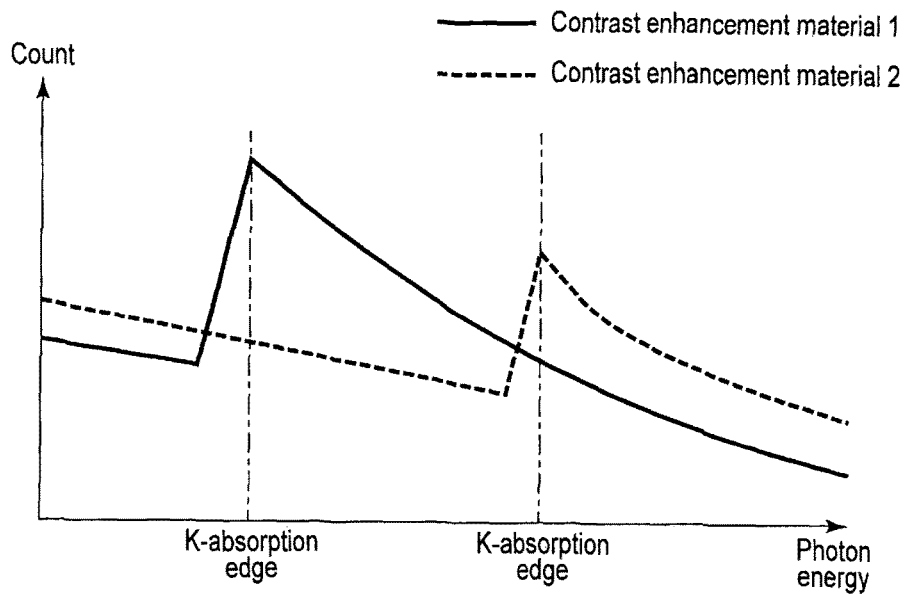
FIG. 18 is a graph for explaining a K-absorption edge for each contrast enhancement material, schematically showing the energy spectra of contrast enhancement material 1 and contrast enhancement material 2.

FIG. 18 is a graph for explaining a K-absorption edge for each contrast enhancement material, schematically showing the energy spectra of contrast enhancement material 1 and contrast enhancement material 2. The ordinate of the graph in FIG. 18 is defined by the number of X-ray photons (count), and the abscissa is defined by photon energy. As shown in FIG. 18, the photon energies at the K-absorption edges of contrast enhancement material 1 and contrast enhancement material 2 differ from each other. The photon energy at a K-absorption edge is unique to a material. It is therefore possible to discriminate a material by identifying the photon energy at the K-absorption edge. A method of performing imaging for each material by using the differences in K-absorption edge between the respective materials is called a K-edge imaging.

Figure 19:
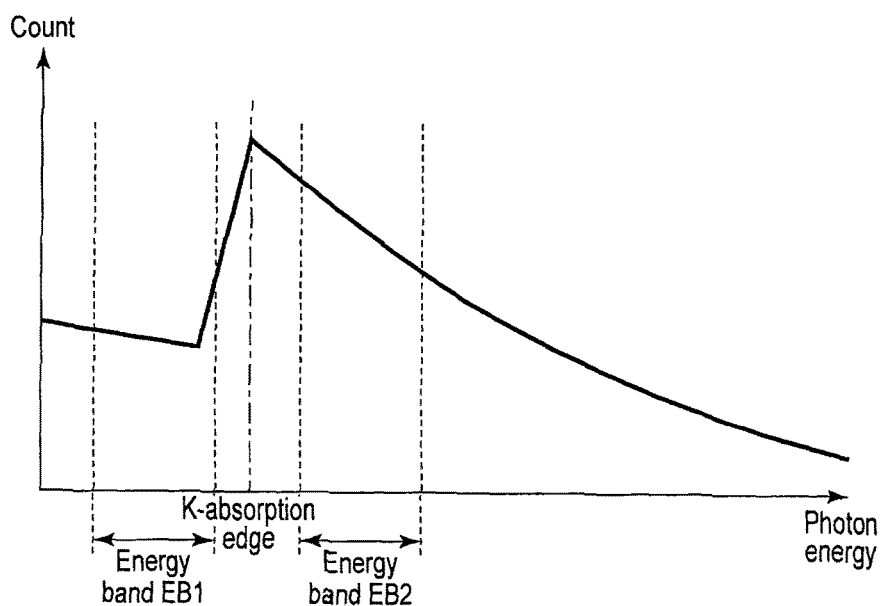
FIG. 19 is a graph for explaining a processing method for K-edge imaging performed by an image generation unit, schematically showing the energy spectrum of contrast enhancement material 1 in FIG. 18.

FIG. 19 is a graph for explaining a processing method for K-edge imaging performed by the image generation unit 53-1, schematically showing the energy spectrum of contrast enhancement material 1 in FIG. 18. As shown in FIG. 19, the image generation unit 53-1 sets two energy bands EB1 and EB2 on the two sides of the K-absorption edge of contrast enhancement material 1. The energy band EB1 is set to a band slightly lower than the photon energy at the K-absorption edge, and the energy band EB2 is set to a band slightly higher than the photo energy at the K-absorption edge. The image generation unit 53-1 generates an image expressing the spatial distribution of contrast enhancement material 1 based on the count in the energy band EB2 and the count in the energy band EB2. Note that the user can arbitrarily set the energy widths and positions of the energy band EB1 and energy band EB2 via the input unit 56.

The image generation unit 53-1 generates a blood vessel emphasized image and a cancer tissue emphasized image by using the above processing method for K-edge imaging. That is, the image generation unit 53-1 generates a blood vessel emphasized image expressing the spatial distribution of the contrast-enhanced blood vessel contrast-enhanced by the blood vessel contrast enhancement particles 10 based on the counts in the two energy bands on the two sides of the K-absorption edge of the contrast enhancement material contained in the blood vessel contrast enhancement particles 10. Likewise, the image generation unit 53-1 generates a cancer tissue emphasized image expressing the spatial distribution of the contrast-enhanced cancer tissue contrast-enhanced by the cancer contrast enhancement particles 20 based on the counts in the two energy bands on the two sides of the K-absorption edge of the contrast enhancement material contained in the cancer contrast enhancement particle 20. The display unit 55 generates a blood vessel emphasized image and a cancer tissue emphasized image. Note that the display unit 55 may superimpose and display the blood vessel emphasized image and the cancer tissue emphasized image.

As described above, the photon counting CT apparatus 60 can generate a blood vessel emphasized image and a cancer tissue emphasized image by simultaneous imaging.

In the above description, the photon counting CT apparatus 60 is a so-called third generation. That is, the photon counting CT apparatus 60 is of a rotate/rotate-type in which the X-ray tube 523 and the X-ray detector 527 rotate together around the subject S. However, the photon counting CT apparatus 60 according to this embodiment is not limited to this. For example, the photon counting CT apparatus 60 may be of a stationary/rotate-type in which only the X-ray tube 523 rotates around a subject while many X-ray detection elements arranged in a ring form are fixed.

(X-Ray Computed Tomography Imaging Apparatus)

FIG. 20 is a block diagram showing the arrangement of an X-ray computed tomography imaging apparatus 70 according to this embodiment. As shown in FIG. 20, the X-ray computed tomography imaging apparatus 70 includes a gantry (imaging unit) 52-2 and a console 61-2. The gantry 52-2 supports a rotating frame 541 having a cylindrical shape so as to allow it to rotate about the rotation axis Z. An X-ray generation unit 543 and an X-ray detection unit 545 are mounted on the rotating frame 541 so as to face each other through the rotation axis Z. The opening portion of the rotating frame 541 is set to an imaging area. A top 547 is positioned in the opening portion of the rotating frame 541. The subject S is placed on the top 547. The top 547 is moved such that an imaging region of the subject S placed on the top 547 is included in the imaging area. The rotating frame 541 rotates about the rotation axis Z at a constant angular velocity upon receiving power from a rotation driving unit 549. The rotation driving unit 549 generates power for rotating the rotating frame 541 in accordance with a drive signal from a gantry control unit 551.

The X-ray generation unit 543 generates X-rays. More specifically, the X-ray generation unit 543 includes an X-ray tube 553 and a high voltage generator 555. The X-ray tube 553 generates X-rays upon receiving a high voltage and a filament current from the high voltage generator 555. The high voltage generator 555 applies a high voltage to the X-ray tube 553 in accordance with a control signal from the gantry control unit 551, and supplies a filament current to the X-ray tube 553 in accordance with a control signal from the gantry control unit 551.

The X-ray detection unit 545 detects X-rays generated from the X-ray tube 543 and transmitted through the subject S and generates digital data corresponding to the detected X-ray energy. More specifically, the X-ray detection unit 545 includes an X-ray detector 557 and a data acquisition circuit 559.

The X-ray detector 557 detects X-rays generated from the X-ray tube 553. The X-ray detector 557 is equipped with a plurality of X-ray detection elements arranged two-dimensionally. Each X-ray detection element detects X-rays from the X-ray tube 553, and generates an electrical signal corresponding to the detected X-ray energy.

The data acquisition circuit 559 measures the X-ray energy detected by the X-ray detector 557 in accordance with a control signal from the gantry control unit 551. More specifically, the data acquisition circuit 559 acquires electrical signals from the respective X-ray detection elements for each view and converts the acquired electrical signals into digital data. Digital data is called raw data.

The gantry control unit 551 comprehensively controls the respective types of devices mounted on the imaging unit 52-2 in accordance with instructions from the system control unit 51 in the console 61-2. For example, the gantry control unit 551 controls the X-ray generation unit 543, the X-ray detection unit 545, and the rotation driving unit 549 to perform X-ray CT imaging of the subject S injected with the contrast agent according to this embodiment.

The console 61-2 includes an image generation unit 53-2, an image analysis unit 54, a display unit 55, an input unit 56, a storage unit 57, and a system control unit 51.

The image generation unit 53-2 generates a CT image expressing the spatial distribution of CT values based on raw data from the data acquisition circuit 559. More specifically, the image generation unit 53-2 includes a preprocessing unit 531 and a reconstruction unit 532. The preprocessing unit 531 performs preprocessing such as projection conversion or the like for the raw data to generate projection data. The reconstruction unit 532 performs reconstruction computation for the projection data to generate a CT image.

A specific example of a contrast agent (to be referred to as a CT contrast agent hereinafter) according to this embodiment which is used for the X-ray computed tomography imaging apparatus 70 will be described below. The contrast enhancement mechanism of the CT contrast agent reduces to changing the intensity of X-rays transmitted through the contrast agent by increasing the X-ray attenuation coefficient difference between the contrast agent and a surrounding tissue. As a contrast enhancement material for a CT contrast agent, it is preferable to use a heavy metal with a high X-ray attenuation coefficient such as iodide I. That is, only iodide is a suitable contrast enhancement material for a CT contrast agent. Therefore, iodide I is used as a contrast enhancement material contained in the blood vessel contrast enhancement particles 10 and a contrast enhancement material contained in the cancer contrast enhancement particles 20 of the CT contrast agent. As a carrier, it is possible to use any of a liposome, polymer micelle, and dendrimer which can contain a heavy metal having a high X-ray attenuation coefficient or to which it can be bonded.

As described above, the gantry control unit 551 controls the X-ray generation unit 543, the X-ray detection unit 545, and the rotation driving unit 549 to perform X-ray CT imaging of the subject injected with the CT contrast agent. When performing simultaneous imaging including vascular system imaging and stromal system imaging, the gantry control unit 551 executes X-ray CT imaging at the timing when the blood vessel in the imaging region is filled with the blood vessel contrast enhancement particles 10 and the cancer tissue in the imaging region is filled with the cancer contrast enhancement particles 20. With this operation, an image generation unit 53-2 can generate a blood vessel/cancer tissue emphasized image on which both a contrast-enhanced blood vessel and a contrast-enhanced cancer tissue are emphasized, based on the raw data acquired by the X-ray CT imaging. When performing individual imaging including vascular system imaging and stromal system imaging, the gantry control unit 551 executes X-ray CT imaging at the timing when the blood vessel in the imaging region is filled with the blood vessel contrast enhancement particles 10, and executes X-ray CT imaging at the timing when the cancer tissue in the imaging region is filled with the cancer contrast enhancement particles 20. With this operation, the image generation unit 53-2 can individually generate a blood vessel emphasized image on which a contrast-enhanced blood vessel is emphasized and a cancer tissue emphasized image on which a contrast-enhanced cancer tissue is emphasized. Note that the user can input an imaging start instruction for X-ray CT imaging via the input device at an arbitrary timing.

Note that the gantry control unit 551 may perform time-series imaging with respect to this imaging region. X-ray CT imaging is repeatedly performed with respect to the imaging region to generate time-series CT images and display them on the display device. It is therefore possible to observe, in chronological order, how the blood vessel contrast enhancement particles 10 flow in the blood vessel and how the cancer contrast enhancement particles 20 are accumulated in the cancer tissue.

In the above description, the X-ray computed tomography imaging apparatus 70 is of a rotate/rotate-type. However, the X-ray computed tomography imaging apparatus 70 according to this embodiment is not limited to this. For example, the X-ray computed tomography imaging apparatus 70 may be of a stationary/rotate-type.

(Ultrasonic Diagnostic Apparatus)

Figure 21:
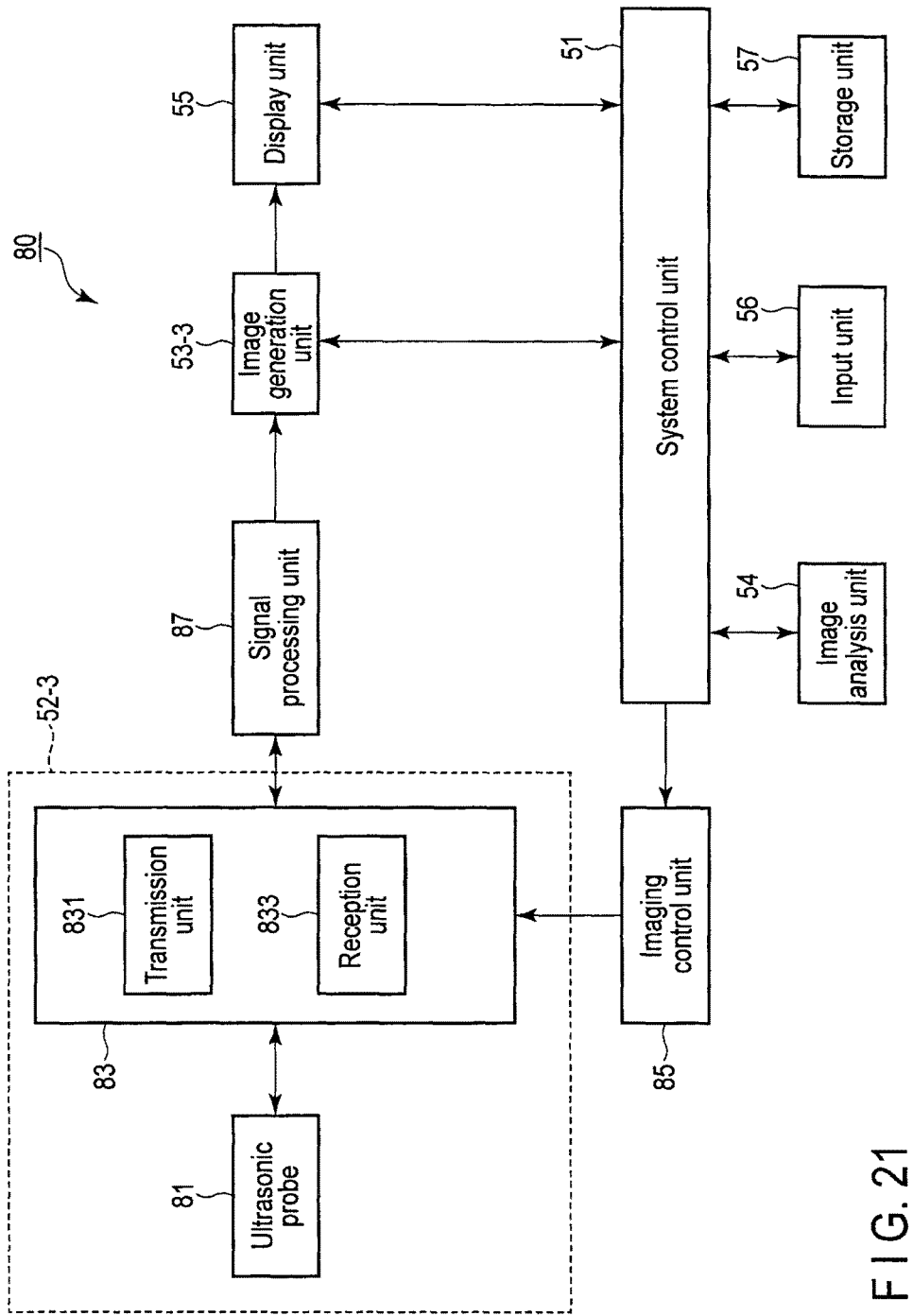
FIG. 21 is a block diagram showing the arrangement of an ultrasonic diagnostic apparatus according to this embodiment.

FIG. 21 is a block diagram showing the arrangement of an ultrasonic diagnostic apparatus 80 according to this embodiment. As shown in FIG. 21, the ultrasonic diagnostic apparatus 80 includes an ultrasonic probe 81, a transmission/reception unit 83, an imaging control unit 85, a signal processing unit 87, an image generation unit 53-3, and an image analysis unit 54, a display unit 55, an input unit 56, a storage unit 57, and a system control unit 51.

The ultrasonic probe 81 includes a plurality of transducers arranged one-dimensionally or two-dimensionally. The transducers receive transmission drive pulses from a transmission/reception unit 83, and transmit ultrasonic waves to a subject in the form of a beam. The transmitted ultrasonic waves are sequentially reflected by the discontinuity points (echo sources) of acoustic impedance of an internal body tissue of the subject. When ultrasonic waves are reflected by a moving body such as a blood flow, the ultrasonic waves are Doppler-shifted. The reflected ultrasonic waves are received by the transducers. The transducers convert the received ultrasonic waves into echo signals (electrical signals). The echo signals are supplied to the transmission/reception unit 83.

The transmission/reception unit 83 scans the subject via the ultrasonic probe 81 under the control of the imaging control unit 85. The transmission/reception unit 83 includes the transmission unit 831 and a reception unit 833. The transmission unit 831 transmits ultrasonic waves to the subject via the ultrasonic probe 81. The reception unit 833 receives echo signals corresponding to the intensities of the ultrasonic waves reflected by the subject via the ultrasonic probe 81. The reception unit 833 generates a reception signal for each ultrasonic scanning line based on the received echo signals.

As shown in FIG. 17, the ultrasonic probe 81 and the transmission/reception unit 83 constitute an imaging unit 52-3 which ultrasonically images a subject.

The imaging control unit 85 controls the transmission unit 831 and the reception unit 833 in accordance with instructions from the system control unit 51 to ultrasonically image the subject injected with the contrast agent according to this embodiment.

The signal processing unit 87 performs envelope detection processing and logarithmic processing for reception signals from the reception unit 833 to generate a B-mode signal expressing the amplitude intensities of the reflected ultrasonic waves along ultrasonic scanning lines. The amplitude intensities correspond to the acoustic impedance differences between substances existing on the ultrasonic scanning lines.

The image generation unit 53-3 generates an ultrasonic image in real time based on a B-mode signal from the signal processing unit 87. An ultrasonic image is an image expressing the spatial distribution of the acoustic impedance differences between substances existing in an imaging region. The display unit 55 displays an ultrasonic image in real time.

A specific example of a contrast agent (to be referred to as an ultrasonic contrast agent hereinafter) according to this embodiment which is used for the ultrasonic diagnostic apparatus 80 will be described below. The imaging mechanism of the ultrasonic contrast agent can increase the reflection intensity of ultrasonic waves using the contrast agent by increasing the impedance differences between the contrast agent and a surrounding tissue. It is therefore not necessary to use any contrast enhancement material for the ultrasonic contrast agent. As a carrier for the ultrasonic contrast agent, it is possible to use any nanoparticle of the above liposome, polymer micelle, and dendrimer. However, as a carrier for the ultrasonic contrast agent, it is preferable to use spherical nanoparticles which can isotropically reflect ultrasonic waves. From this point of view, a liposome is suitable as a carrier for the ultrasonic contrast agent. Ultrasonic contrast agents are roughly classified into first and second generations. A first-generation ultrasonic contrast agent is used to visualize the behavior of the ultrasonic contrast agent accumulated in a target, which is perfused to the target again after being crushed by ultrasonic waves. For this reason, as the first-generation ultrasonic contrast agent, a hollow liposome is suitably used. The type of gas to be contained in the liposome is not specifically limited. The gas to be contained in the liposome includes, for example, air and hydrogen fluoride. A second-generation ultrasonic contrast agent is used to visualize the behavior of the scattered ultrasonic contrast agent which has been accumulated in a target and scattered by ultrasonic waves. For this reason, the second-generation ultrasonic contrast agent need not be hollow, and any type of nanoparticle such as a liposome, polymer micelle, or dendrimer can be used. Even when a carrier such as a liposome, polymer micelle, or dendrimer is to be used as an ultrasonic contrast agent, the functional group 12, the PEG 14, the ligand 22, and the PEG 24 can be bonded to the surface of the carrier, as needed.

An operation example of the ultrasonic diagnostic apparatus using the first-generation ultrasonic contrast agent will be described below. The blood vessel contrast enhancement particles and cancer contrast enhancement particles contained in the ultrasonic contrast agent according to this embodiment differ in ultrasonic intensity or frequency at which the particles can be crushed or excessively vibrated. Although a phenomenon in which particles are crushed by ultrasonic waves will be described below, the same applies to particles which undergo excessive vibrations caused by ultrasonic waves. The following description will exemplify the case of using differences in the occurrence of a crushing phenomenon due to differences in ultrasonic frequency. However, it is possible to use differences in the occurrence of a crushing phenomenon due to differences in the transmission intensity of ultrasonic waves. In addition, it is possible to use differences in the occurrence of an excessive vibration phenomenon due to the transmission intensity of ultrasonic waves.

Figure 22:
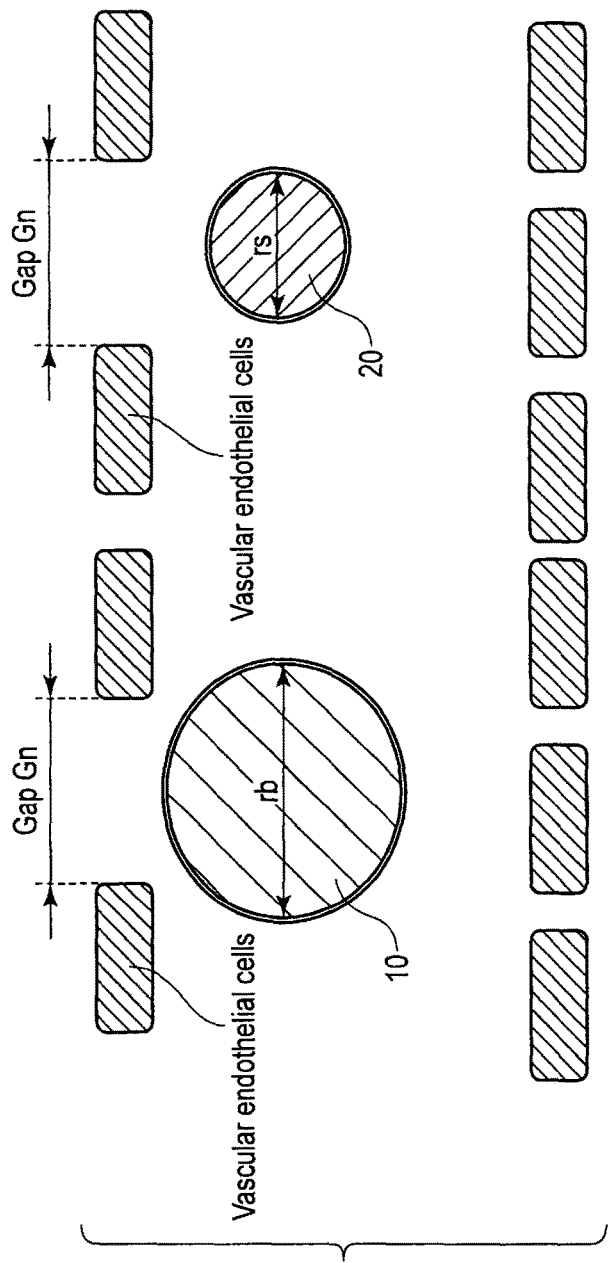
FIG. 22 is a view showing the comparisons between the particle size and crushing frequency of a blood vessel contrast enhancement particle and those of a cancer contrast enhancement particle contained in an ultrasonic contrast agent according to this embodiment.

FIG. 22 is a view showing the comparisons between the particle size and crushing frequency of the blood vessel contrast enhancement particle 10 and those of the cancer contrast enhancement particle 20 contained in an ultrasonic contrast agent according to this embodiment. Assume that a carrier for the blood vessel contrast enhancement particle 10 and the cancer contrast enhancement particle 20 is a liposome. As shown in FIG. 22, the blood vessel contrast enhancement particle 10 is adjusted to be larger than the vascular endothelial cell gap Ga at the time of the occurrence of the EPR effect, and the cancer contrast enhancement particle 20 is adjusted to be smaller than the gap Ga. The strengths of the blood vessel contrast enhancement particle 10 and cancer contrast enhancement particle 20 are adjusted such that the respective particles are crushed by ultrasonic waves with different frequencies or intensities. For example, the structural strengths of the blood vessel contrast enhancement particle 10 and cancer contrast enhancement particle 20 are adjusted such that the blood vessel contrast enhancement particle 10 is crushed upon receiving an ultrasonic wave with a frequency higher than a frequency fb, and the cancer contrast enhancement particle 20 is crushed upon receiving an ultrasonic wave with a frequency higher than a frequency fs. The structure strengths of the blood vessel contrast enhancement particle 10 and cancer contrast enhancement particle 20 can be adjusted by various techniques. For example, it is preferable to adjust a structural strength by coating a liposome with a material such as carbon.

The lower limit of frequencies at which the blood vessel contrast enhancement particle 10 or the cancer contrast enhancement particle 20 can be crushed will be referred to as a crushing frequency hereinafter. The magnitude relationship in crushing frequency between the blood vessel contrast enhancement particle 10 and the cancer contrast enhancement particle 20 can be arbitrarily adjusted in accordance with a reperfusion observation target. If, for example, the reperfusion of the cancer contrast enhancement particle 20 to a cancer tissue is an observation target, the crushing frequency fs of the cancer contrast enhancement particle 20 is set to be lower than the crushing frequency of the blood vessel contrast enhancement particle 10. If the reperfusion of the blood vessel contrast enhancement particle 10 to a diseased blood vessel region is an observation target, the crushing frequency fb of the blood vessel contrast enhancement particle 10 is set to be lower than the crushing frequency fs of the cancer contrast enhancement particle 20. In other words, the crushing frequencies fb and fs for the contrast enhancement particles 10 and 20 to be crushed are adjusted to be lower than the frequencies of ultrasonic waves (to be referred to as crushing ultrasonic waves hereinafter) for crushing the contrast enhancement particles, whereas the crushing frequencies fb and fs for the contrast enhancement particles 10 and 20 not to be crushed are adjusted to be higher than the frequencies of crushing ultrasonic waves. This makes it possible to selectively crush the blood vessel contrast enhancement particle 10 and the cancer contrast enhancement particle 20.

Figure 23:
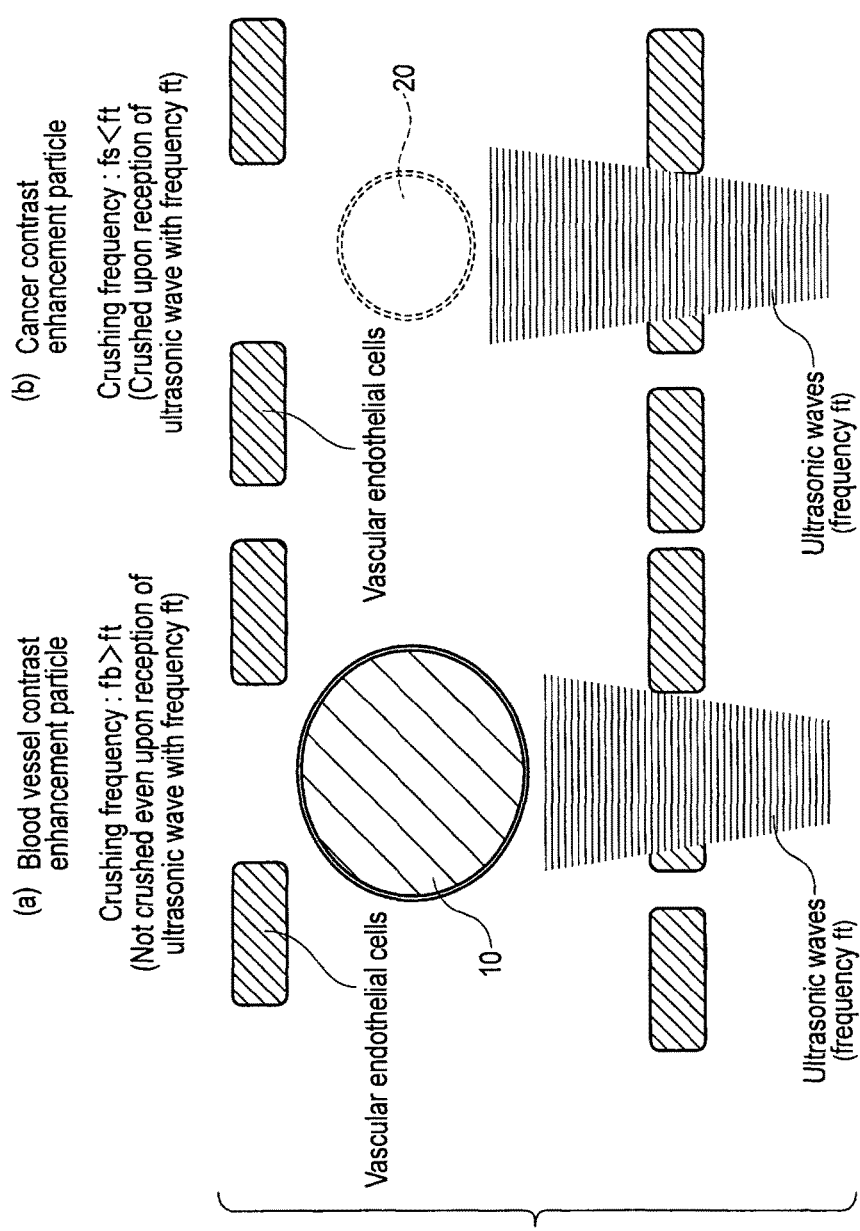
FIG. 23 is a view showing the comparison between a crushing frequency ft of a blood vessel contrast enhancement particle and that of a cancer contrast enhancement particle in a case in which the reperfusion of the cancer contrast enhancement particle in FIG. 22 into a cancer tissue is an observation target.

FIG. 23 is a view showing the comparison between a crushing frequency ft and the crushing ultrasonic frequencies of the blood vessel contrast enhancement particle 10 and cancer contrast enhancement particle 20 in a case in which the reperfusion of the cancer contrast enhancement particle 20 into a cancer tissue is an observation target. As shown in FIG. 23, the crushing frequency fs for the cancer contrast enhancement particle 20 is set to be lower than the frequency ft of crushing ultrasonic waves. When, therefore, the cancer contrast enhancement particle 20 receives a crushing ultrasonic wave of the frequency ft, the cancer contrast enhancement particle 20 is crushed. In contrast, the crushing frequency fb for the blood vessel contrast enhancement particle 10 is set to be higher than the frequency ft to prevent the blood vessel contrast enhancement particle 10 from being crushed, together with the cancer contrast enhancement particle 20, by the application of an crushing ultrasonic wave of the frequency ft. It is possible to selectively crush the blood vessel contrast enhancement particle 10 and the cancer contrast enhancement particle 20 by setting the crushing frequency for only one of the blood vessel contrast enhancement particle 10 and the cancer contrast enhancement particle 20 to be lower than the frequency ft in this manner.

A typical procedure for ultrasonic imaging of the reperfusion of the cancer contrast enhancement particle 20 to a cancer tissue as an observation target will be described below with reference to FIGS. 24, 25, and 26.

FIG. 24 is a view schematically showing the behaviors of the blood vessel contrast enhancement particles 10 and cancer contrast enhancement particles 20 in the stage of accumulation of the cancer contrast enhancement particles 20 in a cancer tissue. FIG. 25 is a view schematically showing the behaviors of the blood vessel contrast enhancement particles 10 and cancer contrast enhancement particles 20 in the stage of transmission of crushing ultrasonic waves. FIG. 26 is a view schematically showing the behaviors of the blood vessel contrast enhancement particles 10 and cancer contrast enhancement particles 20 in the stage of accumulation of the cancer contrast enhancement particles 20 in a cancer tissue.

As shown in FIG. 24, when the contrast agent according to this embodiment, which contains the blood vessel contrast enhancement particles 10 and the cancer contrast enhancement particles 20, is injected into a blood vessel, the blood vessel contrast enhancement particles 10 and the cancer contrast enhancement particles 20 flow in the blood vessel. The blood vessel contrast enhancement particles 10 have a particle size larger than the vascular endothelial cell gap Ga at the time of the occurrence of the EPR effect, and hence keep flowing in the blood vessel. The cancer contrast enhancement particles 20 have a particle size smaller than the gap Ga, and hence are accumulated in the cancer tissue through a stromal cell system upon passing through the gaps Ga. The imaging control unit controls the transmission unit and the reception unit to scan the imaging region including the blood vessel and cancer tissue of the subject with ultrasonic waves. At the stage shown in FIG. 24, the transmission frequency of ultrasonic waves transmitted by the transmission unit 831 is set to be lower than the frequency ft of crushing ultrasonic waves because the purpose of the transmission of the ultrasonic waves is not to crush the cancer contrast enhancement particles 20 but to ultrasonically scan the imaging region. The image generation unit 53-3 generates an ultrasonic image, in real time, which expresses the spatial distribution of acoustic impedance differences in the imaging region, based on a reception signal from the reception unit 833. The display unit 55 displays the ultrasonic image on a display device in real time. In an early stage of injection of the blood vessel contrast enhancement particles 10 and cancer contrast enhancement particles 20, it is possible to observe the flows of the blood vessel contrast enhancement particles 10 and cancer contrast enhancement particles 20 on an ultrasonic image. That is, it is possible to observe how the cancer contrast enhancement particles 20 are perfused to the cancer tissue on the ultrasonic image.

As shown in FIG. 25, after the blood vessel contrast enhancement particles 10 and the cancer contrast enhancement particles 20 are injected, the blood vessel in an imaging region is filled with the blood vessel contrast enhancement particles 10, and the cancer tissue is filled with the cancer contrast enhancement particles 20. In this case, the luminance values of the ultrasonic image are in a saturated state, and hence it is difficult to observe the flows of the blood vessel contrast enhancement particles 10 and cancer contrast enhancement particles 20 on the ultrasonic image. The user issues an instruction to transmit crushing ultrasonic waves via the input unit 56 or the like of the ultrasonic diagnostic apparatus for the purpose of observing the reperfusion of the cancer contrast enhancement particles 20 to the cancer tissue. Upon receiving the instruction to transmit crushing ultrasonic waves, the imaging control unit 85 transmits crushing ultrasonic waves having the frequency ft to the imaging region from the ultrasonic probe 81. Upon transmitting the crushing ultrasonic waves, the imaging control unit 85 controls the transmission unit 831 and the reception unit 833 to scan again the imaging region with ultrasonic waves having a frequency lower than the frequency ft. An image generation unit 85-3 generates an ultrasonic image in real time based on a reception signal from the reception unit 833. The display unit 55 displays the ultrasonic image on the display device in real time. The cancer contrast enhancement particles 20 existing in the imaging region are crushed upon reception of crushing ultrasonic waves and disappear from the blood vessel. In contrast to this, the blood vessel contrast enhancement particles 10 existing in the imaging region are not crushed even upon receiving crushing ultrasonic wave, and hence keep flowing in the blood vessel. Consequently, the cancer contrast enhancement particles 20 are not depicted on an ultrasonic image immediately after the transmission of crushing ultrasonic waves, and only the blood vessel contrast enhancement particles 10 are depicted. Note that in the above description, crushing ultrasonic waves are transmitted in response to the reception of a transmission start instruction issued by the user via the input unit 56. However, the ultrasonic diagnostic apparatus may automatically transmit crushing ultrasonic waves at a predetermined timing.

As shown in FIG. 26, when crushing ultrasonic waves are transmitted, the cancer contrast enhancement particles 20 begin to be accumulated in the cancer tissue via the stromal system upon passing through vascular endothelial cell gaps. That is, the cancer contrast enhancement particles 20 begin to reperfuse to the cancer tissue. After the transmission of crushing ultrasonic waves, therefore, the blood vessel contrast enhancement particles 10 (i.e., the vascular system) are depicted on an ultrasonic image with high luminance, and the reperfusion of the cancer contrast enhancement particles 20 to the cancer tissue is depicted. This allows the user to observe the reperfusion of the cancer contrast enhancement particles 20 to the cancer tissue on the ultrasonic image.

Another operation example of the ultrasonic diagnostic apparatus 80 according to this embodiment will be described next. The ultrasonic diagnostic apparatus according to the embodiment differentiates a diseased tissue region by using the difference in time concentration curve between the blood vessel contrast enhancement particles 10 and the cancer contrast enhancement particles 20. An operation example associated with the differentiation of a diseased tissue region which is performed under the control of the system control unit 51 will be described below.

Figure 27:
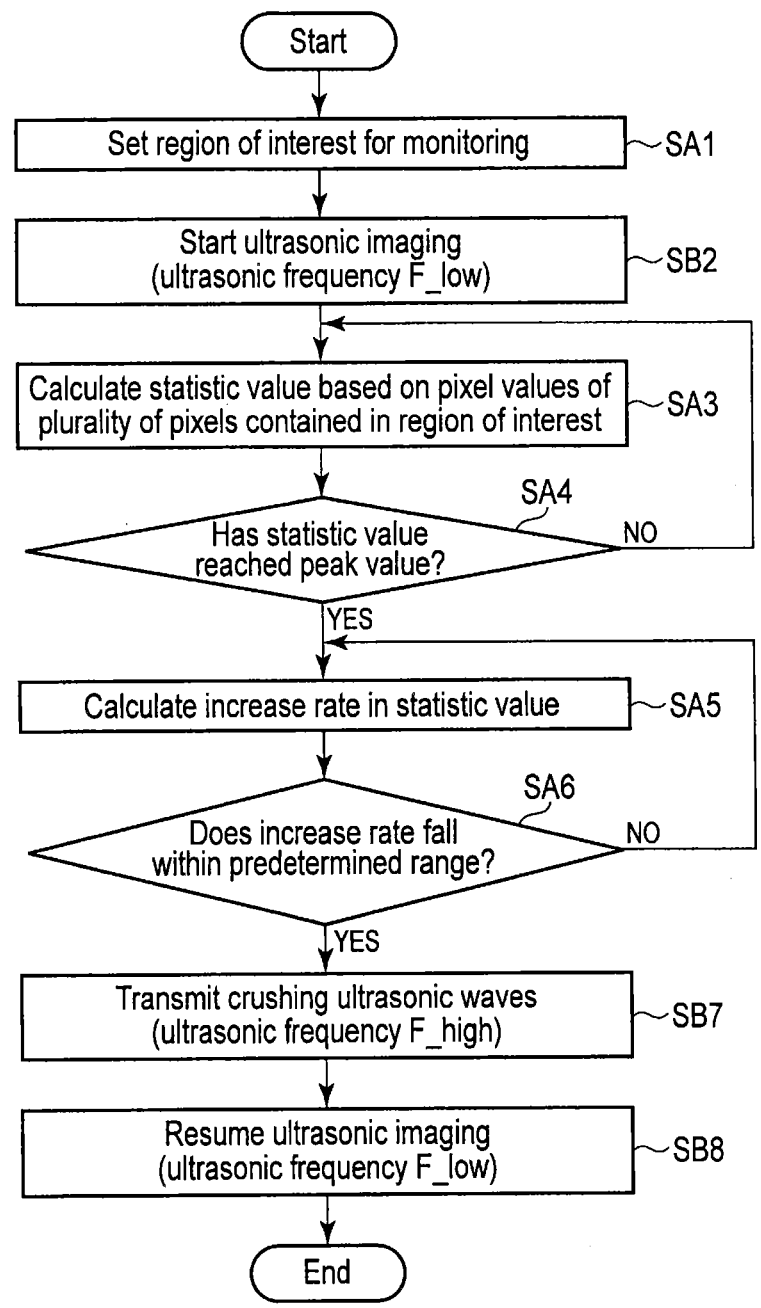
FIG. 27 is a flowchart showing a typical procedure for an operation associated with the differentiation of a diseased tissue region under the control of a system control unit in FIG. 21.

FIG. 27 is a flowchart showing a typical procedure for the operation associated with the differentiation of a diseased tissue region which is performed under the control of the system control unit 51. The same step numbers as those in FIG. 13 denote the steps with the same processing contents, and a detailed description of them will be omitted. FIG. 28 is a view showing, side by side, the time concentration curve of a contrast agent according to this embodiment and a temporal change in ultrasonic frequency.

As shown in FIG. 27, at a stage prior to imaging, the system control unit 51 causes the image analysis unit 54 to perform setting processing of a region of interest (step SA1). In step SA1, the image analysis unit 54 sets a region of interest for monitoring on a predetermined medical image in accordance with an instruction from the user via the input unit 56. A region of interest is set in a local region including a treatment region such as a cancer tissue. After the region of interest is set, the contrast agent according to this embodiment is injected into the subject S. When preparations for imaging are made, the user inputs an imaging start instruction via the input unit 56.

Upon receiving the imaging start instruction, the system control unit 51 causes the imaging unit 52-3 to start ultrasonic imaging (step SB2). In step SB2, the imaging unit 52-3 causes the transmission/reception unit 83 of the imaging unit 52-3 to image the subject with ultrasonic waves via the ultrasonic probe 81. The transmission unit 831 transmits ultrasonic waves having an ultrasonic frequency for imaging. The ultrasonic frequency for imaging is set to a frequency F_low which cannot crush both the blood vessel contrast enhancement particles 10 and the cancer contrast enhancement particles 20. The frequency F_low can be arbitrarily set by the user or the like via the input unit 56. The reception unit 833 receives the ultrasonic waves reflected by the subject S and converts the ultrasonic waves into echo signals. The signal processing unit 87 converts the echo signals from the reception unit 833 into B-mode signals. The image generation unit 53-3 repeatedly generates ultrasonic images based on the B-mode signals. The display unit 55 displays the repeatedly generated medical images.

Upon performing step SB2, the system control unit 51 causes the image analysis unit 54 to perform statistical value calculation processing (step SA3).

Upon performing step SA3, the system control unit 51 causes the image analysis unit 54 to perform determination processing (step SA4). In step SA4, the image analysis unit 54 determines whether the average value calculated in step SA3 has reached the peak value (step SA5). If it is determined that the average value has not reached the peak value (step SA4: NO), the system control unit 51 advances to step SA3 to repeat steps SA3 and SA4 for the latest medical image until it is determined that the average value has reached the peak value. For example, the image analysis unit 54 records the average value calculated in step SA3 in chronological order. If the average value has changed to a smaller value, the image analysis unit 54 determines that the average value has reached the peak.

If it is determined that the average value has reached the peak value (step SA4: YES), the system control unit 51 causes the image analysis unit 54 to perform calculation processing for an increase rate (step SA5).

Upon performing step SA5, the system control unit 51 causes the image analysis unit 54 to perform determination processing (step SA6). In step SA6, the image analysis unit 54 determines whether the increase rate calculated in step SA5 falls within a predetermined range. If it is determined that the increase rate does not fall within the predetermined range (step SA6: NO), the system control unit 51 advances to step SA5 to repeat steps SA5 and SA6 with respect to the latest medical image until it is determined that the increase rate has fallen within the predetermined range.

If it is determined that the increase rate has fallen within the predetermined range (step SA6: YES), the system control unit 51 causes the imaging unit 52-3 to transmit crushing ultrasonic waves (step SB7). In step SB7, the transmission unit 831 of the imaging unit 52 transmits crushing ultrasonic waves having a frequency F_high which can crush the blood vessel contrast enhancement particles 10 to the subject. The blood vessel contrast enhancement particles 10 which have received crushing ultrasonic waves are crushed. This almost completely eliminates the blood vessel contrast enhancement particles 10 retained in the blood vessel. As a consequence, only the contrast agent (cancer contrast enhancement particles 20) for a stromal system such as a cancer tissue is retained. Crushing ultrasonic waves are transmitted only for a predetermined time Δt. The time Δt is set to a time enough to crush the blood vessel contrast enhancement particles 10 retained in the blood vessel. The user or the like can arbitrarily set the frequency F_high via the input unit 56.

Upon performing step SB7, the system control unit 51 causes the imaging unit 52-3 to resume ultrasonic imaging (step SB8). In step SB8, the transmission/reception unit 83 of the imaging unit 52-3 images again the subject S with ultrasonic waves having the frequency F_low via the ultrasonic probe 81 upon transmitting ultrasonic waves having the frequency F_high. As shown in FIG. 28, ultrasonic imaging in step SB8 is performed in a plateau period during which the stromal system such as the cancer tissue is continuously filled with the cancer contrast enhancement particles 20. In step SB7, the blood vessel contrast enhancement particles 10 are eliminated from the vascular system by the transmission of crushing ultrasonic waves. Therefore, no contrast-enhanced blood vessel region is depicted on the ultrasonic image generated in step SB8, but only a contrast-enhanced cancer tissue region is depicted on the image. This allows the user to easily differentiate the cancer tissue.

(Magnetic Resonance Imaging Apparatus)

Figure 29:
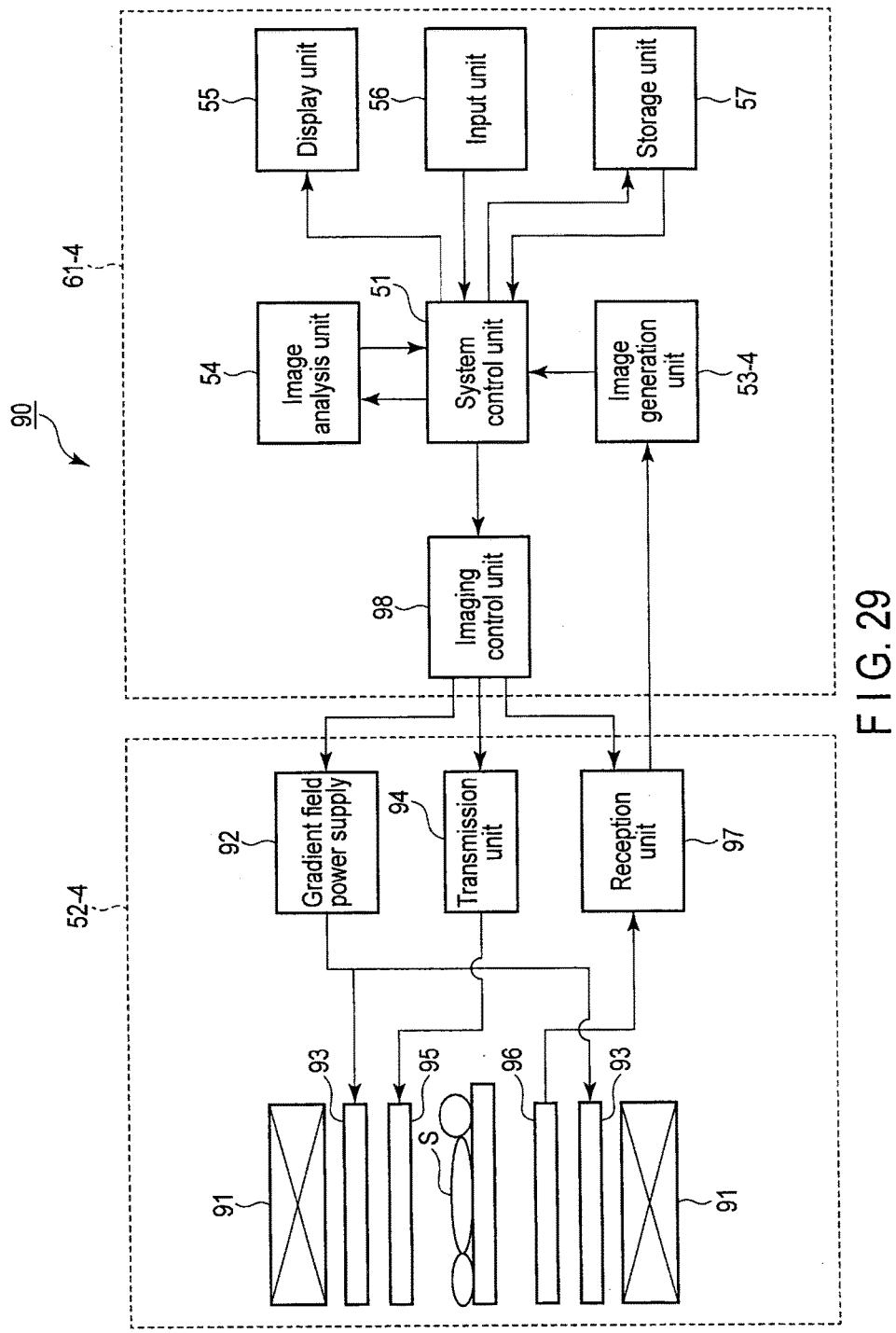
FIG. 29 is a block diagram showing the arrangement of a magnetic resonance diagnostic apparatus according to this embodiment.

FIG. 29 is a block diagram showing the arrangement of a magnetic resonance Imaging apparatus 90 according to this embodiment. As shown in FIG. 29, the magnetic resonance Imaging apparatus 90 includes an imaging unit 52-4 and a console 61-4. The imaging unit 52-4 includes a static field magnet 91, a gradient field power supply 92, a gradient field coil 93, a transmission unit 94, a transmission RF coil 95, a reception RF coil 96, and a reception unit 97.

The static field magnet 91 has a nearly cylindrical hollow shape and generates a static magnetic field in the nearly cylindrical interior. A spatial area in which the uniformity of a generated magnetic field is high is used for imaging. As the static field magnet 91, for example, a permanent magnet or superconductive magnet is used.

The gradient field power supply 92 supplies a current to the gradient field coil 93 in accordance with a control signal supplied from an imaging control unit 98 in the console 61-4. The gradient field power supply 92 causes the gradient field coil 93 to generate a gradient magnetic field by supplying a current to the gradient field coil 93. The gradient field coil 93 is mounted inside the static field magnet 91. The gradient field coil 93 generates a gradient magnetic field in accordance with a current supplied from the gradient field power supply 92. A gradient magnetic field is generated to add positional information to a magnetic resonance signal (to be referred to as an MR signal hereinafter). More specifically, a gradient magnetic field includes a slice selection gradient magnetic field, a phase encoding gradient magnetic field, and a readout gradient magnetic field. A slice selection gradient magnetic field is used to arbitrarily determine an imaging slice. A phase encoding gradient magnetic field is used to encode the phase of an MR signal in accordance with the spatial position. A readout gradient magnetic field is used to encode the frequency of an MR signal in accordance with the spatial position.

A top on which the subject S is place is inserted into the bore inside the static field magnet 91. A contrast agent (to be referred to as an MR contrast agent hereinafter) according to this embodiment which is used for the magnetic resonance diagnostic apparatus 90 is injected into the subject S.

The transmission unit 94 transmits, to the subject S, an RF magnetic field for exciting target atomic nuclei existing in the subject S via the transmission RF coil 95. As target atomic nuclei, protons are typically used. More specifically, the transmission unit 94 supplies an RF signal (Radio Frequency signal) for exciting target atomic nuclei to the transmission RF coil 95 in accordance with a control signal supplied from the imaging control unit 98.

The transmission RF coil 95 is arranged on the inner circumferential side of the gradient field coil 93. The transmission RF coil 95 generates an RF magnetic field upon receiving an RF pulse from the transmission unit 94. The generated RF magnetic field oscillates at a resonant frequency unique to target atomic nuclei to excite the target atomic nuclei.

The reception RF coil 96 is arranged on the inner circumferential side of the gradient field coil 93. The reception RF coil 96 electromagnetically detects electromagnetic waves generated from the excited target atomic nuclei, and generates an analog electrical signal corresponding to the energy of the detected electromagnetic waves. The generated electrical signal is called an MR signal. The MR signal is supplied to the reception unit 97.

The reception unit 97 receives an MR signal corresponding to the energy of the electromagnetic waves generated from the excited target atomic nuclei by the reception RF coil 96. More specifically, the reception unit 97 receives an MR signal from the reception RF coil 96 in accordance with a control signal supplied from the imaging control unit 98. The reception unit 97 then generates a digital MR signal by processing the received MR signal.

The console 61-4 includes an imaging control unit 98, an image generation unit 53-4, an image analysis unit 54, a display unit 55, an input unit 56, a storage unit 57, and a system control unit 51.

To execute MR imaging based on a predetermined imaging principle for the subject S, the imaging control unit 98 controls the gradient field power supply 92, the transmission unit 94, and the reception unit 97 in accordance with a pulse sequence corresponding to the predetermined imaging principle. Any existing imaging method which can use an MR contrast agent can be applied to MR imaging according to this embodiment. For example, as imaging methods according to the embodiment, an imaging method using the difference in longitudinal relaxation time T1 or transverse relaxation time T2 and an imaging method using a CEST (Chemical Exchange Saturation Transfer) effect are suitably used.

The image generation unit 53-4 generates an MR image corresponding to the imaging principle used for MR imaging based on an MR signal from the reception unit 97. The display unit 55 displays the MR image.

A specific example of the MR contrast agent according to this embodiment will be described below. As described above, the magnetic resonance diagnostic apparatus 90 can use a plurality of imaging principles in accordance with imaging purposes. Such imaging principles include an imaging principle using the difference in longitudinal relaxation time T1 or transverse relaxation time T2 and an imaging principle using the CEST effect. Different contrast enhancement materials are used in accordance with different imaging principles.

1. In imaging using the difference in T1 or T2, a contrast enhancement material having the effect of shortening T1 or T2 is used. Note that imaging using the difference in T1 is called T1-weighted imaging, and generates a T1-weighted image. Imaging using the difference in T2 is called T1-weighted imaging, and generates a T1-weighted image. As such a contrast enhancement material, a paramagnetic metal, SPIO (Superparamagnetic iron oxide particle), or the like is used. As a paramagnetic metal, gadolinium Gd or manganese Mn is used. Metals having different contrast enhancement effects are preferably selected, as needed, from the respective paramagnetic metals or superparamagnetic iron oxide particles as the contrast enhancement materials for the blood vessel contrast enhancement particle 10 and the cancer contrast enhancement particle 20. Note that as contrast enhancement materials for the blood vessel contrast enhancement particle 10 and the cancer contrast enhancement particle 20, contrast enhancement materials having different resonant frequencies instead of contrast enhancement materials having the effect of shortening T1 or T2 may be used.

2. In imaging using the CEST effect (to be referred to as CEST imaging hereinafter), a compound containing a paramagnetic metal which can be an exogenous contrast agent is used as a contrast enhancement material. A compound containing a paramagnetic metal aimed at CEST imaging is called a PARACEST contrast agent. As this paramagnetic metal, it is preferable to use a paramagnetic metal belonging to the lanthanoid elements including europium Eu, terbium Tb, dysprosium Dy, ytterbium Yb, and thulium Tm. Metals having different contrast enhancement effects are preferably selected, as needed, from the above paramagnetic metals belonging to the lanthanoid elements as a paramagnetic metal for the blood vessel contrast enhancement particle 10 and a paramagnetic metal for the cancer contrast enhancement particle 20. The mechanism of an endogenous contrast agent will be described as an explanation of a general CEST effect. When the proton H (for example, the proton H of $-NH_2$ (amide group)) of a compound contained in an endogenous contrast agent is continuously excited at a resonant frequency corresponding to the proton, magnetic energy is exchanged between a proton of the endogenous contrast agent and a proton of free water according to the chemical exchange phenomenon. This magnetic energy exchange will decrease the intensity of MR signals from the protons of the free water. This is a phenomenon called the CEST effect. In an exogenous contrast agent (PARACEST contrast agent), direct magnetic energy exchange between the protons of free water and the paramagnetic metal in the exogenous contrast agent will decrease the intensity of MR signals from the protons of the free water as described above. It is known that the CEST imaging is higher in detection sensitivity than conventional MR spectroscopy by at least 10 times or more.

When a liposome is to be used as a carrier, a contrast enhancement material is preferably contained in the liposome or bonded to its surface. If a contrast enhancement material has toxicity, since a lipid bilayer membrane itself has a structure which reduces the toxicity, the contrast enhancement material is preferably contained in the liposome. In order to further reduce the toxicity, the contrast enhancement material may be synthesized into a compound having a chelate structure by using a chelator, and the contrast enhancement material having the chelate structure may be contained in the liposome. Alternatively, the contrast enhancement material may be synthesized with a simpler compound which can reduce the toxicity, and the synthetic compound may be contained in the liposome. When a polymer micelle is to be used as a carrier, a contrast enhancement material having the above chelate structure is preferably reacted with a block copolymer, and the contrast enhancement material having a chelate structure is preferably contained in the polymer micelle. When a dendrimer is to be used as a carrier, the contrast enhancement material having a chelate structure is bonded to the functional group at the terminal of a dendron.

Note that when the same material is used as the contrast enhancement materials for the blood vessel contrast enhancement particles 10 and the cancer contrast enhancement particles 20, it is not possible to perform frequency discrimination between an MR signal from the contrast enhancement material for the blood vessel contrast enhancement particles 10 and an MR signal from the contrast enhancement material for the cancer contrast enhancement particles 20. In this case, it is impossible to perform simultaneous imaging including vascular system imaging and stromal system imaging so as to visually discriminate a contrast-enhanced blood vessel region from a contrast-enhanced cancer tissue region on an MR image. When performing simultaneous imaging so as to visually discriminate a contrast-enhanced blood vessel region from a contrast-enhanced cancer tissue region on an MR image, different types of contrast enhancement materials among the above contrast enhancement materials are preferably used as the contrast enhancement materials for the blood vessel contrast enhancement particles 10 and the cancer contrast enhancement particles 20. A specific example of an imaging method when using different types of contrast enhancement materials as the contrast enhancement materials for the blood vessel contrast enhancement particles 10 and the cancer contrast enhancement particles 20 will be described below.

1. When contrast enhancement materials different in relaxation time such as T1 or T2 are used as the contrast enhancement materials for the blood vessel contrast enhancement particles 10 and the cancer contrast enhancement particles 20, the imaging control unit 98 executes MR imaging in accordance with a multispin echo sequence. In the multispin echo sequence, the imaging control unit 98 applies various types of pulses so as to make an echo time TE for the contrast enhancement material for the blood vessel contrast enhancement particles 10 differ from the echo time TE for the contrast enhancement material for the cancer contrast enhancement particles 20. This makes it possible to generate an MR signal (spin echo) from the blood vessel contrast enhancement particles 10 and an MR signal (spin echo) from the cancer contrast enhancement particles 20 at different timings. The reception unit 833 repeatedly receives MR signals from the blood vessel contrast enhancement particles 10 and the cancer contrast enhancement particles 20 via the reception RF coil 96. A plurality of MR signals originating from the blood vessel contrast enhancement particles 10 will be referred to as the first signal sequence. A plurality of MR signals originating from the cancer contrast enhancement particles 20 will be referred to as the second signal sequence. The image generation unit 53-4 generates a T1-weighted image or T2-weighted image based on the first signal sequence from the reception unit 97. The generated T1-weighted image or T2-weighted image is a blood vessel emphasized image on which a contrast-enhanced blood vessel is more emphasized than a contrast-enhanced cancer tissue. Likewise, the image generation unit 53-4 generates a T1-weighted image or T2-weighted image based on the second signal sequence from the reception unit 97. The generated T1-weighted image or T2-weighted image is a cancer tissue emphasized image on which a contrast-enhanced cancer tissue region is more emphasized than a contrast-enhanced blood vessel region. The display unit 55 displays the blood vessel emphasized image and the diseased tissue emphasized image. As described above, this imaging method can implement simultaneous imaging including vascular system imaging and stromal system imaging of a cancer tissue so as to make a contrast-enhanced blood vessel region and a contrast-enhanced cancer tissue region visually discriminable.

2. When using contrast enhancement materials different in resonant frequency as the contrast enhancement materials for the blood vessel contrast enhancement particles 10 and the cancer contrast enhancement particles 20, the imaging control unit 98 executes MR imaging in accordance with a multispin echo sequence using a water-fat imaging method. In this case, the contrast enhancement material for the blood vessel contrast enhancement particles 10 has the first proton having the first resonant frequency, and the contrast enhancement material for the cancer contrast enhancement particles 20 has the second proton having the second resonant frequency. The first resonant frequency differs from the second resonant frequency on the order of several ppm. The imaging control unit 98 applies a 180° pulse at the timing when the first proton becomes in phase of the second proton at the echo center in the first sequence in the multispin echo sequence, and applies a 180° pulse at the timing when the first proton becomes out of phase with the second proton at the echo center in the second sequence. Applying pulses at such timings makes the phase of the first proton coincide with the phase of the second proton at the time of the generation of an MR signal (spin echo) in the first sequence, and makes the phase of the first proton opposite to the phase with the second proton at the time of the generation of an MR signal (spin echo) in the second sequence. The reception unit 97 repeatedly receives MR signals via the reception RF coil 96 when the first and second protons become in phase with each other, and repeatedly receives MR signals when the first and second protons become out of phase with each other. In the following description, a plurality of MR signals generated when the first and second protons become in phase with each other will be referred to as the first signal sequence, and a plurality of MR signals generated when the first and second protons become out of phase with each other will be referred to as the second signal sequence. The image generation unit 53-4 generates an in-phase image based on the first MR signal sequence, and generates an out-of-phase image based on the second MR signal sequence. The image generation unit 53-4 generates a cancer tissue emphasized image and a blood vessel emphasized image based on the in-phase image and the out-of-phase image. The display unit 55 displays the cancer tissue emphasized image and the blood vessel emphasized image. As described above, this imaging method can implement simultaneous imaging including vascular system imaging and stromal system imaging of a cancer tissue so as to visually discriminate a contrast-enhanced blood vessel region from a contrast-enhanced cancer tissue region.

3. When individually executing vascular system imaging and stromal system imaging, the imaging control unit 98 executes MR imaging for vascular system imaging and MR imaging for stromal system imaging in different time zones. It is preferable to use materials in accordance with each imaging method for the contrast enhancement materials for the blood vessel contrast enhancement particles 10 and the cancer contrast enhancement particles 20. For example, an MR angiography method with a relatively high time resolution is used as vascular system imaging, whereas a CEST imaging method with high detection sensitivity is used as stromal system imaging. The MR angiography method is an imaging method using the difference in T1 or T2. In the case of the MR angiography method, it is preferable to select a contrast enhancement material for the blood vessel contrast enhancement particles 10 from the above paramagnetic metals and superparamagnetic iron oxide particles. In the case of the CEST imaging method, it is preferable to select a contrast enhancement material for the cancer contrast enhancement particles 20 from paramagnetic metals belonging to the lanthanoid elements. The image generation unit 53-4 generates a blood vessel emphasized image based on the MR signal sequence acquired by MR angiography via the reception unit 97, and generates a cancer tissue emphasized image based on the MR signal sequence acquired by CEST imaging via the reception unit 97. The display unit 55 displays the blood vessel emphasized image and the cancer tissue emphasized image. As described above, this imaging method can implement vascular system imaging and stromal system imaging of a cancer tissue by individual imaging.

Note that as stromal system imaging, for example, diffusion-weighted imaging may be used instead of T1-weighted imaging for obtaining a T1-weighted image or T2-weighted imaging for obtaining a T2-weighted image. In diffusion-weighted imaging, the imaging control unit 98 applies MPG (motion probing gradient) pulses to measure the diffusion of water. The image generation unit 53-4 generates a diffusion-weighted image of the contrast enhancement material for the cancer contrast enhancement particles 20 flowing into a diseased tissue based on the MR signals acquired by the reception unit 97 in diffusion-weighted imaging. A signal intensity S(b) in diffusion-weighted imaging is expressed by equation (1) given below. Let b be the intensity of an MPG which causes phase diffusion inside a pixel by diffusion, and ADC be an apparent diffusion coefficient.

$$S(b)=S(0)*\exp(-b*ADC) \quad (1)$$

As indicated by equation (1), the signal intensity S(b) depends on not only the apparent diffusion coefficient ADC and the b value but also the signal intensity of S(0). When S(0) increases, the signal intensity S increases regardless of an increase or decrease in ADC. This phenomenon is called a T2 shine through phenomenon. In many lesions, the T2 value extends, and the ADC value decreases. Along with this, a diffusion-weighted image becomes a high signal. Relatively reducing the influence of S(0) on the signal intensity S(b) by setting the b value to a large value can more reflect the ADC value in a diffusion-weighted image.

Note that in order to increase the b value, it is necessary to apply a strong gradient magnetic field. If, however, the imaging unit 52-4 does not have any arrangement capable of applying a strong gradient magnetic field, the quantification of diffusion-weighted imaging is obstructed by the T2 shine through phenomenon on a T2-weighted image on which a blood vessel emphasized image becomes a high signal. That is, when the b value is low, it is impossible to obtain an image concerning the stromal system of a diseased tissue with high quantitativeness. That is, T1-weighted imaging is suitable as stromal system imaging.

(PET Apparatus)

A PET apparatus according to this embodiment simultaneously measures a pair of 512-keV gamma rays generated upon pair annihilation of each of positrons generated from radionuclides accumulated in an subject and a corresponding one of electrons existing around the radionuclides, thereby generating an image expressing the spatial concentration distribution of the radionuclides. A contrast enhancement material for PET imaging may be any type of radionuclide which can emit positrons. It is preferable to use, as a contrast enhancement material for PET imaging, $^{18}$F which is the radionuclide of fluorine, $^{11}$C which is the radionuclide of carbon, or the like. As a carrier, it is possible to use any of a liposome, polymer micelle, and dendrimer which can contain the radionuclide. When the contrast enhancement material is to be contained in a liposome, the contrast enhancement material is preferably contained in the liposome upon being synthesized with a suitable compound for the purpose of, for example, a reduction in the toxicity of the contrast enhancement material. When the contrast enhancement material is to be bonded to the surface of a liposome, the contrast enhancement material is preferably bonded to the surface of the liposome upon being synthesized with a suitable compound for the purpose of, for example, a reduction in the toxicity of the contrast enhancement material. When the contrast enhancement material is to be contained in a polymer micelle, the contrast enhancement material is contained in the polymer micelle upon being reactively synthesized with the hydrophobic segment of a block copolymer. When using a dendrimer, the contrast enhancement material is bonded to the functional group at the terminal of a dendron.

The energy of all pair annihilation gamma rays detected by the PET apparatus remains 512 keV regardless of the types of radionuclides. Even if different types of radionuclides are allocated to the contrast enhancement materials for the blood vessel contrast enhancement particles 10 and the cancer contrast enhancement particles 20, it is not possible to discriminate pair annihilation gamma rays originating from the contrast enhancement material for the blood vessel contrast enhancement particles 10 from pair annihilation gamma rays originating from the contrast enhancement material for the cancer contrast enhancement particles 20.

The above PET contrast agent is injected into a subject, and PET imaging is performed. In PET imaging, simultaneous imaging including vascular system imaging and stromal system imaging is performed. By performing simultaneous imaging, the PET apparatus can generate a blood vessel/cancer tissue emphasized image on which both a contrast-enhanced blood vessel region and a contrast-enhanced cancer tissue region are emphasized.

(SPECT Apparatus)

A SPECT apparatus according to this embodiment detects single photon gamma rays generated from radionuclides accumulated in a subject to generate an image expressing the spatial concentration distribution of the radionuclides. A contrast enhancement material for SPECT imaging may be any type of radionuclide which can emit single photon gamma rays. It is preferable to use, as a contrast enhancement material for SPECT imaging, $^{99m}$Tc which is the radionuclide of technetium, $^{201}$Tl which is the radionuclide of thallium, or the like. The energy of a single photon gamma ray varies in accordance with the type of radionuclide which emits the single photon gamma ray. As a carrier, it is possible to use any of a liposome, polymer micelle, and dendrimer which can contain the radionuclide. When the contrast enhancement material is to be contained in a liposome, the contrast enhancement material is preferably contained in the liposome upon being synthesized with a suitable compound for the purpose of, for example, a reduction in the toxicity of the contrast enhancement material. When the contrast enhancement material is to be bonded to the surface of a liposome, the contrast enhancement material is preferably bonded to the surface of the liposome upon being synthesized with a suitable compound for the purpose of, for example, a reduction in the toxicity of the contrast enhancement material. When the contrast enhancement material is to be contained in a polymer micelle, the contrast enhancement material is contained in the polymer micelle upon being reactively synthesized with the hydrophobic segment of a block copolymer. When using a dendrimer, the contrast enhancement material is bonded to the functional group at the terminal of a dendron.

The energies of single photon gamma rays detected by the SPECT apparatus vary for the respective radionuclides. It is therefore possible to discriminate vascular system imaging from stromal system imaging by allocating different radionuclides among the above radionuclides to the contrast enhancement materials for the blood vessel contrast enhancement particles 10 and the cancer contrast enhancement particles 20. This makes it possible to visually discriminate a contrast-enhanced blood vessel region and a contrast-enhanced cancer tissue region on a SPECT image. Note that vascular system imaging and stromal system imaging may be performed by simultaneous imaging or individual imaging.

(X-Ray Diagnostic Apparatus)

An X-ray diagnostic apparatus according to this embodiment may be of a current integration type or photon counting type. The X-ray diagnostic apparatus of the current integration type irradiates a subject with X-rays from an X-ray tube at a desired imaging angle, and detects the X-rays transmitted through the subject by using an X-ray detector. The X-ray diagnostic apparatus of the current integration type generates an image expressing the spatial distribution of the X-ray attenuation coefficients of substances on the X-ray transmission path. The contrast enhancement mechanism of a contrast agent in the current integration type is similar to that of a CT contrast agent. As a contrast enhancement material for the contrast agent in the current integration type, it is preferable to use a heavy metal having a high X-ray attenuation coefficient such as iodine I. As a carrier, it is possible to use any of liposome, polymer micelle, and dendrimer which can contain a heavy metal having an X-ray attenuation coefficient or to which it can be bonded.

The X-ray diagnostic apparatus of the photon counting type irradiates a subject with X-rays from an X-ray tube at a desired imaging angle, detects the X-rays transmitted through the subject by using an X-ray detector, and counts the number of detected X-ray photons for each energy band. The X-ray diagnostic apparatus of the photon counting type generates an image expressing the spatial distribution of the numbers of photons for each energy band. The contrast enhancement mechanism of a contrast agent in the photon counting type is similar to that of a PCCT contrast agent. As a contrast enhancement material for a contrast agent in the photon counting type, it is preferable to use a heavy metal or the like having a high X-ray attenuation coefficient, such as iodine I, gadolinium Gd, gold Au, or bismuth Bi. Heavy metals having different contrast enhancement effects are preferably selected, as needed, from iodine I, gadolinium Gd, gold Au, and bismuth Bi as the contrast enhancement materials for the blood vessel contrast enhancement particles 10 and the cancer contrast enhancement particles 20. As a carrier, it is possible to use any of a liposome, polymer micelle, and dendrimer which can contain a heavy metal having a high X-ray attenuation coefficient or to which it can be bonded. Note that gadolinium Gd, gold Au, and bismuth Bi have slight toxicity to the human body, whereas a liposome has the property of being capable of reducing toxicity. For this reason, when gadolinium Gd, gold Au, or bismuth Bi is to be used as a contrast enhancement material, the contrast enhancement material is preferably contained in a liposome. Note that if it is possible to reduce toxicity by a technique other than being contained in a liposome, gadolinium Gd, gold Au, or bismuth Bi may be contained in or bonded to any carrier.

[Composite Type]

A composite type medical image diagnostic apparatus which performs imaging by using the contrast agent according to this embodiment will be described next.

FIG. 30 is a block diagram showing the arrangement of a composite type medical image diagnostic apparatus 150 according to this embodiment. As shown in FIG. 30, the medical image diagnostic apparatus 150 according to the embodiment includes a system control unit 51 as a central unit, an imaging unit 52, an image generation unit 53, an image analysis unit 54, a display unit 55, an input unit 56, and a storage unit 57. The imaging unit 52 includes a first imaging mechanism 152, a second imaging mechanism 153, and an imaging control unit 154.

The first imaging mechanism 152 is an imaging mechanism for performing medical imaging of a subject injected with the contrast agent according to this embodiment. The first imaging mechanism 152 generates output data concerning the subject by performing medical imaging.

The second imaging mechanism 153 is an imaging mechanism for performing medical imaging of a subject injected with the contrast agent according to this embodiment. The second imaging mechanism 153 generates output data concerning the subject by performing medical imaging.

Imaging mechanisms based on different imaging principles are respectively used as the first imaging mechanism 152 and the second imaging mechanism 153. More specifically, as the first imaging mechanism 152 and the second imaging mechanism 153, apparatuses are selected, as needed, from a PCCT apparatus, X-ray CT apparatus, ultrasonic diagnostic apparatus, magnetic resonance diagnostic (MRI) apparatus, PET apparatus, SPECT apparatus, and X-ray diagnostic apparatus.

The imaging control unit 154 controls the first imaging mechanism 152 and the second imaging mechanism 153 to perform medical imaging of a subject injected with the contrast agent according to this embodiment. More specifically, the imaging control unit 154 controls the first imaging mechanism 152 to perform medical imaging of the subject based on the imaging principle of the first imaging mechanism 152. The imaging control unit 154 controls the second imaging mechanism 153 to perform medical imaging of the subject based on the imaging principle of the second imaging mechanism 153. An imaging region of a subject is set to include a blood vessel as a contrast enhancement target for the blood vessel contrast enhancement particles 10 and a cancer tissue as a contrast enhancement target for the cancer contrast enhancement particles 20. The imaging control unit 154 can perform simultaneous imaging and individual imaging including vascular system imaging and stromal system imaging of a cancer tissue. Simultaneous imaging is an imaging method of executing both vascular system imaging and stromal system imaging. In simultaneous imaging, the first imaging mechanism 152 and the second imaging mechanism 153 perform medical imaging concurrently in the same time zone. When performing simultaneous imaging, the first imaging mechanism 152 and the second imaging mechanism 153 may perform medical imaging of different imaging regions or may perform medical imaging of the same imaging region if structurally allowed. Individual imaging is an imaging method of individually executing vascular system imaging and stromal system imaging. When performing individual imaging, the first imaging mechanism 152 and second imaging mechanism 153 individually perform medical imaging in different time zones. In the case of individual imaging, the first imaging mechanism 152 and the second imaging mechanism 153 may perform medical imaging of different imaging regions or may perform medical imaging of the same imaging region.

In this embodiment, vascular system imaging and stromal system imaging are performed based on different imaging principles. Assume that the first imaging mechanism 152 performs vascular system imaging, and the second imaging mechanism 153 performs stromal system imaging. In this case, a contrast enhancement material having a contrast enhancement effect in the imaging principle of the first imaging mechanism 152 is selected, as needed, as the contrast enhancement material for the blood vessel contrast enhancement particles 10, and a contrast enhancement material having a contrast enhancement effect in the imaging principle of the second imaging mechanism 153 is selected, as needed, as the contrast enhancement material for the cancer contrast enhancement particles 20.

Performing vascular system imaging will typically acquire a blood vessel emphasized image on which a contrast-enhanced blood vessel associated with a blood vessel contrast-enhanced by blood vessel contrast enhancement particles 10 is more emphasized than a contrast-enhanced cancer tissue region associated with a cancer tissue contrast-enhanced by the cancer contrast enhancement particles 20. Vascular system imaging is preferably performed at the timing when a target blood vessel is properly contrast-enhanced by the contrast agent. Performing stromal system imaging will typically acquire a cancer tissue emphasized image on which a contrast-enhanced cancer tissue is more emphasized than a contrast-enhanced blood vessel region. Stromal system imaging is preferably performed at the timing when a target cancer tissue is properly contrast-enhanced by the contrast agent. Vascular system imaging and stromal system imaging each may be started at the timing when an imaging start instruction is input via the input unit 56 or may be automatically performed at a predetermined timing.

The imaging unit 52 of the composite type medical image diagnostic apparatus 150 can also sequentially execute vascular system imaging and stromal system imaging in accordance with a temporal change in the concentration of the contrast agent according to this embodiment along with the operation example exemplarily shown in FIG. 13.

The image generation unit 53 generates a blood vessel emphasized image targeting a contrast-enhanced blood vessel based on output data from the first imaging mechanism 152. In addition, the image generation unit 53 generates a cancer tissue emphasized image targeting a contrast-enhanced cancer tissue based on output data from the second imaging mechanism 153. Furthermore, the image generation unit 53 may generate a composite image constituted by a blood vessel emphasized image and a cancer tissue emphasized image.

The image analysis unit 54 performs perfusion analysis on medical images such as a blood vessel emphasized image and a cancer tissue emphasized image. For example, the image analysis unit 54 calculates various types of perfusion indices indicating blood vessel dynamic states by perfusion analysis.

The display unit 55 displays medical images such as a blood vessel emphasized image and a cancer tissue emphasized image on a display device. In this case, the display unit 55 may display a composite image constituted by a blood vessel emphasized image and a cancer tissue emphasized image. The display unit 55 also displays perfusion indices on the display device. As the display device, it is possible to use, for example, a CRT display, liquid crystal display, organic EL display, or plasma display, as needed.

The input unit 56 receives various instructions and information inputs from the user via an input device. For example, the input unit 56 receives an imaging start instruction from the user via an input device. As input devices, it is possible to use a keyboard, mouse, switches, and the like.

The storage unit 57 stores various types of data such as medical images including a blood vessel emphasized image and a cancer tissue emphasized image. The storage unit 57 also stores control programs for the composite type medical image diagnostic apparatus 150.

The system control unit 51 functions as the central unit of the composite type medical image diagnostic apparatus 150. More specifically, the system control unit 51 reads out a control program stored in the storage unit 57, loads the program in the memory, and controls each unit of the composite type medical image diagnostic apparatus 150 in accordance with the loaded control program.

With the above arrangement, the medical image diagnostic apparatus 150 can clearly image the vascular system and stromal system of a cancer tissue by executing imaging using the contrast agent according to this embodiment.

A PCCT/CT apparatus, nuclear medicine imaging/CT apparatus, and nuclear medicine imaging/MRI apparatus as representative examples of the composite type medical image diagnostic apparatus 150 will be individually described next. In the following description, the same reference numerals denote constituent elements having almost the same functions as those included in the composite type medical image diagnostic apparatus 150, and a repetitive description will be made only when required.

(PCCT/CT Apparatus)

FIG. 31 is a block diagram showing the arrangement of a PCCT/CT apparatus 160 according to this embodiment. As shown in FIG. 31, the PCCT/CT apparatus 160 is a composite apparatus constituted by a photon counting CT apparatus and an X-ray computed tomography imaging apparatus. The PCCT/CT apparatus 160 includes a system control unit 51 as a central unit, an X-ray CT imaging mechanism 152-1, a PCCT imaging mechanism 153-1, an imaging control unit 154-1, an image generation unit 53-1, an image analysis unit 54, a display unit 55, an input unit 56, and a storage unit 57.

The X-ray CT imaging mechanism 152-1 is the imaging mechanism of the X-ray computed tomography imaging apparatus and is used for vascular system imaging. The PCCT imaging mechanism 153-1 is the imaging mechanism of the photo counting CT apparatus and is used for stromal system imaging.

Figure 32:
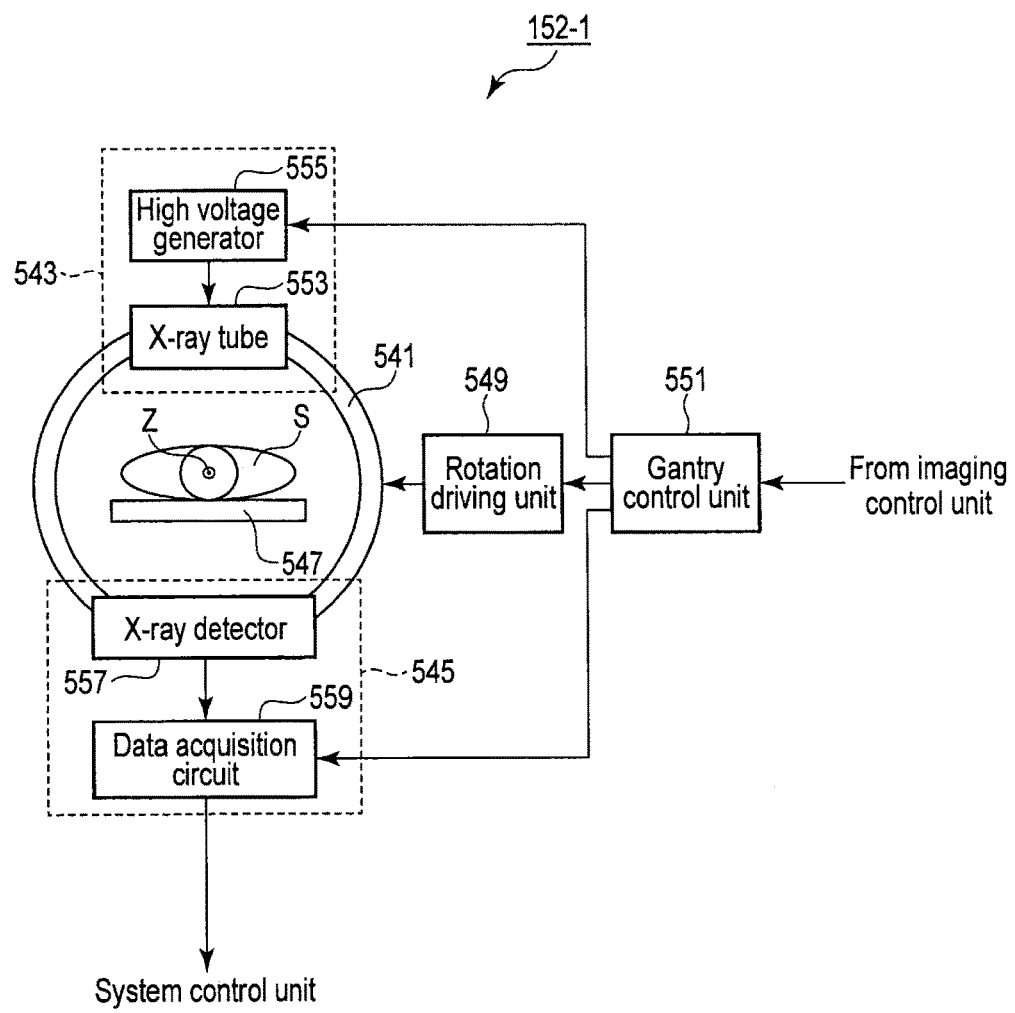
FIG. 32 is a block diagram showing the arrangement of an X-ray CT imaging mechanism in FIG. 31.

FIG. 32 is a block diagram showing the arrangement of the X-ray CT imaging mechanism 152-1. As shown in FIG. 32, the X-ray CT imaging mechanism 152-1 supports a rotating frame 541 having a cylindrical shape so as to allow it to rotate about the rotation axis Z. An X-ray generation unit 543 and an X-ray detection unit 545 are amounted on the rotating frame 541 so as to face each other through the rotation axis Z. The opening portion of the rotating frame 541 is set to an imaging area (FOV). A top 547 is positioned in the opening portion of the rotating frame 541. The subject S is placed on the top 547. The top 547 is moved such that an imaging region of the subject S placed on the top 547 is included in the imaging area. The rotating frame 541 rotates about the rotation axis Z at a constant angular velocity upon receiving power from a rotation driving unit 549. The rotation driving unit 549 generates power for rotating the rotating frame 541 in accordance with a drive signal from a gantry control unit 551.

The X-ray generation unit 543 generates X-rays. More specifically, the X-ray generation unit 543 includes an X-ray tube 553 and a high voltage generator 555. The X-ray tube 553 generates X-rays upon receiving a high voltage and a filament current from the high voltage generator 555. The high voltage generator 555 applies a high voltage to the X-ray tube 553 in accordance with a control signal from the gantry control unit 551, and supplies a filament current to the X-ray tube 553 in accordance with a control signal from the gantry control unit 551.

The X-ray detection unit 545 detects X-rays generated from the X-ray generation unit 543 and transmitted through the subject S and generates digital data corresponding to the energies of the detected X-rays. More specifically, the X-ray detection unit 545 includes an X-ray detector 557 and a data acquisition circuit 559.

The X-ray detector 557 detects X-rays generated from the X-ray tube 553. The X-ray detector 557 is equipped with a plurality of X-ray detection elements arranged two-dimensionally. Each X-ray detection element detects an X-ray from the X-ray tube 553, and generates an electrical signal corresponding to the energy of the detected X-ray.

The data acquisition circuit 559 measures the energies of X-rays detected by the X-ray detector 557 in accordance with a control signal from the gantry control unit 551. More specifically, the data acquisition circuit 559 acquires electrical signals from the respective X-ray detection elements for each view, and converts the acquired electrical signals into digital data. The digital data is called raw data. The raw data is supplied to the image generation unit 53-5 via the system control unit 51.

The gantry control unit 551 comprehensively controls the respective types of devices mounted on the gantry X-ray CT imaging mechanism 152-1 in accordance with instructions from the imaging control unit 154-1. For example, the gantry control unit 551 controls the X-ray generation unit 543, the X-ray detection unit 545, and the rotation driving unit 549 to perform X-ray CT imaging of the subject S injected with the contrast agent according to this embodiment.

In the above description, the X-ray CT imaging mechanism 152-1 is of a rotate/rotate-type. However, the X-ray CT imaging mechanism 152-1 according to this embodiment is not limited to this. For example, the X-ray CT imaging mechanism 152-1 may be of a stationary/rotate-type.

Figure 33:
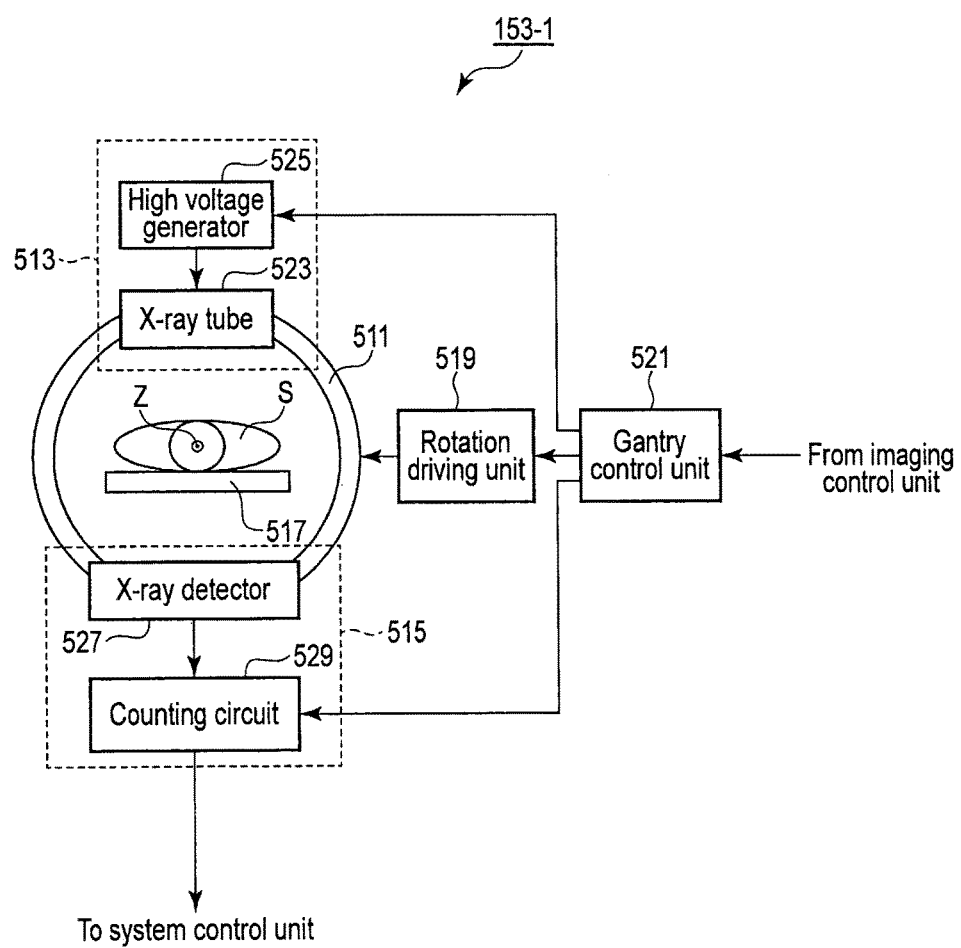
FIG. 33 is a block diagram showing the arrangement of a PCCT imaging mechanism in FIG. 31.

As shown in FIG. 33, the PCCT imaging mechanism 153-1 supports a rotating frame 511 having a cylindrical shape so as to allow it to rotate about the rotation axis Z. An X-ray generation unit 513 and an X-ray detection unit 515 are amounted on the rotating frame 511 so as to face each other through the rotation axis Z. The opening portion of the rotating frame 511 is set to an imaging area (FOV). A top 517 is positioned in the opening portion of the rotating frame 511. The subject S is placed on the top 517. The top 517 is moved such that an imaging region of the subject S placed on the top 517 is included in the imaging area. The rotating frame 511 rotates about the rotation axis Z at a constant angular velocity upon receiving power from a rotation driving unit 519. The rotation driving unit 519 generates power for rotating the rotating frame 511 in accordance with a drive signal from a gantry control unit 521.

The X-ray generation unit 513 generates X-rays. More specifically, the X-ray generation unit 513 includes an X-ray tube 523 and a high voltage generator 525. The X-ray tube 523 generates X-rays upon receiving a high voltage and a filament current from the high voltage generator 525. The high voltage generator 525 applies a high voltage to the X-ray tube 523 in accordance with a control signal from the gantry control unit 521, and supplies a filament current to the X-ray tube 523 in accordance with a control signal from the gantry control unit 521.

The X-ray detection unit 515 detects X-rays generated from the X-ray generation unit 523 and transmitted through the subject S and counts the number of X-ray photons detected. More specifically, the X-ray detection unit 515 includes an X-ray detector 527 and a counting circuit 529.

The X-ray detector 527 detects X-ray photons generated from the X-ray tube 523. The X-ray detector 527 is equipped with a plurality of X-ray detection elements arranged two-dimensionally. Each X-ray detection element detects an X-ray photon from the X-ray tube 523, and generates an electrical pulse (electrical signal) corresponding to the energy of the detected X-ray photon.

The counting circuit 529 counts the number of X-ray photons detected by the X-ray detector 527 in accordance with a control signal from the gantry control unit 521. As counting schemes used by the counting circuit 529, the sinogram mode scheme and the list mode scheme are known.

The gantry control unit 521 comprehensively controls the respective types of devices mounted on the PCCT imaging mechanism 153-1 in accordance with instructions from the system control unit 51. For example, the gantry control unit 521 controls the X-ray generation unit 513, the X-ray detection unit 515, and the rotation driving unit 519 to perform PCCT imaging of the subject S injected with the contrast agent according to this embodiment.

In the above description, the PCCT imaging mechanism 153-1 is of a rotate/rotate-type. However, the PCCT imaging mechanism 153-1 according to this embodiment is not limited to this. For example, the PCCT imaging mechanism 153-1 may be of a stationary/rotate-type.

As shown in FIG. 31, the imaging control unit 154-1 controls the X-ray CT imaging mechanism 152-1 and the PCCT imaging mechanism 153-1 to perform medical imaging of a subject injected with the contrast agent for the PCCT/CT apparatus 160. In this embodiment, the X-ray CT imaging mechanism 152-1 performs vascular system imaging, and the PCCT imaging mechanism 153-1 performs stromal system imaging. For this reason, a material having a contrast enhancement effect in the imaging principle of the X-ray CT imaging mechanism 152-1 is used for the blood vessel contrast enhancement particles 10. A material having a contrast enhancement effect in the imaging principle of the PCCT imaging mechanism 153-1 is used for the cancer contrast enhancement particles 20.

The material for the blood vessel contrast enhancement particles 10 for the X-ray CT imaging mechanism 152-1 is the same as that used when the X-ray computed tomography imaging apparatus 70 described above performs imaging. The material for the cancer contrast enhancement particle 20 for the PCCT imaging mechanism 153-1 is the same as that used when the photon counting CT apparatus 60 described above performs imaging.

After the contrast agent containing the blood vessel contrast enhancement particles 10 and the cancer contrast enhancement particles 20 is injected into a subject, the X-ray CT imaging mechanism 152-1 and the PCCT imaging mechanism 153-1 respectively perform X-ray CT imaging and PCCT imaging at proper timings.

The X-ray CT imaging mechanism 152-1 and the PCCT imaging mechanism 153-1 may have mechanically independent structures or a mechanically integrated structure. When having mechanically independent structures, the X-ray CT imaging mechanism 152-1 and the PCCT imaging mechanism 153-1 cannot image the same region at the same time. In this case, the X-ray CT imaging mechanism 152-1 and the PCCT imaging mechanism 153-1 respectively perform X-ray CT imaging and PCCT imaging sequentially in different time zones. For example, the imaging control unit 154-1 starts X-ray CT imaging by controlling the X-ray CT imaging mechanism 152-1 at the timing when a blood vessel in an imaging region is filled with the blood vessel contrast enhancement particles 10. More specifically, the gantry control unit 551 of the X-ray CT imaging mechanism 152-1 starts X-ray CT by controlling the X-ray generation unit 543, the X-ray detection unit 545, and the rotation driving unit 549. The user can input an imaging start instruction for X-ray CT imaging via the input unit 56 at an arbitrary timing. After the end of X-ray CT imaging, the X-ray CT imaging mechanism 152-1 is retracted from the imaging region, the PCCT imaging mechanism 153-1 is positioned to the imaging region so as to be ready for imaging. The imaging control unit 154-1 then starts PCCT imaging by controlling the PCCT imaging mechanism 153-1 at the timing when a cancer tissue in the imaging region is filled with the cancer contrast enhancement particles 20. More specifically, the gantry control unit 521 of the PCCT imaging mechanism 153-1 controls the X-ray generation unit 513, the X-ray detection unit 515, and the rotation driving unit 519 to perform X-ray CT imaging of the subject. The user can input an imaging start instruction for PCCT imaging via the input unit 56 at an arbitrary timing. Note that the order of execution of X-ray CT imaging and PCCT imaging can be changed. That is, the PCCT imaging mechanism 153-1 may perform PCCT imaging first, and then the X-ray CT imaging mechanism 152-1 may perform X-ray CT imaging.

If the X-ray CT imaging mechanism 152-1 and the PCCT imaging mechanism 153-1 can perform simultaneous imaging, the imaging control unit 154-1 starts simultaneous imaging including X-ray CT imaging and PCCT imaging by controlling the X-ray CT imaging mechanism 152-1 and the PCCT imaging mechanism 153-1 at the timing when the blood vessel in the imaging region is filled with the blood vessel contrast enhancement particles 10 and the cancer tissue in the imaging region is filled with the cancer contrast enhancement particles 20. The user can input an imaging start instruction for simultaneous imaging via the input unit 56 at an arbitrary timing.

The image generation unit 53-5 generates a CT image (blood vessel emphasized image) targeting a contrast-enhanced blood vessel based on raw data from a data acquisition circuit 559 of the X-ray CT imaging mechanism 152-1. More specifically, the image generation unit 53-5 generates projection data by performing preprocessing such as projection conversion for raw data from the data acquisition circuit 559. The image generation unit 53-5 then generates a blood vessel emphasized image by performing reconstruction computation for the generated projection data. The image generation unit 53-5 generates a PCCT image (cancer tissue emphasized image) targeting a contrast-enhanced cancer tissue based on count data from a counting circuit 529 of the PCCT imaging mechanism 153-1. More specifically, the image generation unit 53-5 generates a cancer tissue emphasized image based on the count data of X-ray photons belonging to an energy band corresponding to the contrast enhancement material contained in the cancer contrast enhancement particles 20.

Note that the image generation unit 53-5 may generate a cancer tissue emphasized image indicating the spatial distribution of a contrast-enhanced cancer tissue by a K-edge imaging technique based on the difference in characteristic X-ray (K-absorption edge) between the contrast enhancement material contained in the blood vessel contrast enhancement particles 10 and the contrast enhancement material contained in the cancer contrast enhancement particles 20. K-edge imaging has been described above, and hence a description of it will be omitted.

The image generation unit 53-5 generates a cancer tissue emphasized image by using the above K-edge imaging processing method. The image generation unit 53-5 generates a cancer tissue emphasized image expressing the spatial distribution of the contrast-enhanced cancer tissue contrast-enhanced by the cancer contrast enhancement particles 20 based on the respective counts in two energy bands on the two sides of the K-absorption edge of the contrast enhancement material contained in the cancer contrast enhancement particles 20. Typically, the generated cancer tissue emphasized image does not include any contrast-enhanced blood vessel region. It is therefore possible to accurately grasp the distribution of the cancer tissue and the like by observing the cancer tissue emphasized image.

The display unit 55 displays the blood vessel emphasized image originating from X-ray CT and the cancer tissue emphasized image originating from PCCT imaging. In this case, the display unit 55 preferably displays a composite image constituted by a blood vessel emphasized image and a cancer tissue emphasized image. The image generation unit 53-5 generates a composite image. When the X-ray CT imaging mechanism 152-1 and the PCCT imaging mechanism 153-1 have concurrently imaged the same region in the same time zone, since the coordinate system of the blood vessel emphasized image has already coincided with that of the cancer tissue emphasized image, it is not necessary to align the blood vessel emphasized image with the cancer tissue emphasized image by image processing. In this case, the image generation unit 53-5 combines the blood vessel emphasized image with the cancer tissue emphasized image without registration. When the X-ray CT imaging mechanism 152-1 and the PCCT imaging mechanism 153-1 have individually imaged the same region in different time zones, it is necessary to align the blood vessel emphasized image with the cancer tissue emphasized image by image processing. In this case, the image generation unit 53-5 combines the blood vessel emphasized image with the cancer tissue emphasized image upon performing known registration for the blood vessel emphasized image and the cancer tissue emphasized image.

As described above, the PCCT/CT apparatus 160 can individually generate a blood vessel emphasized image clearly depicting a contrast-enhanced blood vessel region and a cancer tissue emphasized image clearly depicting a cancer tissue. Therefore, the PCCT/CT apparatus 160 can clearly image the vascular system and stromal system of the cancer tissue by executing medical imaging using the contrast agent according to this embodiment.

Note that in the above description, the X-ray computed tomography imaging apparatus performs vascular system imaging, and the PCCT apparatus performs stromal system imaging. However, this embodiment is not limited to this. That is, the PCCT apparatus may perform vascular system imaging, and the X-ray computed tomography imaging apparatus may perform stromal system imaging.

(Nuclear Medicine Imaging/CT Apparatus)

FIG. 34 is a block diagram showing the arrangement of a nuclear medicine imaging/CT apparatus 170 according to this embodiment. As shown in FIG. 34, the nuclear medicine imaging/CT apparatus 170 is a composite apparatus constituted by a nuclear medicine diagnostic apparatus and an X-ray computed tomography imaging apparatus. The nuclear medicine imaging/CT apparatus 170 includes a system control unit 151 as a central unit, an X-ray CT imaging mechanism 153-1, a nuclear medicine imaging mechanism 153-2, an imaging control unit 154-2, an image generation unit 53-6, an image analysis unit 54, a display unit 55, an input unit 56, and a storage unit 57.

The X-ray CT imaging mechanism 153-1 is the imaging mechanism of the X-ray computed tomography imaging apparatus and is used for vascular system imaging. The nuclear medicine imaging mechanism 153-2 is the imaging mechanism of the nuclear medicine diagnostic apparatus and is used for stromal system imaging. The X-ray CT imaging mechanism 153-1 has the same arrangement as that of the X-ray CT imaging mechanism 153-1 of the PCCT/CT apparatus 160. A description of the X-ray CT imaging mechanism 153-1 will therefore be omitted.

As the nuclear medicine imaging mechanism 153-2, a PET apparatus and a SPECT apparatus can be used as needed. For the sake of a concrete description to be made below, assume that the nuclear medicine imaging mechanism 153-2 is a PET apparatus, and the nuclear medicine imaging/CT apparatus 170 is a PET/CT apparatus.

FIG. 35 is a block diagram showing the arrangement of the PET imaging mechanism 153-2. As shown in FIG. 35, the PET imaging mechanism 153-2 is equipped with a gamma ray detection unit 561, a signal processing circuit 564, a coincidence circuit 565, and a gantry control unit 566.

The gamma ray detection unit 561 includes a plurality of gamma ray detectors 562 arranged around the rotation axis Z. An imaging area (FOV) is formed in the opening portion of the gamma ray detection unit 561. A top 563 on which the subject S is placed is inserted into the opening portion of the gamma ray detection unit 561 such that an imaging region of the subject S is included in the imaging area. The subject S is placed on the top 563 such that the body axis coincides with the rotation axis Z. The contrast agent according to this embodiment has been injected into the subject S. As described later, positron-emitting radionuclides are used as a contrast enhancement material for the cancer contrast enhancement particles 20 of the contrast agent. Positron-emitting radionuclides emit positrons. Emitted positrons pair-annihilate with electrons existing around the positrons. A pair of 512-keV gamma rays are emitted in almost opposite directions upon pair annihilation. The gamma ray detectors 562 detect pair annihilation gamma rays emitted from the interior of the subject S to generate a pulse-like electrical signal corresponding to the light amount of detected pair annihilation gamma rays.

The signal processing circuit 564 generates single event data by processing an electrical signal from the gamma ray detector 562 under the control of the gantry control unit 566. More specifically, the signal processing circuit 564 performs detection time measurement processing, position calculation processing, and energy calculation processing. In detection time measurement processing, the signal processing circuit 564 measures the time of the detection of gamma rays by the gamma ray detector 562. In position calculation processing, the signal processing circuit 564 calculates the incident position of annihilation gamma rays based on electrical signals from the gamma ray detectors 562. In energy calculation processing, the signal processing circuit 564 calculates the energy value of annihilation gamma rays striking the gamma ray detectors 562 based on an electrical signal from the gamma ray detector 562. The data of a detection time associated with a single event, the data of position coordinates, and the data of an energy value are associated with each other. A combination of the data of a detection time associated with a single event, the data of position coordinates, and the data of an energy value will be referred to as single event data. Single event data is generated every time an annihilation gamma ray is detected.

The coincidence circuit 565 performs coincidence processing for single event data concerning a plurality of single events under the control of the gantry control unit 566. More specifically, the coincidence circuit 565 repeatedly specifies event data concerning two single events falling within a predetermined time frame among repeatedly supplied single event data. This pair of single events is estimated to originate from the pair annihilation gamma rays generated from the same pair annihilation point. Pairs of single events are collectively called coincidence events. A line connecting the pair of gamma ray detectors 562 which have detected the pair annihilation gamma rays is called an LOR (line of response). In this manner, the coincidence circuit 565 counts coincidence events for each LOR.

The gantry control unit 566 comprehensively controls the respective types of devices mounted on the PET imaging mechanism 153-2 in accordance with instructions from the system control unit 51. For example, the gantry control unit 566 controls the signal processing circuit 564 and the coincidence circuit 565 to perform PET imaging of the subject S injected with the contrast agent according to this embodiment.

As shown in FIG. 34, the imaging control unit 154-2 controls the X-ray CT imaging mechanism 153-1 and the PET imaging mechanism 153-2 to perform medical imaging of the subject S injected with the contrast agent for the PET/CT apparatus 170. In this embodiment, the X-ray CT imaging mechanism 153-1 performs vascular system imaging, and the PET imaging mechanism 153-2 performs stromal system imaging. For this reason, a material having a contrast enhancement effect in the imaging principle of the X-ray CT imaging mechanism 153-1 is used for the blood vessel contrast enhancement particles 10. A material having a contrast enhancement effect in the imaging principle of the PET imaging mechanism 153-2 is used for the cancer contrast enhancement particles 20.

As described above, the contrast agent according to this embodiment contains the blood vessel contrast enhancement particles 10 and the cancer contrast enhancement particles 20. The blood vessel contrast enhancement particles 10 are used for X-ray CT imaging in which vascular system imaging is performed. The blood vessel contrast enhancement particles 10 used for X-ray CT imaging are the same as the blood vessel contrast enhancement particles 10 contained in the contrast agent for the PCCT/CT apparatus 160 described above, and hence a description of them will be omitted.

The cancer contrast enhancement particles 20 are used for PET imaging in which stromal system imaging is performed. Since the cancer contrast enhancement particles 20 used for PET imaging are the same as the cancer contrast enhancement particles 20 contained in the contrast agent for the PET apparatus described above, and hence a description of them will be omitted.

After the contrast agent containing the blood vessel contrast enhancement particles 10 and the cancer contrast enhancement particles 20 described above is injected into the subject S, the X-ray CT imaging mechanism 153-1 and the PET imaging mechanism 153-2 respectively perform X-ray CT imaging and PET imaging at proper timings.

The X-ray CT imaging mechanism 153-1 and the PET imaging mechanism 153-2 typically have mechanically independent structures. For this reason, the X-ray CT imaging mechanism 153-1 and the PET imaging mechanism 153-2 cannot concurrently image the same region in the same time zone. In this case, the X-ray CT imaging mechanism 153-1 and the PET imaging mechanism 153-2 respectively perform X-ray CT imaging and PET imaging sequentially in different time zones. For example, the imaging control unit 154-2 starts X-ray CT imaging by controlling the X-ray CT imaging mechanism 153-1 at the timing when the blood vessel in an imaging region of the subject S is filled with the blood vessel contrast enhancement particles 10. The user can input an imaging start instruction for X-ray CT imaging via the input unit 56 at an arbitrary timing. After the end of the X-ray CT imaging, the X-ray CT imaging mechanism 153-1 is retracted from the imaging region, the PET imaging mechanism 153-2 is positioned to be ready for imaging the imaging region. The imaging control unit 154-2 then starts PET imaging by controlling the PET imaging mechanism 153-2 at the timing when a cancer tissue in the imaging region of the subject S is filled with the cancer contrast enhancement particles 20. More specifically, a gantry control unit 566 of the PET imaging mechanism 153-2 controls a signal processing circuit 564 and a coincidence circuit 565 to perform PET imaging of the subject. The user can input an imaging start instruction for PET imaging via the input unit 56 at an arbitrary timing. Note that the order of execution of X-ray CT imaging and PET imaging can be changed. That is, the PET imaging mechanism 153-2 may perform PET imaging first, and then the X-ray CT imaging mechanism 153-1 may perform X-ray CT imaging.

The image generation unit 53-6 generates a CT image (blood vessel emphasized image) targeting the contrast-enhanced blood vessel based on raw data from the X-ray CT imaging mechanism 153-1. The image generation unit 53-6 reconstructs a PET image (cancer tissue emphasized image) expressing the spatial concentration distribution of the contrast enhancement material contained in the cancer contrast enhancement particles 20 in the subject S based on coincidence event data concerning a plurality of coincidence events from the coincidence circuit 565 of the PET imaging mechanism 153-2.

The display unit 55 displays a blood vessel emphasized image originating from X-ray CT imaging and a cancer tissue emphasized image originating from the PET imaging. In this case, the display unit 55 preferably displays a composite image constituted by the blood vessel emphasized image and the cancer tissue emphasized image. In the PET/CT apparatus 170, the X-ray CT imaging mechanism 153-1 and the PET imaging mechanism 153-2 perform individual imaging of the same region in different time zones. It is therefore necessary to align a blood vessel emphasized image with a cancer tissue emphasized image by image processing. In this case, the image generation unit 53-6 combines the blood vessel emphasized image with the cancer tissue emphasized image upon performing known registration for the blood vessel emphasized image and the cancer tissue emphasized image.

As described above, the PET/CT apparatus 170 can individually generate a blood vessel emphasized image clearly depicting a contrast-enhanced blood vessel region and a cancer tissue emphasized image clearly depicting a cancer tissue. Therefore, the PET/CT apparatus 170 can clearly image the vascular system and stromal system of the cancer tissue by executing medical imaging using the contrast agent according to this embodiment.

Note that although the above description has been made on the PET imaging mechanism as a specific example of the PET imaging mechanism 153-2, this embodiment is not limited to this. That is, the second imaging mechanism 153-2 may be a SPECT imaging apparatus.

A SPECT/CT apparatus is a composite apparatus constituted by a SPECT apparatus and an X-ray computed tomography imaging apparatus. The X-ray computed tomography imaging apparatus performs vascular system imaging. The SPECT apparatus performs stromal system imaging. For this reason, iodine I is preferably used as the contrast enhancement material for the blood vessel contrast enhancement particles 10. In addition, as a contrast enhancement material for the cancer contrast enhancement particles 20, a contrast enhancement material having a contrast enhancement effect in the imaging principle of the SPECT apparatus is preferably used.

(Nuclear Medicine Imaging/MRI Apparatus)

FIG. 36 is a block diagram showing a nuclear medicine imaging/MRI apparatus 180 according to this embodiment. As shown in FIG. 36, the nuclear medicine imaging/MRI apparatus 180 is a composite apparatus constituted by a nuclear medicine diagnostic apparatus and a magnetic resonance diagnostic apparatus. The nuclear medicine imaging/MRI apparatus 180 includes a system control unit 151 as a central unit, an MR imaging mechanism 152-2, a nuclear medicine imaging mechanism 153-2, an imaging control unit 154-3, an image generation unit 53-7, an image analysis unit 54, a display unit 55, an input unit 56, and a storage unit 57.

The MR imaging mechanism 152-2 is the imaging mechanism of a magnetic resonance diagnostic apparatus (MRI apparatus) and used for vascular system imaging. The nuclear medicine imaging mechanism 153-2 is the imaging mechanism of a nuclear medicine diagnostic apparatus and is used for stromal system imaging. The nuclear medicine imaging mechanism 153-2 has the same arrangement as that of the nuclear medicine imaging mechanism 153-2 of the nuclear medicine imaging/CT apparatus 170 described above, and hence a description of the nuclear medicine imaging mechanism 153-2 will be omitted.

FIG. 37 is a block diagram showing the arrangement of the MR imaging mechanism 152-2. As shown in FIG. 37, the MR imaging mechanism 152-2 includes a static field magnet 572, a gradient field power supply 571, a gradient field coil 573, a transmission unit 574, a transmission RF coil 575, a reception RF coil 576, a reception unit 577, and a gantry control unit 578.

The static field magnet 572 has a nearly cylindrical hollow shape and generates a static magnetic field in the nearly cylindrical interior. A spatial area in which the uniformity of a generated magnetic field is high is used for imaging. As the static field magnet 572, for example, a permanent magnet or superconductive magnet is used.

The gradient field power supply 571 supplies a current to the gradient field coil 573 in accordance with a control signal supplied from the gantry control unit 578. The gradient field power supply 571 causes the gradient field coil 573 to generate a gradient magnetic field by supplying a current to the gradient field coil 573. The gradient field coil 573 is mounted inside the static field magnet 572. The gradient field coil 573 generates a gradient magnetic field in accordance with a current supplied from the gradient field power supply 571. A gradient magnetic field is generated to add positional information to an MR signal. More specifically, a gradient magnetic field includes a slice selection gradient magnetic field, a phase encoding gradient magnetic field, and a readout gradient magnetic field. A slice selection gradient magnetic field is used to arbitrarily determine an imaging slice. A phase encoding gradient magnetic field is used to encode the phase of an MR signal in accordance with the spatial position. A readout gradient magnetic field is used to encode the frequency of an MR signal in accordance with the spatial position.

A top on which the subject S is place is inserted into the bore inside the static field magnet 572. A contrast agent for the PET/MRI apparatus 180 is injected into the subject S.

The transmission unit 574 transmits an RF magnetic field for exciting target atomic nuclei existing in the subject S via the transmission RF coil 575. As target atomic nuclei, protons are typically used. More specifically, the transmission unit 574 supplies an RF signal (Radio Frequency signal) for exciting target atomic nuclei to the transmission RF coil 575 in accordance with a control signal supplied from the gantry control unit 578.

The transmission RF coil 575 is arranged on the inner circumferential side of the gradient field coil 573. The transmission RF coil 575 generates an RF magnetic field upon receiving an RF pulse from the transmission unit 574. The generated RF magnetic field oscillates at a resonant frequency unique to target atomic nuclei to excite the target atomic nuclei.

The reception RF coil 576 is arranged on the inner circumferential side of the gradient field coil 573. The reception RF coil 576 electromagnetically detects electromagnetic waves generated from the excited target atomic nuclei, and generates an analog electrical signal corresponding to the energy of the detected electromagnetic waves. The generated electrical signal is called an MR signal. The MR signal is supplied to the reception unit 577.

The reception unit 577 receives an MR signal corresponding to the energy of the electromagnetic waves generated from the excited target atomic nuclei by the reception RF coil 576. More specifically, the reception unit 577 receives an MR signal from the reception RF coil 576 in accordance with a control signal supplied from the gantry control unit 578. The reception unit 577 then generates a digital MR signal by processing the received MR signal. The generated MR signal is supplied to the image generation unit 53-7 via the system control unit 51.

To execute MR imaging based on a predetermined imaging principle for the subject S, the gantry control unit 578 controls the gradient field power supply 571, the transmission unit 574, and the reception unit 577 in accordance with a pulse sequence corresponding to the predetermined imaging principle. Any existing imaging method which can use an MR contrast agent can be applied to MR imaging according to this embodiment. For example, as imaging methods according to the embodiment, an imaging method using the difference in longitudinal relaxation time T1 or transverse relaxation time T2 and a CEST imaging method are suitably used.

As shown in FIG. 36, an imaging control unit 154-3 controls the MR imaging mechanism 152-2 and the PET imaging mechanism 153-2 to perform medical imaging of the subject S injected with the contrast agent for the PET/MRI apparatus 180. In this embodiment, the MR imaging mechanism 152-2 performs vascular system imaging, and the PET imaging mechanism 153-2 performs stromal system imaging. For this reason, a material having a contrast enhancement effect in the imaging principle of the MR imaging mechanism 152-2 is used for the blood vessel contrast enhancement particles 10. A contrast enhancement material having a contrast enhancement effect in the imaging principle of the PET imaging mechanism 153-2 is used for the cancer contrast enhancement particles 20.

A contrast agent for the PET/MRI apparatus 180 will be described below. The cancer contrast enhancement particles 20 are used for PET imaging in which stromal system imaging is performed. The cancer contrast enhancement particles 20 used for PET imaging are the same as the cancer contrast enhancement particles 20 contained in the contrast agent for the PET apparatus described above, and hence a description of them will be omitted. The blood vessel contrast enhancement particles 10 are used for MR imaging in which vascular system imaging is performed. The blood vessel contrast enhancement particles 10 are the same as the blood vessel contrast enhancement particles 10 contained in the contrast agent for the MRI apparatus described above, and hence a description of them will be omitted.

After the contrast agent containing the blood vessel contrast enhancement particles 10 and the cancer contrast enhancement particles 20 is injected into the subject S, the MR imaging mechanism 152-2 and the PET imaging mechanism 153-2 respectively perform MR imaging and PET imaging at proper timings.

The MR imaging mechanism 152-2 and the PET imaging mechanism 153-2 may have mechanically independent structures or a mechanically integrated structure. When having mechanically independent structures, the MR imaging mechanism 152-2 and the PET imaging mechanism 153-2 cannot concurrently image the same region in the same time zone. In this case, the MR imaging mechanism 152-2 and the PET imaging mechanism 153-2 respectively perform MR imaging and PET imaging sequentially in different time zones. For example, the imaging control unit 154-3 starts MR imaging by controlling the MR imaging mechanism 152-2 at the timing when a blood vessel in an imaging region is filled with the blood vessel contrast enhancement particles 10. More specifically, a gantry control unit 578 of the MR imaging mechanism 152-2 performs MR imaging of the subject by controlling a gradient field power supply 572, a transmission unit 574, and a reception unit 577. The user can input an imaging start instruction for MR imaging via the input unit 56 at an arbitrary timing. After the end of MR imaging, the MR imaging mechanism 152-2 is retracted from the imaging region, the PET imaging mechanism 153-2 is positioned to be ready for imaging the imaging region. The imaging control unit 154-3 then starts PET imaging by controlling the PET imaging mechanism 153-2 at the timing when a cancer tissue in the imaging region of the subject S is filled with the cancer contrast enhancement particles 20. The user can input an imaging start instruction for PET imaging via the input unit 56 at an arbitrary timing. Note that the order of execution of MR imaging and PET imaging can be changed. That is, the PET imaging mechanism 153-2 may perform PET imaging first, and then the MR imaging mechanism 152-2 may perform MR imaging.

When the MR imaging mechanism 152-2 and the PET imaging mechanism 153-2 have structures which can perform simultaneous imaging, the imaging control unit 154-3 starts simultaneous imaging including MR imaging and PET imaging by controlling the MR imaging mechanism 152-2 and the PET imaging mechanism 153-2 at the timing when a blood vessel in an imaging region is filled with the blood vessel contrast enhancement particles 10 and a cancer tissue in the imaging region is filled with the cancer contrast enhancement particles 20. The user can input an imaging start instruction for simultaneous imaging via the input unit 56 at an arbitrary timing. For example, it is possible to perform simultaneous imaging including MR imaging and PET imaging by using a gantry integrally including the MR imaging mechanism 152-2 and the PET imaging mechanism 153-2. The gantry concentrically incorporates a plurality of gamma ray detectors around the rotation axis Z as a common axis, in addition to a reception RF coil, a gradient field coil, and a static field magnet. This allows the MR imaging mechanism 152-2 and the PET imaging mechanism 153-2 to share the same imaging area in the same time zone.

The image generation unit 53-7 generates a T1-weighted image or T2-weighted image (blood vessel emphasized image) on which a contrast-enhanced blood vessel region is emphasized based on an MR signal from the reception unit 577 of the MR imaging mechanism 152-2. In addition, the the image generation unit 53-7 reconstructs a PET image (cancer tissue emphasized image) expressing the spatial concentration distribution of the contrast enhancement material contained in the cancer contrast enhancement particles 20 in the subject S based on coincidence event data concerning a plurality of coincidence events from the coincidence circuit 565 of the PET imaging mechanism 153-2.

The display unit 55 displays a blood vessel emphasized image originating from MR imaging and a cancer tissue emphasized image originating from PET imaging. In this case, the display unit 55 preferably superimposes and displays the composite image constituted by the blood vessel emphasized image and the cancer tissue emphasized image. When the MR imaging mechanism 152-2 and the PET imaging mechanism 153-2 have concurrently imaged the same region in the same time zone, since the coordinate system of the blood vessel emphasized image has already coincided with that of the cancer tissue emphasized image, it is not necessary to align the blood vessel emphasized image with the cancer tissue emphasized image by image processing. In this case, the image generation unit 53-7 combines the blood vessel emphasized image with the cancer tissue emphasized image without registration. When the MR imaging mechanism 152-2 and the PET imaging mechanism 153-2 have individually imaged the same region in different time zones, it is necessary to align the blood vessel emphasized image with the cancer tissue emphasized image by image processing. In this case, the image generation unit 53-7 combines the blood vessel emphasized image with the cancer tissue emphasized image upon performing known registration processing for the blood vessel emphasized image and the cancer tissue emphasized image.

As described above, the PET/MRI apparatus 180 can individually generate a blood vessel emphasized image clearly depicting a contrast-enhanced blood vessel region and a cancer tissue emphasized image clearly depicting a cancer tissue.

Note that in the above description, stromal system imaging is performed by MR angiography. However, this embodiment is not limited to this. For example, the MRI apparatus may perform stromal system imaging by CEST imaging at the same timing as the PET imaging or a different timing from the PET imaging. In this case, compound image based on the CEST image and the PET image may be generated by the image generation unit 53-7 as the cancer tissue emphasized image.

When performing CEST imaging, as described above, it is preferable to use a compound containing a paramagnetic metal, which can be an exogenous contrast agent, as the blood vessel contrast enhancement particles 10.

(Effects)

As described above, the medical image diagnostic apparatus 50 according to this embodiment includes the imaging unit 52, the image generation unit 53, and the display unit 55. The imaging unit 52 images the subject injected with the blood vessel contrast enhancement particles 10 for contrast-enhancing a blood vessel and the cancer contrast enhancement particles 20 for contrast-enhancing a diseased tissue. The blood vessel contrast enhancement particle 10 has the first particle size larger than the vascular endothelial cell gap at the time of the occurrence of the EPR effect. The cancer contrast enhancement particle 20 has the second particle size smaller than the gap. The image generation unit 53 generates a medical image associated with the imaging region of the subject based on output data from the imaging unit 52. The display unit 55 displays the medical image.

When the contrast agent according to this embodiment is injected into a blood vessel of a subject, the diseased tissue contrast enhancement particles 20 pass through the vascular endothelial cell gaps Ga of a neighboring blood vessel or new nutrient vessel for a diseased tissue and are accumulated in the diseased tissue. The blood vessel contrast enhancement particles 10 have a particle size larger than the gap Ga, and hence are retained in the blood vessel because of incapability to pass through the gaps Ga.

The medical image diagnostic apparatus 50 according to this embodiment can simultaneously execute both vascular system imaging and stromal system imaging by executing medical imaging at the timing when both the vascular system and stromal system of a diseased tissue are filled with the contrast agent. In this case, when contrast enhancement materials having different contrast enhancement effects are respectively allocated to the contrast enhancement materials for the blood vessel contrast enhancement particles 10 and the cancer contrast enhancement particles 20 contained in the contrast agent, medical imaging capable of clearly discriminating vascular system imaging and stromal system imaging is implemented.

The medical image diagnostic apparatus 50 according to this embodiment may execute individual imaging including vascular system imaging and stromal system imaging by executing vascular system imaging and stromal system imaging at different timings. That is, the medical image diagnostic apparatus 50 may execute vascular system imaging by performing medical imaging at the timing when the vascular system of a diseased tissue is filled with the blood vessel contrast enhancement particles 10, and execute stromal system imaging by performing medical imaging at the timing when the stromal system of the diseased tissue is filled with the cancer contrast enhancement particles 20. In individual imaging, when contrast enhancement materials having different contrast enhancement effects are respectively allocated to the contrast enhancement materials for the blood vessel contrast enhancement particles 10 and the cancer contrast enhancement particles 20 contained in the contrast agent, medical imaging capable of clearly discriminating vascular system imaging and stromal system imaging is implemented.

This makes it possible to provide a medical image diagnostic apparatus capable of clearly imaging the vascular system and stromal system of a diseased tissue.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
a medical imager configured to image a subject who has been injected with blood vessel contrast enhancement particles for contrast enhancing a blood vessel and diseased tissue contrast enhancement particles for contrast enhancing a diseased tissue and generate output data, the blood vessel contrast enhancement particle having a first particle size larger than a gap of vascular endothelial cells under an enhanced permeability and retention (EPR) effect, and the diseased tissue contrast enhancement particle having a second particle size smaller than the gap;
processing circuitry configured to
generate, using the output data, a medical image representing an imaging region of the subject, and
distinguish pixel values of the medical image corresponding to the blood vessel contrast enhancement particles from pixel values corresponding to the diseased tissue contrast enhancement particles to generate data associated with a blood vessel contrast-enhanced by the blood vessel contrast enhancement particles and data associated with the diseased tissue contrast-enhanced by the diseased tissue contrast enhancement particles; and
a display configured to display the medical image, wherein the displayed medical image includes the data associated with a blood vessel contrast-enhanced by the blood vessel contrast enhancement particles and the data associated with the diseased tissue contrast-enhanced by the diseased tissue contrast enhancement particles.

2. The apparatus of claim 1, wherein the processing circuitry is further configured to generate the medical image, wherein the medical image includes a contrast enhanced blood vessel region associated with a blood vessel contrast enhanced by the blood vessel contrast enhancement particles and a contrast enhanced diseased tissue region associated with a diseased tissue contrast enhanced by the diseased tissue contrast enhancement particles.

3. The apparatus of claim 1, wherein
the processing circuitry is further configured to generate the medical image, wherein the medical image includes a blood vessel emphasized image in which a contrast enhanced blood vessel region associated with a blood vessel contrast enhanced by the blood vessel contrast enhancement particle is emphasized more than a contrast enhanced diseased tissue region associated with a diseased tissue contrast enhanced by the diseased tissue contrast enhancement particles, and a diseased tissue emphasized image in which the contrast enhanced diseased tissue region is emphasized more than the contrast enhanced blood vessel region, and
the display displays the blood vessel emphasized image and the diseased tissue emphasized image.

4. The apparatus of claim 3, wherein the imaging unit outputs a first output data set upon imaging the imaging region at a first time, and outputs a second output data set upon imaging the imaging region at a second time, and
the image generation unit generates the blood vessel emphasized image based on the first output data set, and generates the diseased tissue emphasized image based on the second output data set.

5. The apparatus of claim 1, wherein the medical imager comprises
a single imaging mechanism configured to image the subject, and
an imaging controller configured to control the single imaging mechanism and image the subject injected with the blood vessel contrast enhancement particles and the diseased tissue contrast enhancement particles.

6. The apparatus of claim 5, wherein
the single imaging mechanism includes an X ray source configured to generate X rays and an X ray detector configured to detect X rays generated from the X ray source and transmitted through the subject and count a number of detected X ray photons,
the imaging controller controls the X ray source and the X ray detection unit and images the subject injected with the blood vessel contrast enhancement particles and the diseased tissue contrast enhancement particles, and
the processing circuitry is further configured to
generate a blood vessel emphasized image expressing a spatial distribution of the blood vessel contrast enhanced by the blood vessel contrast enhancement particles based on a number of the detected X ray photons that belong to a first energy band corresponding to an attenuation characteristic of a first contrast enhancement material contained in the blood vessel contrast enhancement particles, and
generate a diseased tissue image expressing a spatial distribution of the diseased tissue contrast enhanced by the diseased tissue contrast enhancement particles based on a number of the detected X ray photons belonging to a second energy band corresponding to an attenuation characteristic of a second contrast enhancement material contained in the diseased tissue contrast enhancement particles, the second energy band being different from the first energy band.

7. The apparatus of claim 6, wherein the processing circuitry is further configured to
generate the blood vessel emphasized image based on numbers of the detected X ray photons in a first two energy bands, which include the first energy band, the first two energy bands being on respective sides of an energy band corresponding to a K absorption edge of the first contrast enhancement material, and
generate the diseased tissue image based on numbers of photons in a second two energy bands, which include the second energy band, the second two energy bands being on respective sides of an energy band corresponding to a K absorption edge of the second contrast enhancement material.

8. The apparatus of claim 5, wherein the single imaging mechanism includes
a magnetic field generator configured to individually apply a static magnetic field and a gradient magnetic field to the subject,
a radio frequency (RF) transmitter configured to transmit an RF magnetic field for exciting a specific atomic nucleus in the subject, and
an RF receiver configured to receive a magnetic resonance (MR) signal corresponding to an electromagnetic wave generated from the specific atomic nucleus in the subject upon receiving the applied RF magnetic field, wherein the imaging controller controls the magnetic field generator, the RF transmitter, and the RF receiver to image the subject injected with the blood vessel contrast enhancement particles and the diseased tissue contrast enhancement particles, and the processing circuitry generates an MR image associated with the subject based on an MR signal received from the RF receiver.

9. The apparatus of claim 8, wherein
the processing circuitry is further configured to
generate a diseased tissue emphasized image in which a diseased tissue contrast enhanced by the diseased tissue contrast enhancement particles is emphasized more than a blood vessel contrast enhanced by the blood vessel contrast enhancement particles, based on a first MR signal sequence from the reception unit, and
generate a blood vessel emphasized image in which the blood vessel is emphasized more than the diseased tissue, based on a second MR signal sequence from the reception unit, and
the display displays the diseased tissue emphasized image and the blood vessel emphasized image.

10. The apparatus of claim 8, wherein
a contrast enhancement material for the blood vessel contrast enhancement particles includes a first proton having a first resonant frequency,
a contrast enhancement material for the diseased tissue contrast enhancement particles includes a second proton having a second resonant frequency, which is different from the first resonant frequency,
the processing circuitry is further configured to
generate an in-phase image based on a first MR signal sequence, the in-phase image originating from a spin of the first proton and a spin of the second proton which are in phase with each other,
generate an opposite phase image based on a second MR signal sequence, the opposite phase image originating from a spin of the first proton and a spin of the second proton which are in opposite phase with each other,
generate a diseased tissue emphasized image in which a diseased tissue contrast enhanced by the diseased tissue contrast enhancement particles is emphasized more than a blood vessel contrast enhanced by the blood vessel contrast enhancement particles, based on the in-phase image and the opposite phase image, and
generate a blood vessel emphasized image in which the blood vessel is emphasized more than the diseased tissue based on the second MR signal sequence from the reception unit, and
the display displays the diseased tissue emphasized image and the blood vessel emphasized image.

11. The apparatus of claim 10, wherein
the imaging controller controls the magnetic field application unit, the transmission unit, and the reception unit to execute MR angiography and chemical exchange saturation transfer (CEST) imaging in different time zones,
the processing circuitry generates a blood vessel emphasized image in which a blood vessel contrast enhanced by blood vessel contrast enhancement particles is emphasized more than a diseased tissue contrast enhanced by the diseased tissue contrast enhancement particles, based on an MR signal sequence acquired at the time of the MR angiography, and generates a diseased tissue emphasized image in which the diseased tissue is emphasized more than the blood vessel, based on an MR signal sequence acquired at the time of the CEST imaging, and
the display displays the diseased tissue emphasized image and the blood vessel emphasized image.

12. The apparatus of claim 1, wherein
the medical imager includes a first imaging mechanism configured to image the subject according to a first imaging principle, a second imaging mechanism configured to image the subject according to a second imaging principle, and an imaging controller configured to control the first imaging mechanism and the second imaging mechanism to image the subject injected with the blood vessel contrast enhancement particles and the diseased tissue contrast enhancement particles,
the processing circuitry generates a first medical image based on first output data from the first imaging mechanism, and generates a second medical image based on second output data from the second imaging mechanism, and
the display displays the first medical image and the second medical image.

13. The apparatus of claim 12, wherein the first imaging mechanism comprises a photon counting computed tomography (PCCT) imaging mechanism configured to execute PCCT imaging,
the second imaging mechanism comprises an X ray computed tomography (CT) imaging mechanism configured to execute X ray CT imaging,
the imaging controller controls the PCCT imaging mechanism and the X ray CT imaging mechanism to image the subject injected with the blood vessel contrast enhancement particles and the diseased tissue contrast enhancement particles,
the processing circuitry generates a first medical image based on first output data from the PCCT imaging mechanism and generates a second medical image based on second output data from the X ray CT imaging mechanism, and
the display displays the first medical image and the second medical image.

14. The apparatus of claim 13, wherein the imaging controller controls the PCCT imaging mechanism to image the diseased tissue, and controls the X ray CT imaging mechanism to image the blood vessel,
the processing circuitry generates a diseased tissue image associated with a diseased tissue contrast enhanced by the diseased tissue contrast enhancement particles based on the first output data, and generates a blood vessel emphasized image associated with a blood vessel contrast enhanced by the blood vessel contrast enhancement particles based on the second output data, and
the display displays the diseased tissue image and the blood vessel emphasized image.

15. The apparatus of claim 14, wherein the processing circuitry is further configured to generate the diseased tissue image based on the numbers of photons in two energy bands on both sides of an energy band corresponding to a K absorption edge of a contrast enhancement material contained in the diseased tissue contrast enhancement particles.

16. The apparatus of claim 12, wherein the first imaging mechanism comprises a nuclear medicine imaging mechanism configured to execute nuclear medicine imaging, the second imaging mechanism comprises an X ray CT mechanism configured to execute X ray CT, the imaging controller controls the nuclear medicine imaging mechanism and the X ray CT mechanism to image the subject injected with the blood vessel contrast enhancement particles and the diseased tissue contrast enhancement particles, the processing circuitry is further configured to generate a first medical image based on the first output data from the nuclear medicine imaging mechanism, and generates a second medical image based on the second output data from the X ray CT imaging mechanism, and the display displays the first medical image and the second medical image.

17. The apparatus of claim 16, wherein the imaging controller controls the nuclear medicine imaging mechanism to image the diseased tissue, and controls the X ray CT imaging mechanism to image the blood vessel, the processing circuitry is further configured to generate a diseased tissue emphasized image associated with a diseased tissue contrast enhanced by the diseased tissue contrast enhancement particles based on the first output data, and generates a blood vessel emphasized image associated with a blood vessel contrast enhanced by the blood vessel contrast enhancement particles based on the second output data, and the display displays the diseased tissue emphasized image and the blood vessel emphasized image.

18. The apparatus of claim 17, wherein the imaging controller is further configured to individually execute nuclear medicine imaging for imaging the diseased tissue and X ray CT for imaging the blood vessel.

19. The apparatus of claim 12, wherein the first imaging mechanism comprises a nuclear medicine imaging mechanism configured to execute nuclear medicine imaging, the second imaging mechanism comprises an MR imaging mechanism configured to execute MR imaging, the imaging mechanism controls the nuclear medicine imaging mechanism and the MR imaging mechanism to image the subject injected with the blood vessel contrast enhancement particles and the diseased tissue contrast enhancement particles, the processing circuitry generates a first medical image based on first output data from the nuclear medicine imaging mechanism, and generates a second medical image based on second output data from the MR imaging mechanism, and the display displays the first medical image and the second medical image.

20. The apparatus of claim 19, wherein the imaging controller is further configured to controls the nuclear medicine imaging mechanism to image the diseased tissue and controls the MR imaging mechanism to image the blood vessel, the processing circuitry is further configured to generate a diseased tissue emphasized image associated with a diseased tissue contrast enhanced by the diseased tissue contrast enhancement particles based on the first output data, and generates a blood vessel emphasized image associated with a blood vessel contrast enhanced region by the blood vessel contrast enhancement particles based on the second output data, and the display generates the diseased tissue emphasized image and the blood vessel emphasized image.

21. The apparatus of claim 20, wherein the imaging controller is further configured to concurrently executes nuclear medicine imaging for imaging the diseased tissue and MR imaging for imaging the blood vessel in the same time zone.

22. The apparatus of claim 19, wherein the imaging controller is further configured to controls the MR imaging mechanism to chemical exchange saturation transfer (CEST) image the diseased tissue, and controls the nuclear medicine imaging mechanism to positron emission tomography (PET) image the blood vessel, the processing circuitry is further configured to generate a first image based on the first output data from the MR imaging mechanism, generates a second image based on the second output data from the nuclear medicine imaging mechanism, and generates a composite image based on the first image and the second image, and the display displays the composite image.

23. The apparatus of claim 1, wherein the medical imager is further configured to images the subject at a first acquisition rate in a vascular system imaging period, and images the subject at a second acquisition rate different from the first acquisition rate in a stromal system imaging period after the vascular system imaging period.

24. The apparatus of claim 1, wherein the first acquisition rate and the second acquisition rate have different values corresponding to a ratio of an abundance of the diseased tissue contrast enhancement particles to an abundance of the blood vessel contrast enhancement particles.

25. The apparatus of claim 24, wherein the first acquisition rate has a value larger than that of the second acquisition rate when an abundance of the blood vessel contrast enhancement particles is larger than an abundance of the diseased tissue contrast enhancement particles.

26. The apparatus of claim 24, wherein the first acquisition rate has a value smaller than that of the second acquisition rate when an abundance of the blood vessel contrast enhancement particles is smaller than an abundance of the diseased tissue contrast enhancement particles.

27. The apparatus of claim 23, further comprising an image processor configured to repeatedly calculate a statistic value of a plurality of pixels contained in a region of interest set on the medical image and detect a time point when an increase rate in the statistic value with a lapse of time falls within a predetermined range, wherein the imaging unit images the subject at the first acquisition rate in the blood vessel imaging period from a predetermined time to the detected time point and images the subject at the second acquisition rate in the stromal system imaging period after a lapse of a predetermined time from the detected time point.

28. The apparatus of claim 27, wherein the image processor extracts an image region associated with the diseased tissue contrast enhanced by the diseased tissue contrast enhancement particles from the medical image associated with the stromal system imaging period by threshold processing, and the display displays the extracted image region.

* * * * *